(12) United States Patent
Brandariz Nunez et al.

(10) Patent No.: US 10,059,745 B2
(45) Date of Patent: Aug. 28, 2018

(54) APPLICATIONS OF THE PROTEIN MUNS AND THE DERIVATES THEREOF

(75) Inventors: Alberto Brandariz Nunez, A Coruna (ES); Rebeca Menaya Vargas, A Coruna (ES); Francisco Javier Benavente Martinez, A Coruna (ES); Jose Manuel Martinez Costas, A Coruna (ES)

(73) Assignee: UNIVERSIDADE DE SANTIAGO DE COMPOSTELA, A Coruna (ES)

( * ) Notice: Subject to any disclaimer, the term of this patent is extended or adjusted under 35 U.S.C. 154(b) by 498 days.

(21) Appl. No.: 13/578,556

(22) PCT Filed: Feb. 11, 2011

(86) PCT No.: PCT/ES2011/070092
§ 371 (c)(1),
(2), (4) Date: Aug. 10, 2012

(87) PCT Pub. No.: WO2011/098652
PCT Pub. Date: Aug. 18, 2011

(65) Prior Publication Data
US 2012/0301493 A1 Nov. 29, 2012

(30) Foreign Application Priority Data
Feb. 12, 2010 (ES) .................................. 201030204

(51) Int. Cl.
*A61K 39/15* (2006.01)
*C07K 14/005* (2006.01)
*A61K 38/00* (2006.01)

(52) U.S. Cl.
CPC ............ *C07K 14/005* (2013.01); *A61K 38/00* (2013.01); *C12N 2720/12222* (2013.01)

(58) Field of Classification Search
None
See application file for complete search history.

(56) References Cited

FOREIGN PATENT DOCUMENTS

WO 2006099486 A2 9/2006

OTHER PUBLICATIONS

Rothel et al., Vaccine 1997 vol. 15, Issue 5, pp. 469-472.*
Broering et al. Journal of Virology 2005, vol. 79, pp. 6194-6206.*
Brandariz-Nunes et al. PLOS ONE 2010 vol. 5, Issue 11, no specific pages given.*
Broering T., et al., "Mammalian Reovirus Nonstructural Protein muNS Forms Large Inclusions and Colocalizes with Reovirus Microtubule-Associated Protein mu2 in Transfected Cells", "Journal of Virology", Aug. 2002, pp. 8285-8297, vol. 76, No. 16.
Broering, T., et al., "Reovirus Nonstructural Protein muNS Recruits Viral Core Surface Proteins and Entering Core Particles to Factory-Like Inclusions", "Journal of Virology", Feb. 2004, pp. 1882-1892, vol. 78, No. 4.
Broering, T., et al., "Carboxyl-Proximal Regions of Reovirus Nonstructural Protein muNS Necessary and Sufficient for Forming Factory-Like Inclusions", "Journal of Virology", May 2005, pp. 6194-6206, vol. 79, No. 10.
Miller, C., et al., "Virus-derived Platforms for Visualizing Protein Associations inside Cells", "Molecular & Cellular Proteomics", Mar. 5, 2007, pp. 1027-1038, vol. 6.
Miller, C., et al., "Localization of Mammalian Orthoreovirus Proteins to Cytoplasmic Factory-Like Structures via Nonoverlapping Regions of muNS", "Journal of Virology", Jan. 2010, pp. 867-882, vol. 84, No. 2.
Parker, J., et al., "Reovirus Core Protein mu2 Determines the Filamentous Morphology of Viral Inclusion Bodies by Interacting with and Stabilizing Microtubules", "Journal of Virology", May 2002, pp. 4483-4496, vol. 76, No. 9.
Schmitz, A., et al., "Protein interaction platforms: visualization of interacting proteins in yeast", "Nature Methods", May 31, 2009, pp. 500-502, vol. 6, No. 7.
Touris-Otero, F., et al., "Avian reovirus nonstructural protein muNS forms viroplasm-like inclusions and recruits protein omegaNS to these structures", "Virology", Feb. 5, 2004, pp. 94-106, vol. 319, No. 1.
Touris-Otero, F., et al., "Avian Reovirus Morphogenesis Occurs Within Viral Factories and Begins with the Selective Recruitment of omegaNS and lambdaA to muNS Inclusions", "Journal Molecular Biology", Aug. 6, 2004, pp. 361-374, vol. 341, No. 2.
Armstrong, C., et al., "Rational design of peptide-based building blocks for nanoscience and synthetic biology", "Faraday Discussions", 2009, pp. 305-317, vol. 143.
Burkhard, P., et al., "Coiled Coils: A Highly Versatile Protein Folding Motif", "TRENDS in Cell Biology", Feb. 2001, pp. 82-88, vol. 11, No. 2.
Litowski, J., et al., "Designing Heterodimeric Two-stranded alpha-Helical Coiled-coils", "The Journal of Biological Chemistry", Oct. 4, 2002, pp. 37272-37279, vol. 277, No. 40.
Moutevelis, E., et al., "A Periodic Table of Coiled-Coil Protein Structures", "Journal of Molecular Biology", 2009, pp. 726-732, vol. 385.
Antczak, J., et al, "Retrovirus Genome Segment Assortment into Progeny Genomes Studied by the Use of Monoclonal Antibodies Directed Against Reovirus Proteins", "Virology", 1992, pp. 760-776, vol. 187, Publisher: Academic Press, Inc.
Benavente, J., et al, "Early Steps in Avian Reovirus Morphogenesis", "CTMI", 2006, pp. 67-85, vol. 309, Publisher: Springer-Verlag Berlin Heidelberg.

(Continued)

*Primary Examiner* — Shanon A. Foley
*Assistant Examiner* — Myron G Hill
(74) *Attorney, Agent, or Firm* — Hultquist, PLLC; Steven J. Hultquist

(57) ABSTRACT

The invention is based on the identification of the minimum region of the avian *Orthoreovirus* muNS protein which is capable of forming inclusions as well as on the identification of specific regions of the muNS protein showing capacity to associate with the inclusions formed by muNS. The identification of said regions allows developing methods for purifying recombinant polypeptides as well as methods for detecting the interaction between two polypeptides of interest.

6 Claims, 38 Drawing Sheets
Specification includes a Sequence Listing.

(56) References Cited

OTHER PUBLICATIONS

Brandariz-Nunez, A, et al, "Avian Reovirus NS Protein Forms Homo-Oligomeric Inclusions in a Microtubule-Independent Fashion, Which Involves Specific Regions of Its C-Terminal Domain", "Journal of Virology", Feb. 24, 2010, pp. 4289-4301, vol. 84, No. 9, Publisher: American Society for Microbiology.

Su, Y, et al., "The sequence and phylogenetic analysis of avian reovirus genome segments Ml, M2, and M3 enclding the minor core protein A, the major outer capsid protein B, and the nonstructural protein NS", "Journal of Virological Methods", 2006, pp. 146-157, vol. 133, Publisher: Science Direct.

Touris-Otero, F., et al, "Characterization of the nucleic acid-binding activity of the avian reovirus non-structural protein NS", "Journal of General Virology", 2005, pp. 1159-1169, vol. 86, No. http://vir.sgmjourna, Publisher: SGM.

\* cited by examiner

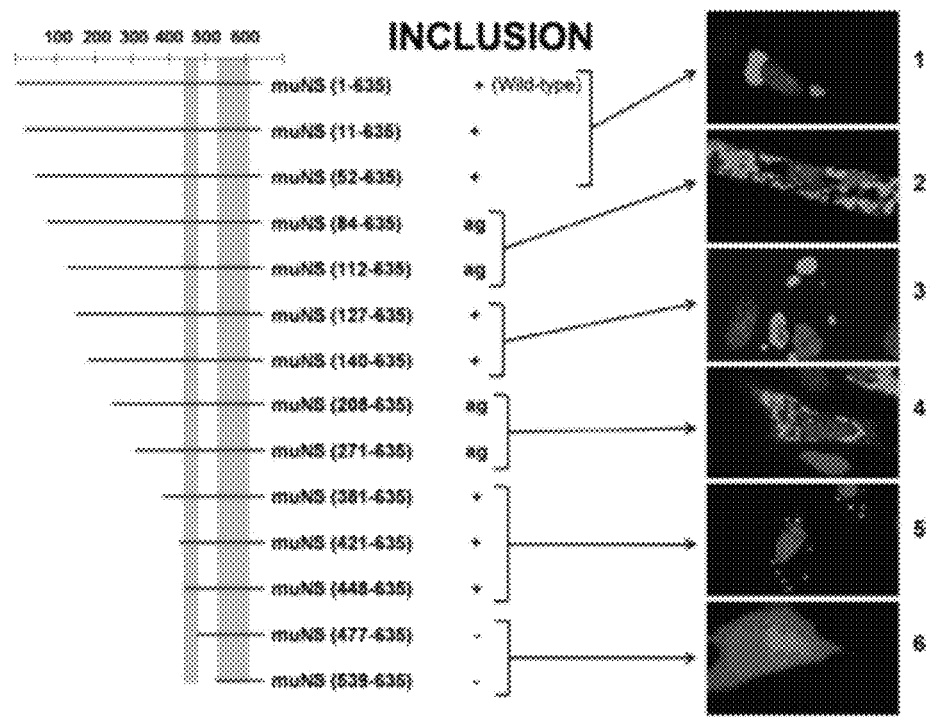
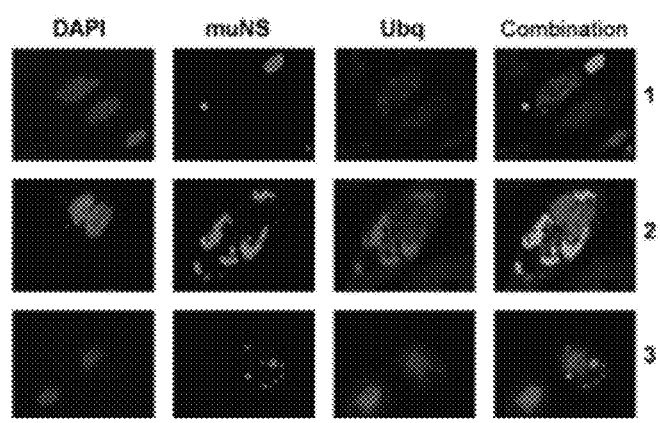
FIG. 2

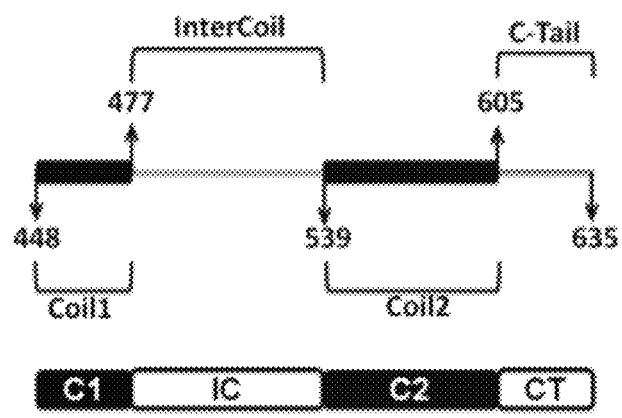
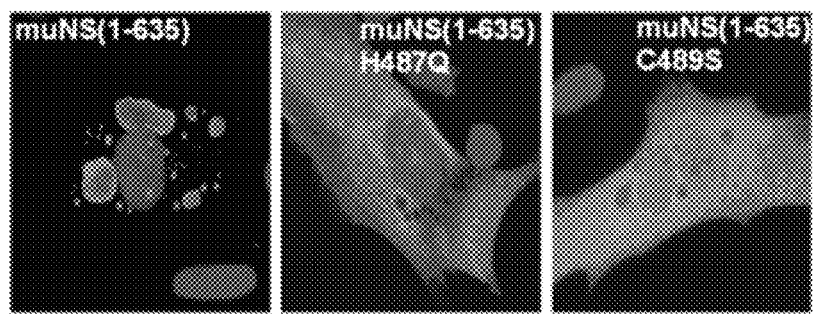
FIG. 3

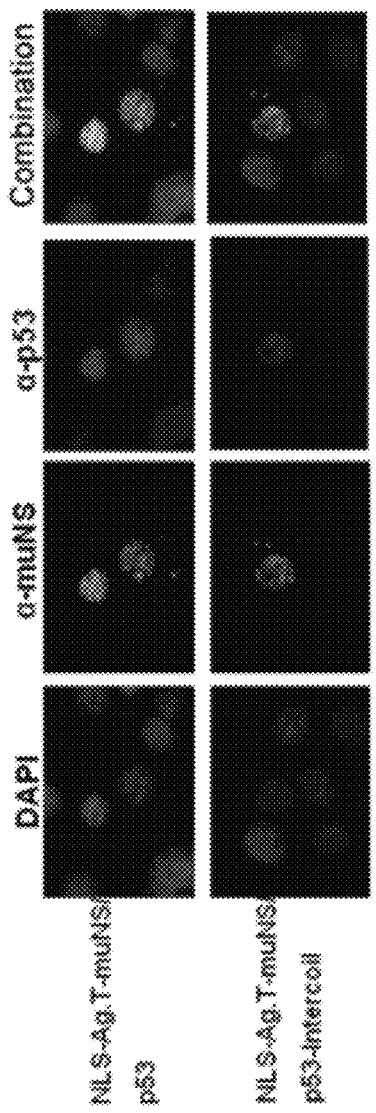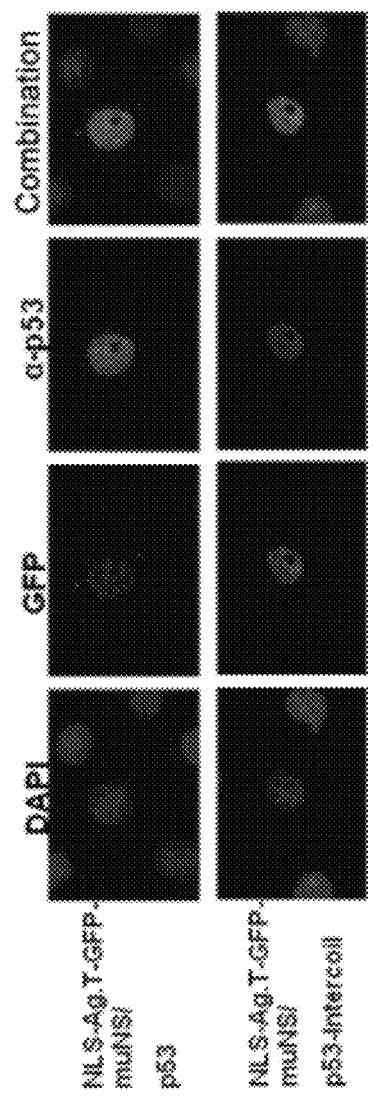
FIG. 29

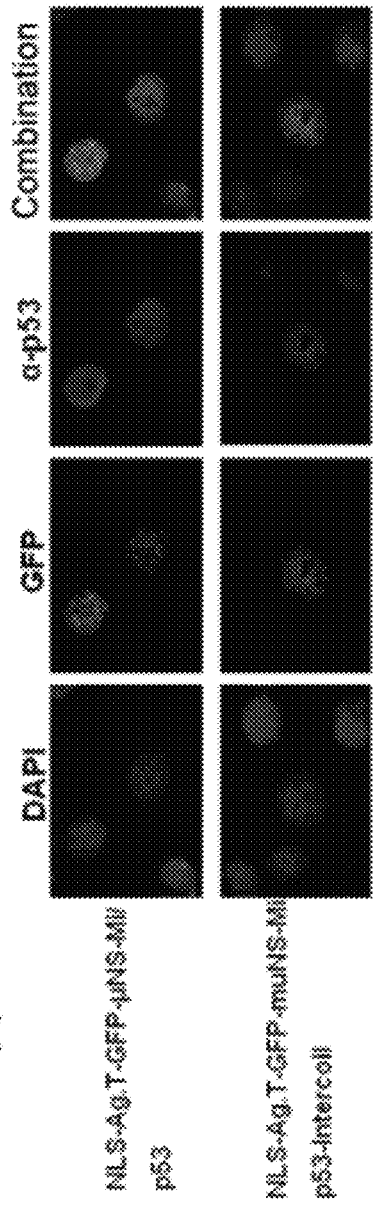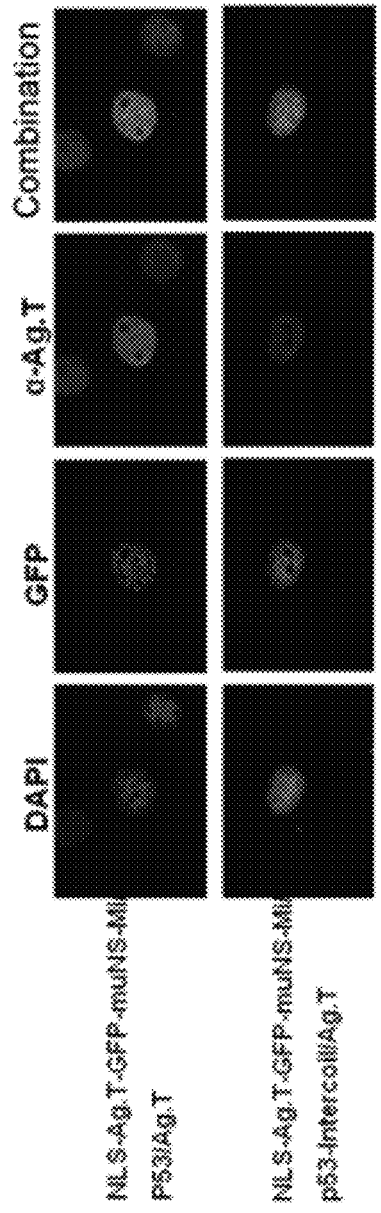
FIG. 31

APPLICATIONS OF THE PROTEIN MUNS AND THE DERIVATES THEREOF

CROSS-REFERENCE TO RELATED APPLICATIONS

This application is a U.S. national phase application under the provisions of 35 U.S.C. § 371 of International Patent Application No. PCT/ES2011/070092 filed Feb. 11, 2011, which in turn claims priority of Spanish Patent Application No. P201030204 filed Feb. 12, 2010. The disclosures of such international patent application and Spanish priority patent application are hereby incorporated herein by reference in their respective entireties, for all purposes.

FIELD OF THE INVENTION

The invention relates to the identification of the minimum region of the avian *Orthoreovirus* muNS protein capable of forming inclusions. Likewise, the invention relates to a purification method and a detection method for detecting the interaction between two polypeptides based on the capacity of some regions of the muNS protein to be incorporated into the inclusions together with a peptide of interest.

BACKGROUND OF THE INVENTION

Avian reoviruses are members of the genus *Orthoreovirus*, one of the 12 genera of the family Reoviridae (Attoui et al., 2000, J. Gene. Virol. 81:1507-15). These viruses are important bird pathogens and cause significant economical losses in poultry farming industry (Jones, 2000. Rev. Sci. Tech. 19: 614-25). Avian reoviruses are viruses without lipid envelope which replicate in the cytoplasm of the infected cells and have a genome with 10 segments of double stranded RNA surrounded by two concentric protein shells of 85 nm in diameter (Zhang et al., 2005. Virology, 343: 25-35). Their genomic segments are divided into three classes according to their electrophoretic mobility, three of class L (large), another three of class M (medium) and four of class S (small) (Varela and Benavente, 1994. J. Virol. 68: 6775-7). With the exception of the tricistronic segment S1, all the other genes are monocistronic (Bodelon et al., 2001. Virology, 290: 181-91). The genomic segments are translated by means of an RNA-dependent polymerase to produce messenger RNAs (mRNA) with a nucleotide sequence identical to that of the positive strand of the segment of double stranded RNA (Li et al., 1980. Virology, 105: 41-51). Viral mRNAs perform two functions in the infected cells: they program the viral protein synthesis in the ribosomes and serve as a template for synthesizing negative strands of the genomic segments.

The genome of avian reovirus encodes at least 12 proteins, 8 of which are structural proteins (which are incorporated into virion), and 4 non-structural proteins which are expressed in infected cells but do not form part of the mature reovirions (Martínez-Costas et al., 1997. J. Virol. 71: 59-64). The proteins encoded by class L genes are called lambda (λ), those encoded by class M genes are called mu (μ) and those encoded by class S genes are called sigma (σ). An alphabetical suffix (λA, λB, etc.) has been assigned to the structural proteins of each class according to their electrophoretic mobility. Reovirion contains at least 10 different structural proteins different, 8 of which (λA, λB, λC, μA, μB, σA, σB and σC) are primary products from their mRNA translation, whereas the other two, μBN and μBC resulted from the proteolytic processing of the precursor μB (Varela et al., 1996. J. Virol. 70: 2974-81). In addition to the structural proteins, avian reoviruses express four non-structural proteins. Therefore, genes M3 and S4 express two major non-structural proteins called μNS and σNS, respectively (Varela and Benavente, 1994, mentioned ad supra) whereas p10 and p17 are encoded by the first two cistrons of the S1 gene (Bodelon et al., 2001, mentioned ad supra).

Avian reoviruses replicate in globular cytoplasmic inclusions called viral factories or viroplasmas which contain structural and non-structural viral proteins, however they lack membranes and cellular organelles (Touris-Otero et al., 2004; J. Mol. Biol. 341: 361-74). The individual expression of viral proteins in transfected cells revealed that non-structural muNS protein is the only protein of the avian reovirus capable of forming inclusions when it is expressed in the absence of other viral factors (Touris-Otero et al., 2004; mentioned ad supra). This, and the fact that the globular cytoplasmic inclusions formed by muNS in transfected cells are very similar in appearance to the viral factories of infected cells, suggest that muNS is the minimum viral factor required for forming viral factories in infected cells with avian reovirus. The analysis of transfected cells that co-express muNS and other viral proteins revealed that muNS plays an important role in the early steps of virus morphogenesis and that the recruitment of avian reovirus proteins into the viral factories is a selective and temporally controlled process (Touris-Otero et al., 2004; mentioned ad supra).

Mammalian reovirus also replicate in globular cytoplasmic inclusions. Like the avian reoviruses, the non-structural muNS protein has been found to be involved in inclusion formation, as well as in the recruitment of other components into the inclusions for possible involvements in genome replication and in particle assembly.

Despite the fact that avian and mammalian reovirus muNS proteins show only 28.3% of sequence identity, they both contain two regions in their C-terminus end with a high "coiled-coil" structure probability. On the other hand, the mammalian protein is 86 amino acids longer and is capable of making more primary contacts with other structural and non-structural viral proteins than the avian protein (Broering et al. 2004; J. Virol. 78: 1882-92). Even though the muNS proteins of all mammal reovirus (MRV) strains produce globular inclusions when they are expressed in transfected cells, most of the strains produce viral factories with filamentous morphology during infection (Parker et al. 2002; J. Virol. 76:4483-96; Broering et al., 2002 J. Virol. 76: 8285-8297). The filamentous phenotype of the mammalian reovirus factories has been attributed to the mu2 protein, due to its capacity to associate both with microtubules and with mammalian reovirus muNS. The expression of the truncated versions of MRV muNS in transfected cells revealed that the segment between the residues 471-721 is the smallest region of muNS necessary and sufficient for forming inclusions (Broering et al. 2005; J. Virol. 79: 6194-6206). It is predicted that this region contains two segments of sequences with high "coiled-coil" structure-forming probability, which are bound by a region, preceded by a section of approximately 50 residues and followed by a C-terminus tail. Despite the fact that minimum region of muNS in MRV capable of forming inclusions has been described, said region has not been identified in avian reoviruses. In the present specification, in addition to determining said region, muNS domains capable of being incorporated into the cytoplasmic inclusions formed by the whole protein is described to check which of the domains are directly involved in the interaction between the monomers of muNS and to thus develop a method for purifying proteins, as well as a method for detecting the interaction between polypeptides.

There are several systems designed today for determining protein interaction of which the double hybrid system is the most popular. This system is based on the expression of two fusion proteins: one in which the X protein is fused to the DNA-binding domain of the transcription factor GCN4; and another in which the Y protein is fused to the transcription activation domain of the same factor GCN4. If X and Y interact, they are expected to reconstruct a functional GCN4 in the cell which will activate the transcription of a reporter gene. The most obvious problems of this system include: i) even though X and Y interact, the architecture of said interaction does not usually allow reconstructing a functional GCN4; ii) the fusions may alter the structures of the different GCN4 domains or of the interaction domains between the test proteins.

A new system using the formation of inclusions by mammalian reovirus muNS protein as a platform for detecting interactions between proteins in vivo in mammalian cells has been described recently (Miller et al., 2007. Mol Cell Proteomics. 6, 1027-38) and it has also been adapted for use in yeasts (Schmitz et al., 2009. Nat Methods; 6, 500-2). In this system, the test protein fuses with the C-terminus area of muNS so that the fusion generates cytoplasmic inclusions and attracts ligand of the test protein thereto. In the yeast system, these authors show that their system is better than the double hybrid system in the number and type of interactions detected, at least with the proteins assayed in said research. However, this system has several problems which include: i) certain proteins may fold incorrectly when fused with muNS-Mi and loss capacity to interact with their ligands; ii) some proteins may interfere with muNS-Mi inclusion-forming capacity and, do not form inclusions or generate intracellular aggregates, the detection of interactions of being largely altered; iii) the intracellular location of the test protein or the ligand may not be suitable to enable detecting same in cytoplasmic inclusions.

Therefore, there is a need in the state of the art to develop a system having advantages with respect to the existing systems, in which for example, the protein fused to the inclusions does not alter the formation of said inclusions, the fused protein maintains its activity and several epitopes can be included in said inclusions.

SUMMARY OF THE INVENTION

In one aspect, the invention relates to a polypeptide, hereinafter polypeptide of the invention, comprising amino acids 448 to 635 (SEQ ID NO:1) of the muNS protein of an avian *Orthoreovirus* or a functionally equivalent variant of said region and having inclusion-forming capacity when it is expressed in a cell, wherein said polypeptide is not the complete avian muNS protein.

In a second aspect, the invention relates to a polynucleotide encoding the polypeptide of the invention and to a cell comprising said polynucleotide or the polypeptide of the invention.

In another aspect, the invention relates to a fusion protein, hereinafter fusion protein of the invention comprising:
(i) a first component containing at least one polypeptide of interest; and
(ii) a second component selected from the group of:
a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

wherein the second component does not contain a polypeptide comprising the amino acids of mammalian *Orthoreovirus* muNS protein corresponding to sequence 605-635 (SEQ ID NO: 6) of said avian protein.

In another aspect the invention relates to a polynucleotide encoding the fusion protein of the invention, as well as to a cell including the fusion protein of the invention or the polynucleotide encoding the fusion protein of the invention.

In another aspect the invention relates to a kit comprising:
(i) a first component selected from the group of:
(a) a polynucleotide encoding the muNS protein of an *Orthoreovirus* or a functionally equivalent variant;
(b) a polynucleotide encoding a polypeptide comprising amino acids 448-635 (SEQ ID NO:1) of avian *Orthoreovirus* muNS protein or the corresponding sequence of mammalian *Orthoreovirus* muNS protein or a functionally equivalent variant of any of the above; and
(c) a cell expressing the muNS protein of an *Orthoreovirus* or a polypeptide comprising amino acids 448-635 (SEQ ID NO:1) of said protein or the corresponding sequence of mammalian *Orthoreovirus* muNS protein or a functionally equivalent variant of any of the above; and
(ii) a second component selected from the group of:
(a) a polynucleotide encoding a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
(b) a polynucleotide encoding a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
(c) a polynucleotide encoding a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
(d) a polynucleotide encoding a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

In another aspect, the invention relates to a fusion protein for use in medicine, comprising:
  (i) a first component containing at least one polypeptide of interest; and
  (ii) a second component selected from the group of:
    a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
    a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
    a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
    a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

In another aspect, the invention relates to the use of a fusion protein comprising:
  (i) a first component containing at least one polypeptide of interest; and
  (ii) a second component selected from the group of:
    a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
    a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
    a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
    a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;
for incorporating the first component into the inclusions resulting from the cell expression of the polypeptide comprising amino acids 448 to 635 (SEQ ID NO: 1) of avian *Orthoreovirus* muNS protein or the corresponding amino acids of mammalian *Orthoreovirus* or the complete avian or mammalian *Orthoreovirus* muNS protein or a functionally equivalent variant of any of the above.

In another aspect, the invention relates to a method for purifying the inclusions formed by a polypeptide selected from the group: polypeptide comprising amino acids 448-635 (SEQ ID NO: 1) of avian *Orthoreovirus* muNS protein, the corresponding amino acids of mammalian *Orthoreovirus* muNS protein, the complete avian or mammalian *Orthoreovirus* muNS protein and a functionally equivalent variant of any of the above which comprises:
  (a) expressing said polypeptide in a cell and maintaining said cell in conditions suitable for inclusion formation; and
  (b) purifying said inclusions.

In another aspect, the invention relates to method for purifying a fusion protein comprising a polypeptide of interest from a composition containing said fusion protein which comprises:
  (a) contacting the inclusions formed by a polypeptide selected from the group formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with a composition containing the fusion protein to be purified wherein said fusion protein comprises:
    (i) a first component containing at least one polypeptide of interest and
    (ii) a second component selected from the group of:
      a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
      a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
      a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
      a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above,
    and maintaining in suitable conditions so that the inclusions interact with the second component of the fusion protein;
  (b) purifying the complex formed between the inclusions and fusion protein; and
  (c) separating the fusion protein from the inclusions.

In another aspect, the invention relates to a method for purifying a fusion protein comprising a polypeptide of interest from a composition containing said fusion protein comprising:
  (a) contacting a polypeptide with inclusion-forming capacity in the presence of divalent cations selected from the group formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with said composition containing the fusion protein to be purified, wherein said fusion protein comprises:
(i) a first component containing at least one polypeptide of interest; and
(ii) a second component selected from the group of:
a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;
wherein the polypeptide with inclusion-forming capacity in the presence of divalent cations is in soluble form and
wherein said contacting is performed in the presence of a divalent cation concentration suitable for forming inclusions from the polypeptide with inclusion-forming capacity and from the fusion protein,
(b) purifying the complex formed in step (a) and
(c) separating the fusion protein from the polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above.

In another aspect, the invention relates to a method for detecting the interaction between a first polypeptide and a second polypeptide comprising:
(a) expressing in a cell the polypeptide selected from the group containing polypeptide comprising amino acids 448-635 (SEQ ID NO: 1) of avian *Orthoreovirus* muNS protein, the corresponding amino acids of mammalian *Orthoreovirus* muNS protein, complete avian *Orthoreovirus* muNS protein, complete mammalian *Orthoreovirus* muNS protein and a functionally equivalent variant of any of the above and maintaining said cell in conditions suitable for inclusion formation;
(b) expressing in said cell a fusion protein comprising:
(i) a first component containing the first polypeptide; and
(ii) a second component selected from the group of:
a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.
in suitable conditions so that the fusion protein is directed to the inclusions expressed in step (a);
(c) expressing the second polypeptide in said cell or maintaining said cell in suitable conditions so that it expresses said second polypeptide and
(d) determining whether the second polypeptide is associated with the complex formed by the inclusions generated in step (a) and the fusion protein expressed in step (b), wherein if the second polypeptide is detected it is indicative of the interaction between said first and second polypeptide
wherein steps (a), (b) and (c) are carried out in any order.

In another aspect, the invention relates to a method for detecting the interaction between a first polypeptide and a second polypeptide which comprises:
(a) contacting a polypeptide with inclusion-forming capacity in the presence of divalent cations wherein said polypeptide is selected from the group formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with a fusion protein to be purified, wherein said fusion protein comprises:
(i) said first polypeptide and
(ii) a second component selected from the group of:
a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;
wherein the polypeptide with inclusion-forming capacity in the presence of divalent cations is in soluble form and
wherein said contacting is performed in the presence of a divalent cation concentration suitable for forming inclusions from the polypeptide with inclusion-forming capacity and from the fusion protein, (b) contacting the inclusions formed in step (a) with said second polypeptide (c) determining whether the second polypeptide is associated with the inclusions generated in step (a), wherein if the second polypeptide is detected it is indicative of the interaction between said first and second polypeptide.

BRIEF DESCRIPTION OF THE DRAWINGS

FIG. 2 shows a summary of the truncations at the N-terminus end of muNS. (A) The deletions of muNS from N-terminus are indicated in the manner similar to that of FIG. 1. The capacity of the constructs to form intracellular inclusions or aggregate (ag) is indicated as positive (+) or negative (−). (B) Immunofluorescence analysis of the N-terminus deletions. The CEF cells were fixed 18 h after transfection with plasmids expressing the complete muNS protein (1), muNS (112-635) (2) or muNS (381-635) (3), as examples of large, aggregated and small inclusions, respectively. The cells were detected with rabbit anti-muNS antibodies (muNS) and mouse anti-conjugated ubiquitin antibodies (Ubq). The secondary antibodies used were Alexa 488-conjugated goat anti-rabbit antibody and Alexa 594-conjugated goat anti-mouse antibody, respectively. The colocalization of muNS (112-635) (2) and the conjugated ubiquitin in the combined image is indicated by a lighter color. The nuclei were stained with DAPI.

FIG. 3 shows the composition of the muNS-Mi domains and the relevance of the Intercoil domain. (A) Diagram of the minimum fraction of muNS protein with inclusion-forming capacity (muNS-Mi). The four domains making up the protein are indicated with the amino acid positions marking the inter-domain positions: Coil1 or C1 (448-477); Intercoil or IC (477-542); Coil2 or C2 (539-605) and C-tail or CT (605-635). (B) Immunofluorescence analysis of N-terminus deletions. CEF cells were fixed after 18 h from the transfection with plasmids expressing complete muNS (1-635) or muNS with point mutations in the Intercoil domain, as indicated in the figure.

FIG. 29 shows the intracellular distribution of p53 or p53-Intercoil in the presence of the nuclear inclusions formed by NLS-Ag.T-muNS or NLS-Ag.T-GFP-muNS in Cos-7 cells. (A) Subcellular localization of p53 or p53-Intercoil in the presence of inclusions formed by NLS-Ag.T-muNS. The nuclei were stained with DAPI (blue). (B) Subcellular localization of p53 or p53-Intercoil in the presence of inclusions formed by NLS-Ag.T-GFP-muNS. In (A) and (B), the semi-confluent Cos-7 cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and in (A), polyclonal anti-muNS antibodies followed by an Alexa 488-conjugated secondary antibody. The NLS-Ag.T-GFP-muNS was viewed directly. The nuclei were stained with DAPI. A diagram of what is shown in the immunofluorescence images is depicted on the right of the panels according to the standards of the diagram of FIG. 13.

FIG. 31 shows the intracellular distribution of the SV40 T-antigen in the presence of NLS-Ag.T-GFP-muNS-Mi co-expressed with p53 or p53-Intercoil in Cos-7 cells. (A) Subcellular localization of p53 or p53-Intercoil in the presence of inclusions formed by NLS-Ag.T-GFP-muNS-Mi. (B) Subcellular localization of the T-antigen in cells co-expressing NLS-Ag.T-GFP-muNS-Mi and p53 or NLS- Ag.T-GFP-muNS-Mi and p53-Intercoil. In (A) and (B), the semi-confluent Cos-7 cells were co-transfected with the plasmids expressing the proteins indicated on the left of the figure. The cells were fixed at 24 h.p.t. and were then subjected to indirect immunofluorescence with a monoclonal anti-p53 antibody (in A) or the T-antigen (in B) followed by an Alexa 592-conjugated secondary antibody. The NLS-Ag.T-GFP-muNS-Mi was viewed directly. The nuclei were stained with DAPI. A diagram of what is shown in the immunofluorescence images is depicted on the right of the panels according to the standards of the diagram of FIG. 13.

DETAILED DESCRIPTION OF THE INVENTION

Figure 1:
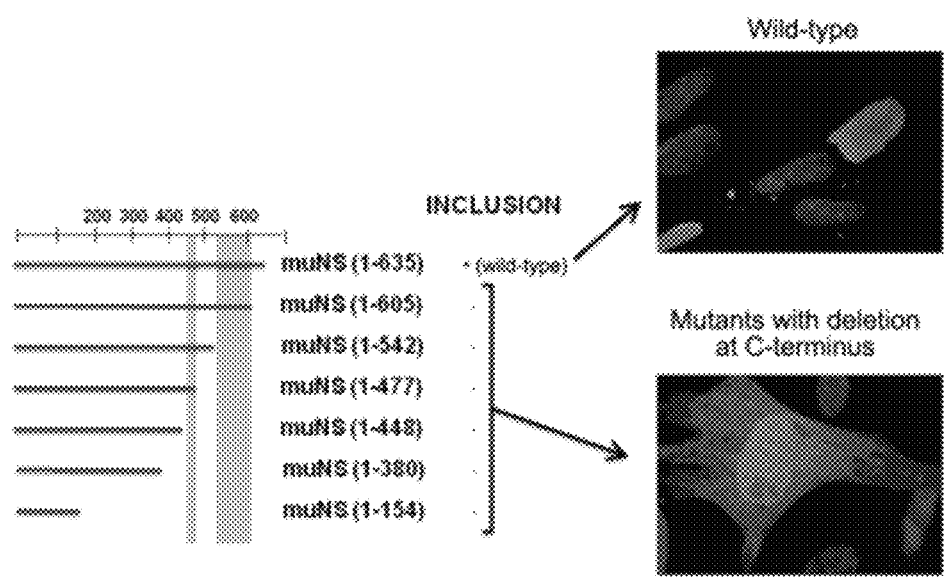
FIG. 1 shows a summary of the truncations at the C-terminus end of muNS. The complete muNS protein is schematically indicated by a black horizontal line covering residues 1-635 (top numbered positions). A similar line at the bottom indicates each truncation covering approximately the muNS portion it represents. The position of the two coiled-coil domains are depicted as vertical gray bars. The capacity of the constructs to form intracellular inclusions is indicated as positive (+) or negative (−), and fluorescence microscopy images of transfected CEF cells are shown on the right of the figure.

The authors of the present invention have clearly shown that, surprisingly, a region of 187 amino acids of avian reovirus muNS protein (hereinafter muNS-Mi) is sufficient for the effective formation of inclusions. The inventors have also developed a method for purifying polypeptides based on the capacity of some regions of said protein to interact with the inclusions formed by the complete *Orthoreovirus* muNS protein, as well as with the inclusions formed by the muNS-Mi region. Similarly, the authors have developed a system for detecting interactions between two polypeptides.

The method for detecting interactions of the invention is much more versatile than that described by Miller et al., 2007. (mentioned ad supra) for mammalian reovirus muNS protein and it also solves the main problems since i) the possibilities of mis-folding are lower since the size of the tag is reduced (the Intercoil domain has 66 residues with respect to muNS-Mi 250 residues) and since inclusions are not formed per se; ii) it does not depend on the possible interference of the test protein in inclusion formation since said protein is directed to the inclusions formed by muNS, muNS-Mi and their derivatives which can even be fluorescents to facilitate tracking; iii) several different proteins can be integrated at the same time in the same inclusion; and iv) the method of the invention has been adapted to nuclear behavior where the interactions between nuclear proteins can be detected naturally.

Minimum Region of muNS Protein Capable of Forming Inclusions

The authors of the present invention have clearly shown that the region of the avian reovirus muNS protein corresponding to the residues 448 to 635 is the minimum region conserving the capacity of the complete protein to form inclusions, as shown in Example 1.

Therefore, in a first aspect, the invention relates to a polypeptide, hereinafter polypeptide of the invention, comprising amino acids 448 to 635 (SEQ ID NO: 1) of the muNS protein of an avian *Orthoreovirus* or a functionally equivalent variant of said region, hereinafter muNS-Mi and having inclusion-forming capacity when it is expressed in a cell, wherein said polypeptide is not the avian *Orthoreovirus* muNS protein.

The term "polypeptide", used interchangeably herein with protein, refers to an amino acid chain of any length wherein the different amino acids bind to one another by means of peptide bonds or by disulfide bridges.

The term "muNS protein of an avian *Orthoreovirus*" or "μNS protein of an avian *Orthoreovirus*", as used in the present invention, refers to one of the non-structural proteins encoded by the M3 gene of avian reovirus or avian *Orthoreovirus* and is the only protein of the avian reovirus capable of forming inclusions when expressed in the absence of other viral factors (Touris-Otero et al. Virology, 319; 94-106). It is a protein with 635 amino acids defined by the accession number AY608700 in the NCBI database (SEQ ID NO:56).

The term "avian *Orthoreovirus*" or "avian reovirus", as used in the present invention, refers to one of the twelve genera belonging to the Reoviridae virus family and specifically to the group within the genus infecting birds. They have dsRNA genomes and are therefore group III viruses.

The term "inclusion", as used in the present invention, refers to nuclear or cytoplasmic aggregates, normally protein aggregates. Specifically, the protein forming the inclusions in the genus *Orthoreovirus* is muNS or μNS protein, which is one of the non-structural proteins encoded by the M3 gene and is the only protein of the avian reovirus capable of forming inclusions when expressed in the absence of other viral factors (Touris-Otero et al. supra.).

"Functionally equivalent variant" of the region formed by amino acids 448 to 635 (SEQ ID NO:1) of the avian muNS protein is understood as all those polypeptides derived from the muNS sequence by means of modifying, inserting and/or deleting one or more amino acids, provided that the function of the muNS proteins mentioned previously is substantially maintained. Specifically, the functionally equivalent variant shows at least one function related to the capacity to generate inclusions in a cell.

Variants suitable for use in the present invention include those showing at least 25%, at least 40%, at least 60%, at least 70%, at least 80%, at least 90%, at least 95%, at least 96%, at least 97%, at least 98% or at least 99% of sequence identity with respect to the muNS sequences indicated above. The degree of identity between two amino acid sequences can de determined by conventional methods, for example, by means of basic sequence alignment algorithms known in the state of the art, such as, for example BLAST (Altschul S. F. et al. Basic local alignment search tool. J Mol Biol. 1990 Oct. 5; 215(3):403-10). The person skilled in the art will understand that the amino acid sequences referred to in this description can be chemically modified, for example, by means of physiologically relevant chemical modifications, such as, phosphorylations, acetylations, etc. Methods suitable for determining the inclusion-generating capacity of muNS, muNS-Mi or the functionally equivalent variant of muNS-Mi includes, but not limited to the method described in Example 1 of the present invention based on the expression of muNS or muNS-Mi and the detection by indirect immunofluorescence using polyclonal anti-muNS antibodies, the formation of said inclusions thus being able to be confirmed.

Likewise, the invention relates to a polynucleotide encoding said polypeptide, hereinafter polynucleotide of the invention and a cell comprising the polypeptide or the polynucleotide, hereinafter the cell of the invention.

The term "polynucleotide", as used in the present invention, refers to a polymer formed by a variable number of monomers wherein the monomers are nucleotides, including both ribonucleotides and deoxyribonucleotides. The polynucleotides include monomers modified by means of methylation or as well as non-modified forms. The terms "polynucleotide" and "nucleic acid" are used interchangeably in the present invention and they include mRNA, cDNA and recombinant polynucleotides.

The cell of the invention can be any prokaryotic cell or any eukaryotic cell. Practically any cell type can be used in the present invention, such as shown in Examples 1, 6 and 8, in which CEF cells, Insect Sf9 cells and COST cells are used. Any host cell which can be transformed with the polynucleotide of the invention or which can be transformed, transfected or infected by a recombinant vector containing the polynucleotide of the invention, for example animal cells (such as mammalian cells, bird cells, insect cells, etc.), plant cells, yeasts, bacteria, etc. The cells of the invention can be obtained by means of conventional methods known by the persons skilled in the art [Sambrook et al., Cold Spring Harbor Laboratory Press, third edition, 2001].

In a particular embodiment, the polypeptide of the invention additionally comprises a component selected from the group: peptide to facilitate its purification and nuclear signaling peptide.

The term "peptide to facilitate its purification", as used in the present invention, refers to a peptide useful for isolating or purifying the polypeptide of the invention which binds to the N- or C-terminus end. Said peptide is thus capable of binding one or more ligands of an affinity matrix, such as an affinity chromatography. One example of said peptide is the histidine tag (His-tag) which can contain six histidine residues (His6 or H6), which can bind to a nickel or cobalt column with high affinity. Other examples of said peptides include, but are not limited to, Arg-tag, FLAG-tag, Strep-tag, an epitope capable of being recognized by an antibody, such as c-myc-tag (recognized by an anti-c-myc antibody), SBP-tag, S-tag, calmodulin-binding peptide, cellulose-binding domain, chitin-binding domain, glutathione S-transferase-tag, maltose-binding protein, NusA, TrxA, DsbA, Avi-tag, etc. (Terpe K., Appl. Microbiol. Biotechnol. (2003), 60:523-525).

The term "nuclear signaling peptide", as used in the present invention, or NLS refers to a sequence directing the polypeptide to which it binds to the nucleus. Cellular localization sequences suitable for transporting the polypeptide of the invention to the nucleus comprise both sequences which act irrespective of external activators and sequences which can be activated externally in which case the cell comprising the polypeptide is contacted with a compound capable of activating the nuclear signaling sequence. NLS sequences not requiring an activator to promote protein translocation are widely known by the person skilled in the art and include all those sequences capable of being recognized by the heterodimeric receptor formed by alpha and beta importin, they form a complex which is recognized by the nuclear pore and is translocated through said pore through a process in which GTP pyrolysis occurs. One type of NLS is that formed by a shot basic amino acid region, such as the SV40 virus large T-antigen NLS formed by the sequence PKKKRKV (SEQ ID NO:57), which has also been shown to be effective in mammalian cells. Another type of NLSs is that which is formed by a bipartite sequence formed by two basic amino acid regions separated by a spacer of 10 to 12 amino acids, such as the Nucleoplasmin NLS formed by the sequence KRPAATKKAGQAKKKK (SEQ ID NO:58). A third type of NLS is that which is similar to the homeodomain of S. cerevisiae MATα2 protein or of c-myc protein, formed by the sequences PAAKRVKLD (SEQ ID NO:59) and RQRRNELKRSF (SEQ ID NO:60) in which a particular accumulation of basic amino acids is not seen. Other examples of NLS include the sequence NQSSNFGP-MKGGNFGGRSSGPYGGGGQYFAKPRNQGGY (SEQ ID NO:61) of hRNPA1 M9 protein, the sequence RMRK-FKNKGKDTAELRRRRVEVSVELRKAKKDEQ-ILKRRNV (SEQ ID NO:62) of alpha importin IBB domain, the sequences VSRKRPRP (SEQ ID NO:63) and PPK-KARED (SEQ ID NO:64) of myoma T-protein, the sequence of human p53 protein, the sequence SALIKKK-KKMAP (SEQ ID NO:65) of mouse c-abl IV protein, the sequences DRLRR (SEQ ID NO:66) and PKQKKRK (SEQ ID NO:67) of influenza virus NS1 protein, the sequence RKLKKKIKKL (SEQ ID NO:68) of hepatitis virus deltan antigen, the sequence REKKKFLKRR (SEQ ID NO:69) of the mouse Mx1 protein, the sequence KRKGDEVDGVDE-VAKKKSKK (SEQ ID NO:70) of poly(ADP-ribose) polymerase, the sequence RKCLQAGMNLEARKTKK (SEQ ID NO:71) of human steroid hormone receptors and the NLS sequence of avian reovirus p17 protein (IAAKRGRQLD—SEQ ID NO:72). Additionally, the invention contemplates the use of NLS such as those described in US2006121513 and WO05120588 as well as of substituents of the type described in EP1695717 which allow transporting proteins containing them through the nuclear membrane.

In a particular embodiment, the polypeptide of the invention is fused to a polypeptide comprising herpesvirus VP16 protein and SV40 T-antigen NLS.

In a preferred embodiment, the polypeptide of the invention comprises a nuclear signaling peptide and specifically the SV40 virus large T-antigen NLS formed by the sequence PKKKRKV.

Regions of the muNS Protein which are Specifically and Efficiently Recruited into the Inclusions Formed by muNS or by muNS-Mi The authors of the present invention have identified the regions of the muNS protein of avian origin determining the capacity of said protein to be incorporated into the muNS inclusions appearing in cells in which said protein is expressed. Specifically, the authors of the present invention have observed that the region of muNS which best incorporates into the inclusions is the Intercoil region (477-542), while the C-Tail region (605-635) does not seem to participate in the monomer-monomer interactions and the two coiled-coil (Coil 1 and Coil 2) do seem to participate in same but with a lower affinity/specificity than the Intercoil. They have also identified an additional region (residues 381-448) which is also incorporated with high affinity into the inclusions of whole protein, but not into the inclusions formed by muNS-Mi, such as shown in Example 3.

This finding allows using said regions to "tag" proteins and enhance their integration into cytoplasmic inclusions generated by muNS, muNS-Mi or its respective fusions with the green fluorescent protein (GFP) to aid their tracking.

Therefore, in a second aspect, the invention relates to a fusion protein, hereinafter, fusion protein of the invention, comprising:

(i) a first component containing at least one polypeptide of interest; and
(ii) a second component selected from the group of:
  a polypeptide comprising sequence 381-448 (SEQ ID NO: 2) of avian Orthoreovirus muNS protein or the corresponding sequence of mammalian Orthoreovirus muNS protein or a functionally equivalent variant of any of the above;
  a polypeptide comprising sequence 448-477 (SEQ ID NO: 3) of avian Orthoreovirus muNS protein or the corresponding sequence of mammalian Orthoreovirus muNS protein or a functionally equivalent variant of any of the above;
  a polypeptide comprising sequence 477-542 (SEQ ID NO: 4) of avian Orthoreovirus muNS protein or the corresponding sequence of mammalian Orthoreovirus muNS protein or a functionally equivalent variant of any of the above; and
  a polypeptide comprising sequence 539-605 (SEQ ID NO: 5) of avian Orthoreovirus muNS protein or the corresponding sequence of mammalian Orthoreovirus muNS protein or a functionally equivalent variant of any of the above.

wherein the second component does not contain a polypeptide comprising the amino acids of mammalian Orthoreovirus muNS protein corresponding to sequence 605-635 (SEQ ID NO: 6) of said avian protein.

The term "fusion protein", as used in the present invention, refers to polypeptides comprising two or more regions originating from different or heterologous proteins.

The term "avian Orthoreovirus muNS or μNS protein", as used in the present invention, refers to one of the non-structural proteins encoded by the M3 gene of avian reovirus or avian Orthoreovirus and is the only protein of the avian reovirus capable of forming inclusions when expressed in the absence of other viral factors (Touris-Otero et al. Virology, 319; 94-106). It is a protein of 635 amino acids defined by the accession number AY608700 in the NCBI database (SEQ ID NO:56).

The term "mammalian Orthoreovirus muNS or μNS protein", as used in the present invention, refers to one of the non-structural proteins encoded by mammalian reovirus or mammalian Orthoreovirus and is the only protein of the mammalian reovirus capable of forming inclusions when expressed in the absence of other viral factors (Becker, M. M. et al. 2003. J. Virol. 77:5948-5963). It is a protein of 721 amino acids defined by the accession number ABP48918 in the NCBI database (SEQ ID NO:55).

The term "mammalian Orthoreovirus", as used in the present invention, refers to one of the twelve genera belonging to the Reoviridae virus family and specifically to the group within the genus infecting mammals. They have dsRNA genomes and are therefore group III viruses.

The term "avian Orthoreovirus" has already been defined in the preceding section, therefore reference is made to said section.

Additionally, the two components of the fusion protein can be connected by a peptide the sequence of which contains a protease cleavage target, thus allowing the separation of the two components. The protease cleavage sites suitable for incorporation in the fusion protein of the invention include enterokinase (cleavage site DDDDK—SEQ ID NO:73), Xa factor (cleavage site IEDGR—SEQ ID NO:74), thrombin (cleavage site LVPRGS—SEQ ID NO:75), protease TEV (cleavage site ENLYFQG—SEQ ID NO:76), protease PreScission (cleavage site LEVLFQGP—SEQ ID NO:77), inteins and the like.

The first component of the fusion protein is made up of a polypeptide of interest. "Polypeptide of interest" is understood as any polypeptide to be included in the form of a fusion protein. In a particular embodiment, said polypeptide of interest can be a viral antigen, a bacterial antigen, a fungal antigen, an allergen or environmental antigen or a tumor antigen.

Viral antigens suitable as the first component of the fusion protein of the invention include the antigens of HIV-1, (such as tat, nef, gp120 or gp160, gp40, p24, gag, env, vif, vpr, vpu, rev), human herpes virus, (such as gH, gL, gM, gB, gC, gK, gE or gD or derivatives thereof) or immediate early protein such as ICP27, ICP47, ICP4, ICP36 of VHS1 or VHS2, cytomegalovirus, especially human cytomegalovirus, (such as gB or derivatives thereof), Epstein Barr virus (such as gp350 or derivatives thereof), varicella zoster virus (such as gpI, II, III and IE63), or of a hepatitis virus such as hepatitis B virus (for example surface antigen of hepatitis B or nuclear antigen of hepatitis), hepatitis C virus (for example nuclear antigens, E1, NS3 or NS5), of paramyxovirus such as respiratory syncytial virus (such as proteins F and G or derivatives thereof), of parainfluenza virus, of rubella virus (such as proteins E1 and E2), measles virus, mumps virus, human papilloma virus (for example HPV6, 11, 16, 18, LI, L2, E1, E2, E3, E4, E5, E6, E7), flavivirus (for example yellow fever virus, dengue virus, tick-borned encephalitis virus, Japanese encephalitis virus) or influenza virus-infected cells, such as proteins HA, NP, NA or M, or combinations thereof), rotavirus antigens (such as VP7sc and other rotavirus components), and the like (see Fundamental Virology, second edition, eds. Fields, B. N. and Knipe, D. M. (Raven Press, New York, 1991) for additional examples of viral antigens).

Bacterial antigens suitable as the first component of the fusion protein of the invention include antigens of *Neisseria* spp., including *N. gonorrhea* and *N. meningitidis* (transferrin-binding proteins, lactoferrin-binding proteins, PilC and adhesins); antigens of *S. pyogenes* (such as M proteins or fragments thereof and C5A protease); antigens of *S. agalactiae, S. mutans; H. ducreyi; Moraxella* spp including *M. catarrhalis*, also known as *Branhamella catarrhalis* (such as high and low molecular weight invasins and adhesins); antigens of *Bordetella* spp, including *B. pertussis* (for example *Parapertussis* and *B. bronchiseptica* (such as pertactin, tetanus toxin or derivatives thereof, filamentous hemagglutinin, adenylate cyclase, fimbriae); antigens of *Mycobacterium* spp., including *M. tuberculosis, M. bovis, M. leprae, M. avium, M. paratuberculosis, M. smegmatis; Legionella* spp, including *L. pneumophila*; (for example ESAT6, antigen 85A, -B or -C, MPT 44, MPT59, MPT45, HSPIO, HSP65, HSP70, HSP 75, HSP90, PPD of 19 kDa [Rv3763], PPD of 38 kDa [Rv0934]); antigens of *Escherichia* spp, including enterotoxic *E. coli* (for example colonization factors, thermolabile toxin or derivatives thereof, heat stable toxin or derivatives thereof), antigens of enterohemorrhagic *E. coli* and enteropathogenic *E. coli* (for example shiga toxin-like toxin or derivatives thereof); antigens of *Vibrio* spp, including *V. cholera* (for example cholera toxin or derivatives thereof); antigens of *Shigella* spp, including *S. sonnei, S. dysenteriae, S. flexnerii; Yersinia* spp, including *Y. enterocolitica* (for example a Yop protein); antigens of *Y. pestis, Y. pseudotuberculosis; Campylobacter* spp, including *C. jejuni* (for example toxins, adhesins and invasins); antigens of *Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); antigens of *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof); antigens of *C. botulinum* (for example botulinum toxin and derivative thereof), antigens of *C. difficile* (for example clostridium toxins A or B and derivatives thereof); antigens of *Bacillus* spp., including *B. anthracis* (for example anthrax toxin and derivatives thereof); *Corynebacterium* spp., including *C. diphtheriae* (for example diphtheria toxin and derivatives thereof); antigens of *Borrelia* spp., including *B. burgdorferi* (for example OspA, OspC, DbpA, DbpB); antigens of *B. garinii* (for example OspA, OspC, DbpA, DbpB), *B. afzelii* (for example OspA, OspC, DbpA, DbpB), antigens of *B. andersonfi* (for example OspA, OspC, DbpA, DbpB), antigens of *B. hermsii; Ehrlichia* spp., including *E. equi* and the human granulocytic ehrlichiosis agent; *Rickettsia* spp, including *R. rickettsii; Chlamydia* spp., including *C. trachomatis* (for example MOMP, heparin-binding proteins); antigens of *Chlamydia pneumoniae* (for example MOMP, haparin-binding proteins), antigens of *C. psittaci; Leptospira* spp., including *L. interrogans; Treponema* spp., including *T. pallidum* (for example the uncommon outer membrane proteins), antigens of *T. denticola, T. hyodysenteriae; Toxoplasma* spp. and *T. gondii* (for example SAG2, SAGS, Tg34); antigens of *M. tuberculosis* (such as Rv2557, Rv2558, RPFs: Rv0837c, Rv1884c, Rv2389c, Rv2450, Rv1009, aceA (Rv0467), PstS1, (Rv0932), SodA (Rv3846), Rv2031c of 16 kDal, Tb Ra12, Tb H9, Tb Ra35, Tb38-1, Erd 14, DPV, MTI, MSL, mTTC2 and hTCC1); antigens of *Chlamydia* (such as the high molecular weight protein (HWMP), ORF3 (document EP 366 412) and possible membrane proteins (Pmp); antigens of *Streptococcus* spp, including *S. pneumoniae* (PsaA, PspA, streptolysin, cholinebinding proteins, the pneumolysin protein antigen, and detoxified mutant derivatives thereof); antigens derived from *Haemophilus* spp., including *H. influenzae* type B (for example PRP and conjugates thereof); antigens of nonclassifiable *H. influenzae* (such as OMP26, high molecular weight adhesins, P5, P6, D protein and D lipoprotein, and fimbrin and fimbrin-derived peptides, or multiple copy variants or the fusion proteins thereof).

Fungal antigens suitable as the first component of the fusion protein of the invention include, but not limited to, for example, fungal antigenic components of *Candida*; fungal antigens of *Histoplasma* such as heat shock protein 60 (HSP60) and other fungal antigenic components of *Histoplasma*; of *Pneumocystis* spp., including *P. carinii*; fungal antigens of cryptococci such as capsular polysaccharides and other fungal antigenic components of cryptococci; fungal antigens of coccidia such as spherule antigens and other fungal antigenic components of coccidia; antigens of *Candida* spp., including *C. albicans*; of *Cryptococcus* spp., including *C. neoformans*; and fungal antigens of *Tinea* such as tricophitin and other fungal antigenic components of coccidia.

Prokaryotic antigens suitable as the first component of the fusion protein of the invention include, but not limited to, antigens of *Plasmodium* spp., such as *P. falciparum* and antigens derived from *Plasmodium falciparum* (such as RTS.S, TRAP, MSP1, AMA1, MSP3, EBA, GLURP, RAP1, RAP2, sequestrin, PfEMP1, Pf332, LSA1, LSA3, STARP, SALSA, PfEXP1, Pfs25, Pfs28, PFS27/25, Pfs16, Pfs48/45, Pfs230 and the analogs thereof in *Plasmodium* spp.); as well as merozoite surface antigens, sporozoite surface antigens, circumsporozoite antigens, gametocyte/gamet surface antigens, blood type antigen pf, 55/RESA and other plasmoid antigenic components; antigens of *Toxoplasma* such as SAG-I, p30 and other antigenic components of *Toxoplasma*; schistosome antigens such as glutathione-S-transferase, paramyosin and other schistosome antigenic components; the antigen of *Trichomonas* spp., including *T. vaginalis*; antigens of *Entamoeba* spp., including *E. histolytica; Babesia* spp., including *B. microti*; the antigen of *Leishmannia* and other antigens of *Leishmania* such as gp63, lipophosphoglycan and their associated-protein and other antigenic components of *Leishmania*; antigens of *Giardia* spp., including *G. lamblia*; and antigens of *Trypanosoma cruzi* such as the 75-77-kDa antigen, the 56 kDa-antigen and other antigenic components of *Trypanosoma*.

Allergens or environmental antigens suitable as the first component of the fusion protein of the invention include, but not limited to, an antigenderived from allergens produced naturally such as pollen allergens (pollen allergens of trees, herb, undergrowth and grass), insect allergens (inhaled allergens, allergens from saliva and from posion), allergens from the dander and hair of animals, and food allergens. Important pollen, tree, grass and herb allergens originate from taxonomic ordes of Fagales, Oleales, Pinales and Platanaceae including among other birch (*Betula*), alder (*Alnus*), hazel (*Corylus*), hard beam (*Carpinus*) and olive (*Olea*), cedar (*Cryptomeria* and *Juniperus*), banana (*Platanus*), the order of Poales including, among others, grasses of the genera *Lolium, Phleum, Poa, Cynodon, Dactylis, Holcus, Phalaris, Secale* and *Sorghum*, the orders of Asterales and Urticales including among others herbs of the genera *Ambrosia, Artemisia* and *Parietaria*. Other allergenic antigens which can be used include the allergens from house dust mites of the genera *Dermatophagoides* and *Euroglyphus*, storage mites for example *Lepidoglyphys, Glycyphagus* and *Tyrophagus*, allergens from cockroaches, midges and fleas for example *Blatella, Periplaneta, Chironomus* and *Ctenocephalides*, allergens from mammals such as cat, dog and horse, birds, allergens from poison including those originating from bites or stings of insects such as those of the taxonomic order of Hymenoptera including bees (superfamily Apidae), wasps and ants (superfamily Formicoidae). Other allergenic antigens which can be used include allergens from the inhalation of fungi such as those of the genera *Alternaria* and *Cladosporium*.

Tumor antigens suitable as the first component of the fusion protein of the invention include, but are not limited to, MAGE, MART-1/Melan-A, gp100, dipeptidyl peptidase IV (DPPIV), adenosine deaminase-binding protein (ADAbp), cyclophin b, colorrectal-associated antigen (CRC)-0017-1A/GA733, carcinoembryonic antigen (CEA) and its antigenic epitopes CAP-1 and CAP-2, etv6, aml1, prostate-specific antigen (PSA) and its antigenic epitopes PSA-1, PSA-2, and PSA-3, prostate-specific membrane antigen (PSMA), T-cells/CD3-ζ strand receptor, MAGE family of tumor antigens (for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE family of tumor antigens (for example, GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, 13-catenin, γ-catenin, pl2Octn, gp100Pme1117, PRAME, NY-ESO-1, cdc27, adenomatous colon polyposis (ACP) protein, fodrin, conexin 37, Ig idiotype, p15, gp75, gangliosides GM2 and GD2, viral products such as proteins of the human papillomavirus, Smad family of tumor antigens, lmp-1, PIA, EBV encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2, acute lymphoblastic leukemia (etv6, aml1, cyclophin b), B-cells lymphoma (Ig idiotype), glioma (E-cadherin, a-catenin, 13-catenin, 7-catenin, p120ctn), bladder cancer (p21ras), gall bladder cancer (p21ras), breast cancer (family MUC, HER2/neu, c-erbB-2), uterine cervix carcinoma (p53, p21ras), colon carcinoma (p21ras, HER2/neu, c-erbB-2, family MUC), colorrectal cancer (colorrectal-associated antigen (CRC)-0017-1A/GA733, ACP), coriocarcinoma (CEA), epithelial cell cancer (cyclophin b), stomach cancer (HER2/neu, c-erbB-2, glycoprotein ga733), hepatocellular cancer, Hodgkins's lymphoma (lmp-1, EBNA-1), lung cancer (CEA, MAGE-3, NY-ESO-1), lymphoid cell-derived leukemia (cyclophin b), melanoma (protein p15, gp75, oncofetal antigen, gangliosides GM2 and GD2, Melan-A/MART-1, cdc27, MAGE-3, p21ras, gp100Pme1117). myeloma (family MUC, p21ras), non-small cell lung carcinoma (HER2/neu, c-erbB-2), nasopharyngeal cancer (lmp-1, EBNA-1), ovarian cancer (family MUC, HER2/neu, c-erbB-2), prostate cancer (prostate-specific antigen (PSA) and its antigenic epitopes PSA-1, PSA-2 and PSA-3, PSMA, HER2/neu, c-erbB-2, glycoprotein ga733), kidney cancer (HER2/neu, c-erbB-2), uterine cervix and esophageal squamous cell cancers (viral products such as proteins of the human papillomavirus), testicular cancer (NY-ES0-1) and T-cell leukemia (epitopes of HTLV-1).

The second component of the fusion protein can be selected from the group:
- a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
- a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
- a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
- a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

However, the second component cannot contain a polypeptide comprising the amino acids of mammalian *Orthoreovirus* muNS protein corresponding to sequence 605-635 (SEQ ID NO: 6) of said avian protein.

The polypeptides forming part of the second component may correspond to several fragments of the avian *Orthoreovirus* muNS protein (381-448, 448-477 (Coil 1 or C1), 477-542 (Intercoil) or 539-605 (Coil 2 or C2)) or to the corresponding sequence of the mammalian *Orthoreovirus* muNS protein. Said fragments of the muNS protein are capable of directing the first component, i.e., the polypeptide of interest, to the inclusions, since they interact specifically with other muNS proteins. For the purpose of determining the corresponding sequence of the mammalian *Orthoreovirus* muNS protein with respect to said fragments of avian Orthoreovirus muNS protein, the sequence of the avian muNS protein and the sequence of the muNS mammalian protein can be aligned. Said sequence alignment can be carried out by means of conventional methods known by the person skilled in the art. Optimum sequence alignments can be carried out, for example, with the local homology algorithm of Smith and Waterman (Adv. Appl. Math., 1981, 2:482), with the alignment algorithm for homology of Needleman and Wunsch, (J. Mol. Biol., 1970, 48:443), by the search for similarity with the method of Pearson and Lipman, (Proc. Natl Acad. Sci. USA, 1988, 85:2444), by computerized implementation of these algorithms (GAP, BESTFIT, FASTA, and TFASTA in the Wisconsin Genetics Software Package, Genetics Computer Group, 575 Science Dr., Madison, Wis.), or by manual alignment and visual inspection (Current Protocols in Molecular Biology (Ausubel et. al., eds. 1995 supplement).

The polypeptides forming part of the second component can relate to functionally equivalent variants of the mentioned fragments of the muNS protein of an *Orthoreovirus*. "Functionally equivalent variant" is understood as all those peptides derived from the muNS sequence by means of modifying, inserting and/or deleting one or more amino acids, provided that the function of the muNS proteins mentioned previously is substantially maintained. Specifically, the functionally equivalent variant shows at least one function related to the capacity to be incorporated into the inclusions formed by the complete protein or muNS-Mi in a cell. Methods suitable for determining the capacity to be incorporated into the inclusions includes, but is not limited to the method described in Example 3 of the present invention based on the formation of the inclusions and the expression of the protein of interest in the form of fusion protein associated with the fragments directing it to the inclusions. Indirect immunofluorescence would be carried out subsequently using polyclonal antibodies specific against HA epitope or the epitope of interest, the incorporation of said fragments into the inclusions being able to be confirmed. Variants suitable for use in the present invention include those showing at least 25%, at least 40%, at least 60%, at least 70%, at least 80%, at least 90%, at least 95%, at least 96%, at least 97%, at least 98% or at least 99% of sequence identity with respect to the muNS sequences indicated above. The degree of identity between two amino acid sequences can de determined by conventional methods, for example, by means of basic sequence alignment algorithms known in the state of the art, such as, for example BLAST (Altschul S. F. et al. Basic local alignment search tool. J Mol Biol. 1990 Oct. 5; 215(3):403-10). The person skilled in the art will understand that the amino acid sequences referred to in this description can be chemically modified, for example, by means of physiologically relevant chemical modifications, such as, phosphorylations, acetylations, etc.

In a particular embodiment, the fusion protein of the invention additionally comprises a component selected from the group of a peptide to facilitate its purification and a nuclear signaling peptide. Said component has been previously defined in the section of "Minimum region of muNS protein capable of forming inclusions", therefore reference is made to said description.

In a particular embodiment, the fusion protein of the invention comprises a nuclear signaling peptide for the purpose of directing the fusion protein to the nucleus.

Likewise, in another aspect, the invention relates to a polynucleotide encoding said fusion protein and a cell comprising the polypeptide or the polynucleotide.

The cell which can be used for carrying out this aspect has been described for the first aspect of the invention, therefore reference will be not be made to same in this aspect.

Kit of the Invention

The invention also provides kits which are suitable for putting the method of the invention into practice. Therefore, in another aspect, the invention relates to a kit, hereinafter kit of the invention, comprising:

(i) a first component selected from the group of:
  (a) a polynucleotide encoding the muNS protein of an *Orthoreovirus* or a functionally equivalent variant;
  (b) a polynucleotide encoding a polypeptide comprising amino acids 448-635 (SEQ ID NO:1) of avian *Orthoreovirus* muNS protein or the corresponding sequence of mammalian *Orthoreovirus* muNS protein or a functionally equivalent variant of any of the above; and
  (c) a cell expressing the muNS protein of an *Orthoreovirus* or a polypeptide comprising amino acids 448-635 (SEQ ID NO:1) of said protein or the corresponding sequence of mammalian *Orthoreovirus* muNS protein or a functionally equivalent variant of any of the above; and (ii) a second component selected from the group of:
  (a) a polynucleotide encoding a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
  (b) a polynucleotide encoding a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
  (c) a polynucleotide encoding a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
  (d) a polynucleotide encoding a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

As used herein, the term "kit" refers to a combination of components facilitating a process, method, assay, analysis or handling of a sample. These kits provide the materials necessary for carrying out the methods described in the present invention.

The kit of the invention comprises a first component which is selected from a polinucleotide encoding the complete muNS protein or the fragment of said protein capable of forming inclusions. Likewise, the kit can comprise the cell expressing the complete protein or the fragment of said protein capable of forming inclusions as the first component. The kit comprises one of the fragments capable of directing the protein to the inclusions, including the following fragments of the avian muNS protein: 381-448, 448-477, 477-542 and 539-605, as the second component.

Additionally, the kit of the invention can comprise a cell suitable for putting the kit into practice. Said cell can be a prokaryotic cell or a eukaryotic cell. Practically any host cell which can be transformed with the polynucleotide of the invention, or which can be transformed, transfected or infected by a recombinant vector containing the polynucleotide of the invention, for example animal cells (such as mammalian cells, bird cells, insect cells, etc.), plant cells, yeasts, etc., can be used in the kit of the invention. The cells of the invention can be obtained by means of conventional methods known by the persons skilled in the art [Sambrook et al., Cold Spring Harbor Laboratory Press, third edition, 2001].

Therapeutic Uses of the Fusion Protein of the Invention

In another aspect, the invention thus relates to a fusion protein for use in medicine, comprising:
(i) a first component containing at least one polypeptide of interest; and
(ii) a second component selected from the group of:
  a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
  a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
  a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
  a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

The fusion protein comprises a first component containing at least one polypeptide of interest. Possible polypeptides of interest have been described for the second aspect of the invention, specifically for the fusion protein of the invention of the present specification, therefore reference is made to those already described. The second component is selected from a polypeptide comprising sequence 381-448 (SEQ ID NO: 2) of avian *Orthoreovirus* muNS protein, a polypeptide comprising sequence 448-477 (SEQ ID NO: 3), a polypeptide comprising sequence 477-542 (SEQ ID NO: 4), a polypeptide comprising sequence 539-605 (SEQ ID NO: 5), or the corresponding sequences of mammalian *Orthoreovirus* muNS protein or a functionally equivalent variant of any of the above.

The use in medicine of the fusion protein includes diseases such as those caused by viral infections if it is a viral antigen, diseases caused by bacterial infections if it is a bacterial antigen, diseases caused by fungal infections if it is a fungal antigen, allergies if it is an allergen, diseases caused by a parasitic infestation if it is a parasitic antigen and/or a tumor if it is a tumor cell-specific antigen.

Diseases caused by viral infections which can be treated with the fusion protein include, without limitation, diseases caused by the infections by HIV-1 virus (AIDS), by human herpesviruses such as the herpes simplex virus (herpes simplex, herpes genitalis), cytomegalovirus (mononucleosis, retinitis, hepatitis), the Epstein Barr virus (infectious mononucleosis, Burkitt's lymphoma and nasopharyngeal carcinoma) and varicella zoster virus (varicella, herpes zoster); by the hepatitis virus such as hepatitis B virus or hepatitis C virus, by paramyxovirus such as respiratory syncytial virus, parainfluenza virus, rubella virus, measles virus, mumps virus, human papillomavirus; flavivirus such as yellow fever virus, dengue virus, tick-borne encephalitis virus or Japanese encephalitis virus) and rotavirus. Other types of viral infections which can be treated are described in detail in Fundamental Virology, second edition, eds. Fields, B. N. and Knipe, D. M. (Raven Press, New York, 1991).

Diseases caused by bacterial infections which can be treated with the fusion protein include, without limitation, diseases caused by microorganisms of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Heamophilus* or *Bordetella*.

Diseases caused by fungal infections which can be treated with the fusion protein include, without limitation, candidiasis, aspergillosis, histoplasmosis, cryptococcal meningitis and the like.

Parasitic infestations which can be treated with the fusion protein include, without limitation, malaria, *Pneumocystis jiroveci* infection, pneumonia, sleeping sickness, leishmaniasis, cryptosporidiosis, toxoplasmosis and tripanosoma.

Allergic disorders which can be treated with the fusion protein include, without limitation, allergies caused by pollen exposure (pollen allergens of trees, herb, undergrowth and grass), allergies caused by exposure to insect allergens (inhaled allergens, allergens from saliva and from position), allergens from the dancer and hair of animals and food allergens.

The fusion protein is also suitable for the treatment of hyperproliferative diseases. As used in the present invention, the expression "proliferative disease" refers to diseases which are caused by or resulted from inappropriately high levels of cell division, from inappropriately low levels of apoptosis or from both and includes both primary tumors and metastasis. The term "primary tumor" refers to a tumor which is in the primary site in which said tumor originate. As used in the present invention, the term "metastasis" refers to the process through which a tumor spread to body tissues different from the primary site of the tumor origin.

In the context of the invention, "treatment of a hyperproliferative disease" or "treatment of a tumor" is understood as the administration of the fusion protein to prevent or delay the onset of symptoms, complications or biochemical indications of the cancer or tumor, to ease its symptoms or to stop and inhibit its development and progress such as, for example, the onset of metastasis. The treatment can be a prophylacyic treatment to delay the onset of the disease or to prevent the manifestation of its clinical or subclinical symptoms or a therapeutic treatment to eliminate or ease the symptoms after the manifestation of the disease or in relation with its surgical treatment or with radiotherapy.

The fusion protein can also be used as a vaccine, since exogenous proteins can be integrated in the inclusions and the inclusions can be purified. The purified inclusions form a particulate material and it has been shown that the exposed epitopes in the particulate material stimulate immune response (Roy, P., 1996. Intervirology 39: 62-71), both cellular immune response and humoral immune response more effectively than the soluble isolated proteins. Therefore, the fusion protein of the invention can be used for generating particles exposing various epitopes of medical or veterinary interest and can thus be used as vaccines. The advantages would be: i) they are formed by particulate material; ii) ease of production and purification; iii) biologically safe since it does not use live pathogenic virus but its protein components and iv) different multiple epitopes can be exposed in the same particle. Therefore, different immunogenic epitopes of the same virus or different epitopes of different virus or of different serotypes, which would aid in improving the efficacy of the generated vaccines can be integrated in the same inclusions.

Therefore, in another aspect, the invention relates to the use of a fusion protein for preparing a drug to stimulate a subject's immune response.

The fusion protein of the invention is preferably used for the treatment of a disease requiring an activation of the immune system in response to an antigen.

Alternatively, the invention relates to a fusion protein for use in the stimulation of a subject's immune response.

Alternatively, the invention relates to a method for enhancing the stimulation of a subject's immune response to an antigen or for the treatment of a disease requiring an activation of the immune system comprising the administration of a fusion protein to said subject.

The expression "stimulation of a subject's immune response", as used in the present invention, refers to the start of an immune response against a specific antigen in an individual in whom said response takes place for the first time as well as the reactivation of the immune response in subjects in who said immune response already took place. It is understood that the immune response can involve both an innate immune response and an adaptative immune response and it can involve a humoral or cellular type response.

The term "vaccine", as used in the present invention, refers to a composition comprising at least one antigen of interest and which allows activating a subject's immune response to said antigen. The objective of the vaccines is to activate cell-mediated immunity and antibody-mediated immunity.

Therefore, the vaccines which can be used in the invention include vaccines having one or more antigens selected from the group of a viral antigen, a bacterial antigen, a fungal antigen, an allergen or a environmental antigen and a tumor antigen which have been described previously where the polypeptides of interest which can be included in the fusion protein were mentioned.

Method for Incorporating the Proteins of Interest into Inclusions Formed by the muNS Protein The authors of the present invention have clearly shown that the tagging of proteins with specific domains of the muNS protein forms an efficient method for directing exogenous proteins to the cytoplasmic inclusions generated by the muNS protein without causing the dismantling of the inclusions. Specifically, the Intercoil domain (muNS(477-542)) is the most suitable for performing said tagging since it is small enough as not to alter the nature of the protein of interest and it is more efficiently incorporated into the muNS inclusions. Therefore, such as seen in Example 3 and in FIGS. 4 and 5, right panels, 3 and 5, said domain is capable of directing both the HA epitope and the green fluorescent protein (GFP) to the muNS protein inclusions. In addition to not affecting the integrity of the muNS inclusions, the recruited protein (GFP) is perfectly folded and is active and functional since it continues to emit its characteristic fluorescence. Likewise, the domains Coil 1, Coil 2 and muNS (381-448) can also be used for directing proteins to the muNS inclusions. Therefore it has been shown that this tagging can be used in different applications such as: i) to sequestrate proteins in the inclusions; ii) to purify active proteins simply; iii) to detect of intracellular protein-protein interactions.

Therefore, in another aspect, the invention relates to the use of a fusion protein comprising:

(i) a first component containing at least one polypeptide of interest; and
(ii) a second component selected from the group of:
a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;

for incorporating the first component into the inclusions resulting from the cell expression of the polypeptide comprising amino acids 448 to 635 (SEQ ID NO: 1) of avian *Orthoreovirus* muNS protein or the corresponding amino acids of mammalian *Orthoreovirus* or the complete avian or mammalian *Orthoreovirus* muNS protein or a functionally equivalent variant of any of the above.

In a preferred embodiment, the use of the fusion protein of the invention is carried out using as a second component of the fusion protein a polypeptide comprising amino acids 381-448 (SEQ ID NO: 2) of avian *Orthoreovirus* muNS protein or the corresponding amino acids of mammalian *Orthoreovirus*, in which case the inclusions are inclusions resulting from complete avian or mammalian *Orthoreovirus* muNS protein or a functionally equivalent variant of any of the above and not those of the polypeptide comprising amino acids 448 to 635 (SEQ ID NO: 1) of avian *Orthoreovirus* muNS protein or the corresponding amino acids of mammalian *Orthoreovirus*.

Methods of Purifying Inclusions Formed by the muNS Protein or by the Minimum Region of Said Protein The inclusions generated by the expression of the complete avian or mammalian *Orthoreovirus* muNS protein or by the polypeptide comprising amino acids 448 to 635 (SEQ ID NO: 1) of avian *Orthoreovirus* muNS protein or the corresponding amino acids of mammalian *Orthoreovirus* or a functionally equivalent variant of any of the above can be easily purified by means of the method described in the section of "Methods" of the Examples, such as shown in Example 1 and in Example 6.

Therefore, in another aspect, the invention relates to a method for purifying the inclusions formed by a polypeptide selected from the group: polypeptide comprising amino acids 448-635 (SEQ ID NO: 1) of avian *Orthoreovirus* muNS protein, the corresponding amino acids of mammalian *Orthoreovirus* muNS protein, the complete avian or mammalian *Orthoreovirus* muNS protein and a functionally equivalent variant of any of the above comprising:

(a) expressing said polypeptide in a cell and maintaining said cell in conditions suitable for inclusion formation; and
(b) purifying said the inclusions.

In a first step, the method of purifying the inclusions formed by the muNS protein or by the minimum region of said protein according to the invention comprises generating the inclusions in a cell, for which it is necessary to introduce the polynucleotide suitable for the expression of said proteins into said cell or if, in contrast, said polynucleotide is already present in the cell, putting the cell in conditions suitable for the expression of said polynucleotide.

In a preferred embodiment, the polypeptide which is expressed in the first step comprises amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above and maintaining said cell in conditions suitable for inclusion formation.

The DNA construct encoding the protein capable of forming inclusions can be introduced into host cells using well known techniques such as infection, transduction, transfection, transvection, electroporation and transformation. Such methods are described in many standard laboratory manuals, such as Davis et al., *Basic Methods in Molecular Biology* (1986). The vector can be, for example, a phage, a plasmid, viral or retroviral vector. The cells comprising the gene construct may have been transitorily or stably transfected, for which the transfection of the gene construct is carried out simultaneously with a gene providing resistance to a specific antibiotic, such that those cell lines which have incorporated the DNA into the genome of those cell lines in which the DNA is in an extrachromosomal position can be selected. The gene which allows selecting the cells can be provided forming part of the same vector containing the construct object of the invention or, alternatively, can be provided separately by means of co-transfection with a second plasmid containing said resistance gene. The process of selecting cells containing some or all of the DNA constructs of the components of the first complex of the invention stably integrated in the genome is carried out by means of a conventional selection process (see for example Ausubel, F. M. et al., *Current Protocols in Molecular Biology* (1997) 9.5.1-9.5.19). To that end, the cells are transfected with the vector or mixtures of vectors and after a recovery period, they are left to grow in a selective medium (either a medium containing the antibiotic against which the reporter gene confers resistance or a minimum medium containing the antimetabolite against which the reporter gene confers resistance). The cell colonies growing in the selective medium are isolated and they are left to grow again in the selective medium.

For the purpose of successfully generating the inclusions in a cell, said cell must be maintained in suitable conditions so that the formation of inclusions is favored, such as the conditions described in Section "Culture Media" of the examples, for insect cells. A person skilled in the art would know what type of conditions are optimum for each cell type where the inclusions are expressed. The culture media and conditions suitable for producing the inclusions will be chosen; said culture media and conditions are widely known by the persons skilled in the art. The choice of said culture media and conditions will depend on the microorganism or cell line chosen for producing the inclusions.

For the purpose of checking if the inclusions have been suitably formed, the person skilled in the art would know what methods to be used. Methods suitable for determining if the inclusions have been generated include, but not limited to, the method described in Example 1 of the present invention based on the detection of inclusions in a cell by indirect immunofluorescence using polyclonal anti-muNS antibodies.

Once the inclusions are formed in the cell, the second step consists of purifying said inclusions. To that end, the first step would be cell lysis by sonication or by any other method known by the person skilled in the art. The inclusions are obtained in the pellet or precipitate after a centrifugation, which inclusions will subsequently be suspended in a suitable buffer. In a preferred embodiment, the method of purifying the inclusions is that described in Section "Methods" of the Examples.

Different protocols for purifying inclusion bodies are known. Typically, the purification of inclusion bodies involves extraction, separation and/or purification of inclusion bodies by means of disrupting bacterial cells, for example, by means of incubation in a buffer solution (preferably 50 mM Tris/HCl 50 mM pH 7.5, 50 mM NaCl 50 mM, 5 mM $MgCl_2$, 1 mM DTT, 0.1 mM ATP 0.1 mM and 1 mM 1 PMSF). The cell suspension can be lysed by means of several steps in a French press, by means of homogeneization using a Polytron, or by means of sonication. Other methods for the lysing bacteria are widely known for the person skilled in the art (see. Sambrook et al., supra; Ausubel et al., supra).

In another aspect, the invention relates to a method for solubilizing the inclusions formed by a polypeptide selected from the group containing avian *Orthoreovirus* muNS protein or mammalian *Orthoreovirus* muNS protein or of the polypeptide comprising amino acids 448 to 635 (SEQ ID NO: 1) of avian *Orthoreovirus* muNS protein or the corresponding amino acids of mammalian *Orthoreovirus* or a functionally equivalent variant of any of the above which comprises contacting said inclusions in a divalent cation-free medium. Said contacting can be carried out by means of sedimenting the inclusions followed by the resuspending same in a divalent cation-free medium, optionally preceded by one or several washing cycles. Alternatively, the inclusions can be carried to a divalent cation-free medium by means of using chelating agents which reduce the concentration of free divalent cations in the medium to the concentrations where the disassembling of the inclusions takes place. Chelating agents suitable for reducing the concentration of divalent cations to the concentrations at which the disassembling of the inclusions occur include, without limitation, EDTA, EDDS, EDDM, EDDG, DTPA, NTA, iminodiacetic acid (IDA), iminotriacetic acid (ITA), ethylenediamine (En), N,N'-diethylenediamine (Den), diethylenetriamine (DTN), diethylenetetraamine (Trien), triaminotriethylene amine, citric acid and propylenediamine.

Methods of Purifying Proteins of the Invention

The inclusions generated by the expression of complete avian or mammalian *Orthoreovirus* muNS protein or by the polypeptide comprising amino acids 448 to 635 (SEQ ID NO: 1) of avian *Orthoreovirus* muNS protein or the corresponding amino acids of mammalian *Orthoreovirus* or a functionally equivalent variant of any of the above, can be easily purified, therefore if a polypeptide of interest is selectively directed to said inclusions, said polypeptide of interest could also be simply and efficiently purified, such as shown in Example 6, wherein the GFP protein tagged with the Intercoil domain by means of binding this protein to the inclusions formed by muNS is purified. Furthermore, said purified proteins maintain their biological activity.

Therefore, in another aspect, the invention relates to a method for purifying a fusion protein comprising a polypeptide of interest from a composition containing said fusion protein which comprises:

(a) contacting the inclusions formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with a composition containing the fusion protein to be purified wherein said fusion protein comprises:
(i) a first component containing at least one polypeptide of interest and
(ii) a second component selected from the group of:
   a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
   a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
   a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
   a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above,
and maintaining in suitable conditions so that the inclusions interact with the second component of the fusion protein;
(b) purifying the complex formed between the inclusions and fusion protein; and
(c) separating the fusion protein from the inclusions.

The first purification method of the invention comprises a first step of contacting the previously mentioned inclusions together with composition containing said fusion protein.

Said inclusions can be generated by means of the cell expression of the polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above and subsequently maintaining said cell in conditions suitable for inclusion formation.

In the context of the second purification method of the invention, the term "composition comprising the fusion protein" is used to refer to the fact that the fusion protein is not pure and it can be part of a rather complex mixture which can include other proteins or cell complexes and can preferably be an extract or a cell lysate.

Likewise, the fusion protein comprising the polypeptide of interest can be expressed in the same cell containing the inclusions, in which case the interaction takes place in the cell itself. Alternatively it is possible to express the inclusions and fusion protein in different cells, in which case the contacting of both components in step (a) takes place by means of contacting the inclusions obtained in the first cell with a more or less purified extract of the second cell comprising the fusion protein.

The result of the first step of the purification method of the invention will be the formation of complexes between the polypeptide of interest and the inclusions through one of the regions described previously having affinity for the inclusions.

Once the complex between the inclusions and the polypeptide of interest has been formed, step (b) comprises purifying said complex. In the case in which the complex has been formed inside the cell upon expressing the two components of the method in a single cell, the purification of the inclusions first requires lysing the cells and releasing the complexes into the medium.

Once the complexes have been released into the medium, they are purified using conventional methods for purifying inclusion bodies, as has been described previously in the context of the method for purifying the inclusions of the invention.

Once a preparation of inclusion bodies incorporating the protein of interest is available, step (c) comprises separating the fusion protein from the inclusions. To that end, the inclusions can be solubilized using chaotropic agents such as, without limitation, urea (from 4 M to 8 M), formamide (at least 80% v/v) and guanidine hydrochloride (from 4 M to 8 M). Some solvents which are capable of solubilizing aggregates include, for example, SDS and formic acid even though their use is unsuitable due to the lack of immunogenicity and/or activity. Once protein bodies have been solubilized, the proteins can be recovered by means of removing (by means of dialysis, for example) or diluting the denaturing agent, the formation of immunologically or biologically active proteins thus being allowed. Likewise, the fusion protein can be separated from the inclusions in the presence of a hypotonic buffer using a NaCl concentration of about 0.5 M, obtaining the fusion protein in solution with a high purity. In a particular embodiment, said hypotonic buffer does not have divalent ions.

The two components of the fusion protein are separated once the inclusions are separated from the fusion protein. To that end, the first and second component of the fusion protein can be connected by a peptide the sequence of which contains a protease cleavage target. The protease cleavage sites suitable for incorporation in the polypeptides of the invention include enterokinase (cleavage site DDDDK), Xa factor (cleavage site IEDGR), thrombin (cleavage site LVPRGS), protease TEV (cleavage site ENLYFQG), protease PreScission (cleavage site LEVLFQGP), inteins and the like. A person skilled in the art would know the specific cleavage conditions of each of the proteases. In a preferred embodiment, the separation is carried out as has been described in Example 6 of the present invention.

The person skilled in the art knows the different methods for purifying the polypeptide of interest bound to the inclusions. Methods suitable for purifying said complex includes, but is not limited to, the protocol for purifying GFP-Intercoil in insect Sf9 cells infected with baculovirus described in Example 6 of the present specification. Primarily, the method consists of lysing the cells, sonicating the extract and purifying the inclusions with bound GFP-Intercoil in the pellet. For the purpose of checking if the purification has been successful, an electrophoresis could be carried out in denaturing conditions, checking that the polypeptide of interest is present in the extract after purification.

In another aspect the invention relates to a method for purifying a polypeptide comprising a protein of interest which comprises:
(a) expressing in a cell the polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above and maintaining said cell in conditions suitable for inclusion formation;
(b) expressing in said cell a fusion protein comprising:
 (i) a first component containing at least one polypeptide of interest; and
 (ii) a second component selected from the group of:
  a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
  a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
  a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
  a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.
in conditions suitable so that the inclusions generated in step (a) interact with the second component of the fusion protein; and wherein steps (a) and (b) are carried out in any order,
 (c) purifying the complex formed between the inclusions and fusion protein; and
 (d) separating the fusion protein from the inclusions.

Step (a) of said method has been explained in the previous section of "Method for purifying inclusions", therefore said description should be referred to.

In a particular embodiment, once a cell line generating the inclusions suitable for performing the purification method of the invention is available, (step (b)) is performed wherein there is expressed in said cell a fusion protein comprising a first component containing at least one polypeptide of interest and a second component suitable for directing the inclusions to the polypeptide/polypeptides of interest selected from the group of:
(a) a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
(b) a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
(c) a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
(d) a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.

The polypeptide of interest has been described previously in the preceding section of the fusion protein of the invention, as well as the fragments which can be directed to the inclusions.

The result of the two first steps of the purification method of the invention would be binding the polypeptide of interest to the inclusions through one of the regions described previously having affinity for the inclusions.

These two first steps can be performed in different order. Therefore, it is possible to first generate the inclusions and then express the fusion protein in the cell. Alternatively, it is possible to express the fusion protein in a cell and then generate the inclusions in said cell.

In a preferred embodiment, if the second component of the fusion protein comprises amino acids 381-448 (SEQ ID NO: 2) of avian *Orthoreovirus* muNS protein or the corresponding amino acids of mammalian *Orthoreovirus*, then the polypeptide expressed in step (a) is the complete avian or mammalian *Orthoreovirus* muNS protein or a functionally equivalent variant of any of the above.

Once the complex has been formed between the inclusions and the polypeptide of interest, step (c) comprises purifying said complex. To that end, methods for purifying inclusion bodies, as has been described previously in the context of the method for purifying the inclusions of the invention can typically be resorted to.

Once a preparation of inclusion bodies incorporating the protein of interest is available, step (d) comprises separating the fusion protein from the inclusions. To that end, the inclusions can be solubilized using chaotropic agents such as, without limitation, urea (from 4 M to 8 M), formamide (at least 80% v/v) and guanidine hydrochloride (from 4 M to 8 M). Some solvents which are capable of solubilizing aggregates include, for example, SDS and formic acid even though their use is unsuitable due to the lack of immunogenicity and/or activity. Once the protein bodies have been solubilized, the proteins can be recovered by means of the removing (by means of dialysis, for example) or diluting the denaturing agent, the formation of immunologically or biologically active proteins thus being allowed. Likewise, the fusion protein can be separated from the inclusions in the presence of a hypotonic buffer using a NaCl concentration of about 0.5 M, obtaining the fusion protein in solution with a high purity. In a particular embodiment, said hypotonic buffer does not have divalent ions.

The two components of the fusion protein are separated once the inclusions are separated from the fusion protein. To that end, the first and second component of the fusion protein can be connected by a peptide the sequence of which contains a protease cleavage target. The protease cleavage sites suitable for incorporation in the polypeptides of the invention include enterokinase (cleavage site DDDDK), Xa factor (cleavage site IEDGR), thrombin (cleavage site LVPRGS), protease TEV (cleavage site ENLYFQG), protease PreScission (cleavage site LEVLFQGP), inteins and the like. A person skilled in the art would know the specific cleavage conditions of each of the proteases. In a preferred embodiment, the separation is carried out as has been described in Example 6.

The person skilled in the art knows the different methods for purifying the polypeptide of interest bound to the inclusions. Methods suitable for purifying said complex include, but are not limited to, the protocol for purifying GFP-Intercoil in insect Sf9 cells infected with baculovirus described in Example 6 of the present specification. Primarily, the method consists of lysing the cells, sonicating the extract and purifying the inclusions with bound GFP-Intercoil in the pellet. For the purpose of checking if the purification has been successful, an electrophoresis could be carried out in denaturing conditions, checking that the polypeptide of interest is present in the extract after purification.

In another aspect, the invention relates to a method for purifying a fusion protein comprising a polypeptide of interest from a composition containing said fusion protein which comprises:
(a) contacting a polypeptide with inclusion-forming capacity in the presence of divalent cations selected from the group formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with said composition containing the fusion protein to be purified, wherein said fusion protein comprises:
 (i) a first component containing at least one polypeptide of interest; and
 (ii) a second component selected from the group of:
  a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
  a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
  a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
  a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;
 wherein the polypeptide with inclusion-forming capacity in the presence of divalent cations is in soluble form and
 wherein said contacting is performed in the presence of a divalent cation concentration suitable for forming inclusions from the polypeptide with inclusion-forming capacity and from the fusion protein,
(b) purifying the complex formed in the (a) and
(c) separating the fusion protein from the polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above.

In a first step, the second method for purifying a fusion protein comprises contacting a polypeptide with inclusion-forming capacity in the presence of divalent cations selected from the group of a polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above, with a composition comprising the fusion protein wherein said fusion protein comprises at least one region capable of directing said protein to an inclusion formed by the avian *Orthoreovirus* muNS protein wherein said contacting is performed in the presence of a divalent cation concentration suitable for forming inclusions from the polypeptide with inclusion-forming capacity and from the fusion protein.

In the context of the second purification method of the invention, the term "composition comprising the fusion protein" is used to refer to the fact that the fusion protein is not pure and it can be found in a cell extract or it can be part of a mixture of proteins or of other components, preferably from cell lysis.

The term "divalent cation", as used in the present invention, refers to a positively charged ion of any metal from the periodic table having a valence of 2. Divalent cations suitable for use in the present invention include, without limitation, the divalent cations of Mg, Cd, Ca, Co, Cu, Fe, Mn, Ni, Sr and Zn. In a preferred embodiment, the divalent cation is $Mg^{2+}$. Suitable concentrations of divalent cation for inducing the formation of muNS protein aggregates are, for example, at least 0.01 mM, at least 0.1 mM, at least 1 mM, at least 2 mM, at least 3 mM, at least 4 mM, at least 5 mM or greater. Solubilized muNS protein is preferably prepared from aggregates formed by the expression of the muNS protein or from muNS fragments or from inclusions, followed by solubilization of same in a medium in the absence of divalent cations. In an even more preferred embodiment, the fusion protein is in a buffer containing divalent cations in a concentration in excess with respect to that suitable for forming muNS protein aggregates, such that upon mixing the muNS preparation with the mixture containing the fusion protein, suitable concentrations in the sample of divalent cations are reached so that the muNS protein forms aggregates or inclusions incorporating the fusion protein. Therefore, in the case that the optimum divalent cation concentration is 5 mM, the mixture containing the fusion protein can contain up to 10 mM of said cations, such that upon combining a volume of the solution containing the soluble muNS protein and a volume of the mixture containing the fusion protein in the absence of divalent cations a final concentration of 5 mM which is suitable for forming muNS protein aggregates is obtained. The skilled person can calculate the divalent cation concentration necessary in the mixture containing the fusion protein such that, upon combining the latter with the composition comprising the muNS protein or the variant thereof, final divalent cation concentrations for forming the inclusions are obtained.

Step (a) is carried out for the time necessary so that the formation of muNS protein aggregates and of fusion protein takes place. This can be determined, for example, by means of conventional techniques for determining whether a protein is soluble at a specific concentration, such as turbidimetric methods like nephelometry, filtration and the like, The components used in the second method of the invention (the polypeptide capable of forming inclusions and the polypeptide capable of directing inclusions to the aggregates formed by said first polypeptide) have been defined in detail previously and are used similarly in the context of this method.

In a second step, the second method of the invention comprises separating the complex formed in (a) from the rest of components of the composition. In particular, if the fusion protein came from a crude cell extract in which said protein has been expressed, this step allows separating the aggregates from the rest of components present in the cell extract (polypeptides, nucleic acids, remains of cell wall, etc.). Methods suitable for separating the aggregates from the rest of components present in the sample include, without limitation, differential centrifugation, sedimentation, filtration, density gradient separation and the like.

In a third step, the second method of the invention comprises separating the fusion protein from the polypeptide from the polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above. Methods suitable for solubilizing the inclusions and for recovering the protein of interest from said inclusions have been described in detail previously.

In a particular embodiment, if the second component of the fusion protein in any of the purification methods comprises amino acids 381-448 (SEQ ID NO: 2) of avian *Orthoreovirus* muNS protein or the corresponding amino acids of mammalian *Orthoreovirus*, then the inclusions expressed in step (a) are those resulting from the complete avian or mammalian *Orthoreovirus* muNS protein or a functionally equivalent variant of any of the above.

Methods for Identifying Protein-Protein Interactions

The possibility of directing the proteins of interest to the inclusions formed by muNS and muNS-Mi has several potential applications in addition to protein purification. One of them is to identify interactions between proteins inside eukaryotic cells. Therefore, if a polypeptide of interest is tagged with one of the previously described domains for directing it to the inclusion bodies, it could attract other polypeptides interacting strongly therewith and relocate them in the inclusions, such as shown in Example 7, where the T-antigen is incorporated into the muNS-Mi inclusion bodies by binding to p53 which has been tagged with the Intercoil domain.

Therefore, in one aspect, the invention relates to a method for detecting the interaction between a first polypeptide and a second polypeptide, hereinafter method for detecting interactions of the invention, comprising:
(a) expressing in a cell the polypeptide comprising amino acids 448-635 (SEQ ID NO: 1) of avian *Orthoreovirus* muNS protein or the corresponding amino acids of mammalian *Orthoreovirus* muNS protein or the complete avian or mammalian *Orthoreovirus* muNS protein, or a functionally equivalent variant of any of the above and maintaining said cell in conditions suitable for inclusion formation;
(b) expressing in said cell the fusion protein comprising:
  (i) a first component containing the first polypeptide; and
  (ii) a second component selected from the group of:
    a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
    a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
    a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
    a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above.
  in suitable conditions so that the fusion protein is directed to the inclusions expressed in step (a);
(c) expressing in the preceding cell or in a different cell the second polypeptide or maintaining the cell of step (a) or (b) in suitable conditions so that said second polypeptide is expressed;
wherein steps (a), (b) and (c) are carried out in any order and
(d) determining whether the second polypeptide is associated with the complex formed by the inclusions generated in step (a) and the fusion protein expressed in step (b), wherein if the second polypeptide is detected it is indicative of the interaction between said first and second polypeptide.

The first two steps of the method for detecting interactions of the invention coincide with the first two steps of the purification method of the invention, therefore reference is made to said steps.

In a particular embodiment, the cell of steps (a), (b) and (c) can be the same cell, or two of the cells of steps (a), (b) and (c) are the same cell or the cells of steps (a), (b) and (c) are different. In other words, the inclusions, the fusion protein and the second polypeptide can be expressed in the same cell or in different cells. Likewise, it is also contemplated that the inclusions and fusion protein or the inclusions and the second polypeptide of interest or the fusion protein and the second polypeptide of interest are expressed in the same cell and the third element is expressed in a different cell. If the inclusions, the fusion protein and the second polypeptide are expressed in different cells, said cells should be lysed and the cell extracts of said cells or the cell lysate should be contacted such that the interaction between the different components can occur.

Once the inclusions and fusion protein comprising the first polypeptide have been expressed and the complex has been formed between the inclusions and the first polypeptide, the second polypeptide is expressed in said cell. Likewise, the order of steps (a), (b) and (c) can vary, such that the second polypeptide or the first polypeptide is first expressed, instead of the inclusions. The second polypeptide will be expressed similarly to the first polypeptide, such that reference is made to step (b) of the purification method of the invention.

The last step of the method for detecting interactions of the invention consists of determining whether the second polypeptide is associated with the complex formed by the inclusions generated in step (a) and the fusion protein expressed in step (b), wherein if the second polypeptide is detected, it is indicative that there has been an interaction between the first and second polypeptide.

Methods for detecting the interaction between two polypeptides are known by the person skilled in the art, and they include, without limitation electrophoresis in native conditions, molecular exclusion chromatography in conditions suitable for detecting the interaction, gradient centrifugation, immunoprecipitation, etc. In a preferred embodiment, the detection of the association between the first and the second polypeptide is carried out by means of the detection by means of immunofluorescence or fluorescence microscopy.

Said method for detecting the interaction between polypeptides can include the detection of the interaction between more than two polypeptides. Therefore, the assembly of supramolecular complexes in the cells for structural study may be favored by means of the system of interaction through inclusions. Many molecular complexes which are formed by several proteins are hard to be obtained by means of classic protein expression systems. The possible dispersion of the individual components thereof in the cell can possibly complicate the formation of said complexes. The virions of reovirus are supramolecular complexes which are naturally assembled in a highly efficient manner in the infected cell. To increase said efficiency, the components of the virions are recruited into the muNS inclusions in an ordered and selective manner (Touris-Otero et al. 2004, J. Mol. Biol. 341, 361-74). Therefore, since they are concentrated in the same compartment, the possibilities of finding the suitable ligands increase. The present method for detecting the interaction between polypeptides allows simulating the morphogenesis of reoviruses, but with exogenous proteins which can be selectively directed to the muNS or muNS-Mi inclusions. To that end, said polypeptides can be tagged with one of the domains mentioned previously and can direct several proteins to the inclusions in a simple manner and thus increase the possibilities of finding the suitable ligands for assembling complexes.

In a particular embodiment, the method for detecting interactions of the invention can be used for determining the interaction between nuclear proteins. In order for the inclusions to form inside the nucleus, a nuclear localization signal must be added to the polypeptide of the invention or to the complete muNS protein of the mammalian reovirus or of the avian reovirus. Examples of nuclear localization sequences are indicated in Section "Minimum region of muNS protein capable of forming inclusions", therefore reference is made to said explanation. In a particular embodiment, the nuclear signaling peptide is the NLS of the T-antigen (PKKKRKV) or a NLS of the T-antigen (PKKKRKV) fused with the Herpesvirus VP16 protein.

Likewise, in addition to a nuclear signaling peptide, in a particular embodiment, the polypeptide of the invention expressed in the cell of step (a) comprises a peptide to facilitate its purification. Said peptides to facilitate its purification have already been mentioned previously in Section "Minimum region of muNS protein capable of forming inclusions" and reference is made thereto.

In a particular embodiment, the fusion protein included in the cell of step (b) and/or the second polypeptide included in the cell of step (c) of the method for detecting interactions of the invention, comprise a peptide to facilitate its purification or a nuclear signaling peptide. Said peptides have been explained previously throughout the specification, therefore reference is made to those already described.

In a particular embodiment, in step (d) of the method for detecting interactions of the invention, it is determined whether there has been an interaction between the first and the second polypeptide, i.e., whether the second polypeptide is associated with the complex formed by the inclusions and the first polypeptide, through the appearance or detection of the second polypeptide in the nucleus. Due to the interaction between both polypeptides, the second polypeptide modifies its localization and is translocated from the cytoplasm to the nucleus, being bound to the complex formed by the inclusions and the first polypeptide.

Alternatively, since it is possible to assemble and disassemble the inclusions formed by the muNS protein or by the minimum region of said protein at will according to whether or not divalent cations are present in the mixture, the invention contemplates a second method for detecting the interaction between a first polypeptide and a second polypeptide which comprises (a) contacting a polypeptide with inclusion-forming capacity in the presence of divalent cations wherein said polypeptide is selected from the group formed by a polypeptide selected from the group formed by a polypeptide comprising amino acids 448-635 (SEQ ID NO: 1) of avian *Orthoreovirus* muNS protein, the region of mammalian *Orthoreovirus* muNS protein comprising the region corresponding to the region of avian *Orthoreovirus* muNS protein comprising amino acids 448-635 (SEQ ID NO: 1) of said protein, complete avian *Orthoreovirus* muNS protein, complete mammalian *Orthoreovirus* muNS protein and a functionally equivalent variant of any of the above with a fusion protein to be purified, wherein said fusion protein comprises:
(i) said first polypeptide and
(ii) a second component selected from the group of:
   a polypeptide comprising sequence 381-448 (SEQ ID NO: 2) of avian *Orthoreovirus* muNS protein or the corresponding sequence of mammalian *Orthoreovirus* muNS protein or a functionally equivalent variant of any of the above;
   a polypeptide comprising sequence 448-477 (SEQ ID NO: 3) of avian *Orthoreovirus* muNS protein or the corresponding sequence of mammalian *Orthoreovirus* muNS protein or a functionally equivalent variant of any of the above;
   a polypeptide comprising sequence 477-542 (SEQ ID NO: 4) of avian *Orthoreovirus* muNS protein or the corresponding sequence of mammalian *Orthoreovirus* muNS protein or a functionally equivalent variant of any of the above; and
   a polypeptide comprising sequence 539-605 (SEQ ID NO: 5) of avian *Orthoreovirus* muNS protein or the corresponding sequence of mammalian *Orthoreovirus* muNS protein or a functionally equivalent variant of any of the above;
wherein the polypeptide with inclusion-forming capacity in the presence of divalent cations is in soluble form and
wherein said contacting is performed in the presence of a divalent cation concentration suitable for forming inclusions from the polypeptide with inclusion-forming capacity and from the fusion protein,
(b) contacting the inclusions formed in step (a) with said second polypeptide and
(c) determining whether the second polypeptide is associated with the inclusions generated in step (a) wherein if the second polypeptide is detected it is indicative of the interaction between said first and second polypeptide.

The different steps of the second method for purifying proteins according to the invention have been described in detail in the context of the methods for purifying proteins according to the invention or in the context of the first method for detecting interaction between a first polypeptide and a second polypeptide according to the invention.

In a preferred embodiment, if the second component of the fusion protein comprises amino acids 381-448 (SEQ ID NO: 2) of avian *Orthoreovirus* muNS protein or the corresponding amino acids of mammalian *Orthoreovirus*, then the protein used in step (a) is the complete avian or mammalian *Orthoreovirus* muNS protein or a functionally equivalent variant of any of the above.

The following serve to illustrate the invention and must not be considered as limiting the scope thereof.

EXAMPLES

Materials and Methods

Cells

Primary cultures of chicken embryonic fibroblasts (CEF) prepared as described in the method section were used for transfections. Cos-7 cells were also used. Insect Sf9 cells were used for expressing proteins with baculovirus.

Antibodies

The polyclonal avian reovirus anti-muNS S1133 protein antibody was previously obtained by the same inventors (Touris-Otero et al. Virology, 319; 94-106). Different commercial antibodies were also used:

Monoclonal *Aequorea victoria* anti-green fluorescent protein (GFP) antibody (Roche, Barcelona, Spain).

Polyclonal rabbit antibody specific against the hemaglutinnin epitope of the influenza virus (Sigma-Aldrich, Madrid, Spain).

Monoclonal anti-p53 antibody (clon PAB40) (Sigma-Aldrich, Madrid, Spain).

Monoclonal anti-SV40 T-antigen antibody (clone PAb101) (BDbiosciences, Madrid, Spain).

Rabbit and mouse peroxidase-conjugated anti-IgG antibodies (Sigma-Aldrich, Madrid, Spain) used for the indirect detection by Western using the chemiluminescent HRP (horseradish peroxidase) substrate from Millipore (Madrid, Spain).

Rabbit and mouse Alexa 488- and an Alexa 594-conjugated anti-IgG antibodies, respectively (Sigma-Aldrich, Madrid, Spain), used as secondary antibodies in the immunofluorescences.

Bacteria

DH5-α: Bacterial strain of *E. coli* used for growing and purifying plasmids. Genotype: supE44, Δ lacU169(φ80lacZ ΔM15), hsdR17, recA1, endA1, gyrA96, thi-1, relA1 (Hanahan, 1983).

DH10Bac: Bacterial strain of *E. coli* used for generating recombinant baculoviruses. Genotype: F-mcrA D(mrrhs-dRMS-mcrBC) φ80dlacZDM15 ΔlacX74 deoR recA1 endA1 araD139 Δ(ara, 27leu)7697 galU galK λ-rpsL nupG /bMON14272/pMON7124 (Invitrogen, Barcelona, Spain).

XL1-Blue: Bacterial strain of *E. coli* used for cloning PCR products in the corresponding plasmids. Genotype: recA1, endA1, gyrA96, thi-1, hsdR17, supE44, relA1, lac [F'proAB laclqZΔM15 Tn10 (Tetr)] (Stratagene, The Jolla, Calif.). To make these cells competent and to transform them, the protocol described by Chung et. al. (1989) (Chung et al. 1989. PNAS 86: 2172-5) was followed.

Plasmids pCDNA3.1/Zeo (Invitrogen, Barcelona, Spain): expression vector in eukaryotic cells allowing the expression of genes transiently cloned under cytomegalovirus early promoter.

pFastBacI (Invitrogen, Barcelona, Spain): vector with bacterial transposon Tn7, which allows inserting the cloned sequence in a bacmid upon transforming it in DH10Bac.

pEGFP-C1 (Clontech, Saint Germain en Laye, France): protein expression vector in eukaryotic cells fused to the enhanced green fluorescent protein (EGFP) at its amino end. The promoter, such as in pCDA3.1/Zeo, is that of cytomegalovirus.

pEGFP-N1 (Clontech, Saint Germain en Laye, France): protein expression vector in eukaryotic cells fused to the enhanced green fluorescent protein (EGFP) at its catboxyl end. The promoter, such as in pEGFP-C1, is that of cytomegalovirus.

pCINeo (Promega, Madrid, Spain): expression vector in eukaryotic cells allowing the expression of genes transiently cloned under cytomegalovirus early promoter.

pVP16 (Clontech, Saint Germain en Laye, France): protein expression vector in eukaryotic cells fused at its amino end to a protein of the herpes virus (VP16) acting as a transcription activator, and it also contains coupled thereto a NLS (nuclear localization sequence) of the SV40 T-antigen. The early promoter is that of SV40.

Culture Media

The chicken embryonic fibroblasts were incubated in medium 199 (1×) (Invitrogen, Barcelona, Spain) supplemented with 10% (w/v) tryptose phosphate broth (TPB) and 5% (v/v) bovine serum.

The Sf9 cells were grown in suspension in serum-free Sf900II medium or in monolayer in Sf900II medium supplemented with 10% (v/v) fetal bovine serum at 28° C. (Invitrogen, Barcelona, Spain).

The Cos-7 cells were grown in D-MEM medium (Invitrogen, Barcelona, Spain) supplemented with 10% (v/v) fetal bovine serum.

The bacteria were grown in LB medium or LB-agar supplemented with the suitable antibiotic (Sambrook et al., Cold Spring Harbor Laboratory Press, third edition, 2001), except when DH10Bac were transformed since the commercial protocol recommends the use of SOC medium (Sambrook et al., Cold Spring Harbor Laboratory Press, third edition, 2001) to improve transformation/transposition efficiency.

Methods

Obtaining Chicken Embryonic Fibroblasts (CEF).

These cells were obtained from chicken embryos after 9-10 days of incubation (supplied by Intervet, Salamanca). The egg shell was washed with ethanol, being located on a support with the broader end upwards. The shell was peeled with sterile forceps and the chorioallantoic membrane was broken to penetrate the amniotic cavity. The removed embryo was decapitated and gutted. The resulting tissue was washed 3× with PBS (137 mM NaCl; 2.7 mM KCl; 8 mM Na$_2$HPO$_4$; 1.5 mM KH$_2$PO$_4$) at 37° C. and was cut into pieces with scissors. The resulting pap was digested with trypsin (10 ml of trypsin, 0.25% PBS per embryo) at 37° C. for 45 min. It was then passed through a grate, an equal volume of medium 199 was added and centrifuged 25 min at 1500 g. The resulting pellet was resuspended in medium 199 preheated to 37° C. and supplemented with 10% TPB (tryptose phosphate broth), 75% bovine serum, antibiotics and fungizone. The cell suspension was seeded in plates incubated at 37° C.

Transient Protein Expression in Eukaryotic Cells.

Plasmids containing the different constructs were transfected in semi-confluent CEF or Cos-7 cells according to the manufacturer's instructions, using "Lipofectamine Plus Reagent" (Invitrogen, Barcelona, Spain). Unless otherwise indicated, the cells were analyzed 24 hours post-transfection (hpt).

Immunofluorescence

Cells grown on round cover slips in a 12 multiwell plate were transfected or infected as indicated in the text. After washing with PBS (137 mM NaCl; 2.7 mM KCl; 8 mM Na$_2$HPO$_4$; 1.5 mM KH$_2$PO$_4$), were fixed with paraformaldehyde for 15 minutes. The fixed cells were washed with PBS and incubated for 1 h. in blocking buffer (3% BSA (Sigma, Madrid, Spain), 0.1% Triton X-100 in PBS). The cover slips were incubated for 1 h with primary antibodies, previously diluted to 1:1000 in a blocking buffer. The cells were then washed three times with PBS (10 min. each wash) and were incubated for another 30 min. with the secondary antibodies (1:1000) and DAPI (Sigma) diluted in blocking buffer. The cover slips were washed six times with PBS (5 min. each wash) and mounted on slides with a drop of mounting medium (6 g glycerol; 2.4 g mowiol; 6 ml H$_2$O and 12 ml 0.2 M Tris-HCl (pH 8.5)). The images were obtained with an Olympus DP-71 digital camera assembled on an Olympus BX51fluorescence microscope. The photos obtained were processed with Adobe Photoshop (Adobe Systems, California, USA).

Analysis of Proteins in Polyacrylamide Gels.

The samples were mixed with one third of the volume of Laemmli buffer thereof for electrophoresis (62.5 mM Tris-HCl, pH 6.8; 17% glycerol; 0.1 M β-mercaptoethanol; 2% SDS; 0.024% bromopehol blue) and boiled for 3 min. They were then analyzed by means of the discontinuous electrophoresis technique in the presence of SDS (SDS-PAGE) initially developed by Laemmli (1970). The proteins were viewed with 0.1% Coomassie blue. In some occasions the gels were not fixed but were transferred to a PVDF membrane (Millipore, Madrid, Spain) to analyze it by Western-Blot.

Protein Transfer and Western-Blot.

Four parts of Whatman 3MM paper and one of PVDF paper (Millipore, Madrid, Spain), of the size of the gel to be transferred were cleaved and were submerged in a transfer buffer (25 mM Tris base; 192 mM Glycine; 20% Methanol), as well as the polyacrylamide gel with the proteins to be transferred. After half an hour the "sandwich" for the transfer is prepared. The transfer is carried out in a Bio-Rad Trans-Blot cell by applying 100 V for 1 h. To check the effectiveness of the transfer, pre-stained molecular weight markers (Invitrogen, Barcelona, Spain) were used. The PVDF membrane with the already transferred proteins was incubated for at least at least one hour in PBS containing 5% skimmed milk powder and 0.1% Tween 20 (blotto), in order to block all the membrane binding sites. The primary antibody (diluted to 1:10000 in blotto in the case of anti-muNS or to 1:1000 in the case of GFP) was then added and incubated for 1 h, after which three washings of 5 min were performed with blotto to remove the unbound antibody. The membrane was then incubated with the secondary antibody for 30 min. and the washings were repeated to remove the secondary antibody. Western-blot was revealed using chemiluminescent HRP (horseradish peroxidase) substrate from Millipore (Madrid, Spain).

Constructions of Plasmids

Constructing the recombinant plasmid pCINeo-M3, expressing avian reovirus muNS protein S1133 has been described previously (Touris-Otero et al. 2004, J. Mol. Biol. 341, 361-74).

For constructing the recombinant plasmid pVP16-muNS expressing muNS fused to the carboxyl end of an activation domain (VP16) and having coupled thereto the NLS of the SV40 T-antigen (designated as VP16-muNS), the plasmid pGEMT-M3 was amplified by PCR with the following primers: SEQ ID NO: 9 and SEQ ID NO: 10. The resulting PCR product was digested and cloned in the vector pVP16.

For obtaining the recombinant plasmid pVP16-GFP-muNS expressing the chimera GFPmuNS fused to the carboxyl end of an activation domain containing the NLS of the T-antigen (hereinafter called VP16-GFP-muNS), the recombinant plasmid pEGFP-C1-M3 (Touris-Otero et al. 2004, J. Mol. Biol. 341, 361-74) was amplified by PCR with primers the sequence of which is SEQ ID NO:11 and SEQ ID NO:12. The resulting PCR product was digested with BamHI and XbaI and subsequently ligated to the plasmid pVP16, which was cleaved with the same enzymes. The construct obtained was verified by means of sequencing and Western-blot using anti-muNS antibodies (data not shown).

For generating the recombinant plasmid pCDNA3.1/Zeo-NLS-Ag.T-muNS expressing the muNS protein fused with the NLS of the T-antigen at its amino end (called NLSAg.T-muNS in the Results), the recombinant plasmid pGEMT-M3 (Touris-Otero et al. 2004, J. Mol. Biol. 341, 361-74) was amplified by PCR with primers the sequence of which is SEQ ID NO:13 and SEQ ID NO:12. The resulting PCR product was digested with EcoRI and XbaI and subsequently ligated to the plasmid pCDNA3.1/Zeo, which was digested with the same enzymes. The construct obtained was verified by means of sequencing and Western-blot using anti-muNS antibodies (data not shown).

For obtaining the recombinant plasmid pCDNA3.1/Zeo-NLS-Ag.T-GFP-muNS expressing the chimera GFP-muNS fused to the NLS of the T-antigen at its amino end (hereinafter called NLS-Ag.T-GFP-muNS), the recombinant plasmid pEGFP-C1-M3 (Touris-Otero et al. 2004, J. Mol. Biol. 341, 361-74) was amplified by PCR with primers the sequence of which is SEQ ID NO:14 and SEQ ID NO:12. The resulting PCR product was digested with BamHI and XbaI and subsequently ligated to the plasmid pCDNA3.1/Zeo, which was cleaved with the same enzymes. The construct obtained was verified by means of sequencing and Western-blot using anti-muNS antibodies (data not shown).

For generating the recombinant plasmid pCDNA3.1/Zeo-NLS-Ag.T-GFP-muNS(448-635) expressing the chimera GFP-muNS (448-635) (hereinafter also called GFP-muNS-Mi) fused with the NLS of the T-antigen at its amino end (called NLS-Ag.T-GFP-muNS-Mi hereinafter), the recombinant plasmid pEGFP-C1-M3(448-635) was amplified by PCR with the same primers as in the preceding case (SEQ ID NO:14 and SEQ ID NO:12). The resulting PCR product was digested with BamHI and XbaI and subsequently ligated to the plasmid pCDNA3.1/Zeo which was cleaved with the same enzymes. The construct obtained was verified by means of sequencing and Western-blot using anti-muNS antibodies (data not shown).

The vector pEGFP-N1 (BD Biosciences, Madrid, Spain) was used for expressing the fusion of *Aequorea victoria* enhanced green fluorescent protein (EGFP) to the carboxyl end of the region of muNS comprising the amino acids 381 to 448 (muNS(381-448)). To that end, the recombinant plasmid (Touris-Otero et al. 2004, J. Mol. Biol. 341, 361-74) was amplified by PCR with primers the sequence of which is SEQ ID NO:13 and SEQ ID NO:14. The resulting PCR product was digested with EcoRI and BamHI and subsequently ligated to the plasmid pEGFP-N1 which was cleaved with the same enzymes. The construct obtained was verified by means of sequencing and Western-blot using anti-muNS antibodies (data not shown).

The vector pEGFP-C1 (BD Biosciences, Madrid, Spain) was used for expressing the fusions of *A. victoria* enhanced green fluorescent protein (EGFP) to the amino end of specific regions of muNS. The construction of the recombinant plasmid pEGFP-C1-M3 expressing avian reovirus muNS protein S1133 fused to GFP at its amino end (hereinafter called GFP-muNS) has been described previously (Touris-Otero et al. 2004, J. Mol. Biol. 341, 361-74). The generation of the recombinant plasmid pEGFP-C1-M3 (448-635) expressing the region including the residues 448 to 635 of avian reovirus muNS protein 51133 fused to GFP at its amino end (hereinafter called GFP-muNS-Mi) is carried out by amplifying the region of muNS (448-635), using pGEMTM3 (Touris-Otero et al. 2004, J. Mol. Biol. 341, 361-74) from the primers SEQ ID NO: 20 and SEQ ID NO: 21 (see Table 1) as a template.

For expressing the EGFP fused to the amino end of different regions of muNS, targets for EcoRI and BamHI were introduced with the primers during the amplification by PCR in the region of the M3 gene to be amplified. The PCRs were performed (Touris-Otero et al. 2004, J. Mol. Biol. 341, 361-74) using pGEMTM3 as a template and the primers are listed in Table 1. The PCR products were cleaved with EcoRI and BamHI and subsequently ligated to pEGFP-C1 which was cleaved with the same enzymes. All the constructs were verified by means of sequencing and Western-blot using anti-muNS and anti-GFP antibodies (data not shown).

TABLE 1

GFP-muNS chimaera construct

| Construct | Primers (5'-3')[1] | Protein[2] | Size (kDa)[3] |
|---|---|---|---|
| pGEFP-C1-M3(1-477) | F-SEQ ID NO: 15<br>R- SEQ ID NO: 16 | GFP/muNS (1-477) | 81.0 |
| pGEFP-C1-M3(1-448) | F- SEQ ID NO: 15<br>R- SEQ ID NO: 17 | GFP/muNS (1-448) | 77.8 |
| pGEFP-C1-M3(1-380) | F- SEQ ID NO: 15<br>R- SEQ ID NO: 18 | GFP/muNS (1-380) | 70.6 |
| pGEFP-C1-M3(1-154) | F- SEQ ID NO: 15<br>R- SEQ ID NO: 19 | GFP/muNS (1-154) | 45.4 |
| pGEFP-C1-M3(448-635) | F- SEQ ID NO: 20<br>R- SEQ ID NO: 21 | GFP/muNS (448-635) | 49.5 |
| pGEFP-C1-M3(605-635) | F- SEQ ID NO: 22<br>R- SEQ ID NO: 21 | GFP/muNS (605-635) | 31.3 |
| pGEFP-C1-M3(448-477) | F- SEQ ID NO: 20<br>R- SEQ ID NO: 16 | GFP/muNS (448-477) | 31.3 |
| pGEFP-C1-M3(477-542) | F- SEQ ID NO: 23<br>R- SEQ ID NO: 24 | GFP/muNS (477-542) | 35.7 |
| pGEFP-C1-M3(539-605) | F- SEQ ID NO: 25<br>R- SEQ ID NO: 26 | GFP/muNS (539-605) | 36.0 |
| pGEFP-C1-M3(381-448) | F- SEQ ID NO: 27<br>R-SEQ ID NO: 17 | GFP/muNS (381-448) | 35.3 |

[1]A stop codon was added to the reverse primer (R) stop and a start codon was added to the forward primer. The targets of EcoRI or BamHI are incorporated at the 5' end of the primers.
[2]In each of the chimeras, GFP was fused to the amino end of the indicated region of muNS.
[3]Expected size for fusion proteins expressed.

For expressing the EGFP fused to the N-terminus end of the region of muNS comprising residues 477 to 542, such that it contains a cleavage site for the Xa factor between both proteins, the recombinant plasmid pGEMT-M3 (Touris-Otero et al. 2004, J. Mol. Biol. 341, 361-74) was amplified by PCR with primers the sequence of which is SEQ ID NO:28 and SEQ ID NO:24. The resulting PCR product was cleaved with EcoRI and BamHI and subsequently ligated to the vector pEGFP-C1 which was cleaved with the same enzymes. The construct generated (pEGFP-C1-Xa-muNS (477-542) was verified by means of sequencing and Western-blot using anti-muNS antibodies and GFP (data not shown).

For expressing regions of muNS fused to the hemaglutinnin of the influenza virus (HA) at its C-terminus end, the epitope-encoding sequence, the start and stop codons and the targets of restriction enzymes were introduced with the primers during the amplification by PCR in the region of the M3 gene to be amplified. The PCRs were performed using pGEMT-M3 as a template (Touris-Otero et al. 2004, J. Mol. Biol. 341, 361-74) and the primers listed in Table 2. The PCR products were cleaved with EcoRI and XbaI and subsequently ligated to pCDNA3.1/Zeo which was digested with the same enzymes. All the constructs were verified by means of sequencing and Western-blot using anti-muNS antibodies (data not shown).

TABLE 2

HA-muNS chimera construct

| Construct | Primers (5'-3')[4] | Protein[5] | Size (kDa)[6] |
|---|---|---|---|
| pCDNA3.1/Zeo-M3(1-154)-HA | F-SEQ ID NO: 29<br>R- SEQ ID NO: 30 | muNS (1-154)-HA | 18.3 |
| pCDNA3.1/Zeo-M3(1-380)-HA | F- SEQ ID NO: 31<br>R- SEQ ID NO: 32 | muNS (1-380)-HA | 43.4 |
| pCDNA3.1/Zeo-M3(1-448)-HA | F- SEQ ID NO: 33<br>R- SEQ ID NO: 34 | muNS (1-448)-HA | 50.6 |
| pCDNA3.1/Zeo-M3(1-477)-HA | F- SEQ ID NO: 35<br>R- SEQ ID NO: 36 | muNS (1-477)-HA | 53.8 |
| pCDNA3.1/Zeo-M3(539-635)-HA | F- SEQ ID NO: 37<br>R- SEQ ID NO: 38 | muNS (539-635)-HA | 12.3 |
| pCDNA3.1/Zeo-M3(539-605)-HA | F- SEQ ID NO: 39<br>R- SEQ ID NO: 40 | muNS (539-605)-HA | 9.2 |
| pCDNA3.1/Zeo-M3(477-542)-HA | F- SEQ ID NO: 41<br>R- SEQ ID NO: 42 | muNS (477-542)-HA | 8.8 |
| pCDNA3.1/Zeo-M3(381-448)-HA | F- SEQ ID NO: 43<br>R- SEQ ID NO: 44 | muNS (381-448)-HA | 8.2 |

[4]A stop codon was added to the negative primer (R) stop and a start codon was added to the positive primer. The targets of EcoRI or BamHI are incorporated at the 5' end of the primers.
[5]In each of the chimeras, GFP was fused to the amino end of the indicated region of muNS.
[6]Expected size for fusion proteins expressed.

The plasmids pCMV-wtAgT (expressing the long version of the T-antigen) and pCMV-wtp53 (expressing human wild type p53) were supplied by Dr. J. B. Zalvide (Departament of Physiology, Faculty of Medicine, USC).

For expressing human p53 protein fused to the N-terminus end of the region of muNS comprising residues 477 to 542, the recombinant plasmid pGEMT-M3 (Touris-Otero et al. 2004, J. Mol. Biol. 341, 361-74) was amplified by PCR with primers the sequence of which is SEQ ID NO:45 and SEQ ID NO:46. The resulting PCR product was digested with ApaI and XbaI and subsequently ligated to plasmid pCDNA3.1/Zeo which was cleaved with the same enzymes, the recombinant plasmid pCDNA3.1/Zeo-muNS(477-542) being obtained. The complete human p53-encoding sequence was then amplified by means of PCR using pCMV-wtp53 as a template and the primers the sequence of which is SEQ ID NO:47 and SEQ ID NO:48. The resulting PCR product and the plasmid pCDNA3.1/Zeo-muNS(477-542) were digested with BamHI and EcoRI and ligated, the recombinant plasmid pCDNA3.1/Zeo-p53-muNS(477-542) being generated. The construct obtained was verified by means of sequencing and Western-blot using anti-muNS antibodies and p53 (data not shown).

For expressing the protein HaloTag fused to the N-terminus end of the region of muNS comprising residues 477 to 542, the complete HaloTag-encoding sequence was amplified by means of PCR using the plasmid pHT2 (Promega, Madrid, Spain) as a template and the following primers: the positive primer of SEQ ID NO:53 and the negative primer SEQ ID NO:54. The resulting PCR product and the plasmid pCDNA3.1/Zeo-muNS(477-542) were digested with BamHI and NotI and ligated, the recombinant plasmid pCDNA3.1/Zeo-HaloTag-muNS(477-542) being generated. The construction obtained was verified by means of sequencing and Western-blot using anti-muNS antibodies (data not shown).

Construction of Recombinant Baculoviruses.

Recombinant baculovirus Bac-muNS expressing avian reovirus muNS protein S1133 was constructed by amplifying the plasmid pGEMT-M3 with the primers of sequence SEQ ID NO:9 and SEQ ID NO:8.

The recombinant baculovirus pCINeo-M3 (448-635) expressing the region including residues 448 to 635 of avian reovirus muNS protein S1133 (hereinafter called muNS-Mi) was constructed from the plasmid pGEMT-M3, amplifying by PCR, using the primers of sequence SEQ ID NO: 7 and SEQ ID NO: 8. The resulting PCR product was digested and cloned in the EcoRI and XbaI sites of the pFastBac1 vector (Bac-to-Bac system; Invitrogen, Barcelona). The pFastBac1-muNS (448-635) was used for generating the recombinant baculovirus Bac-muNS (448-635).

For expressing the recombinant protein GFP-Xa-muNS (477-542) in insect cells (hereinafter), the GFP-Xa-muNS (477-542)-encoding sequence present in the plasmid pEGFP-C1-Xa-muNS(477-542) was amplified by PCR using the primers the sequence of which is SEQ ID NO:49 and SEQ ID NO:50. The resulting PCR product was digested and cloned between the pFastBac1 (Bac-to-Bac system; Invitrogen, Barcelona, Spain) BamHI and XbaI restriction targets for obtaining pFastBac1-GFP-Xa-muNS (477-542), which was used for generating the recombinant baculovirus Bac-GFP-Xa-muNS(477-542), as recommended by the manufacturer in its instructions. This baculovirus expresses the GFP-Xa-muNS(477-542) gene under the control of polyhedrin promoter.

For generating the recombinant baculovirus expressing the GFP protein, the GFP-encoding sequence was amplified by PCR using the vector pEGFP-C1 as a template and the primers the sequence of which is SEQ ID NO:51 and SEQ ID NO:52. The resulting PCR product was digested and cloned between pFastBac1 (Bac-to-Bac system; Invitrogen, Barcelona, Spain) EcoRI and XbaI restriction targets for obtaining pFastBac1-GFP, which was used for generating the recombinant baculovirus Bac-GFP, such as recommended by the manufacturer in its instructions. This baculovirus expresses the GFP gene under the control of polyhedrin promoter.

Protocol for Purifying the Inclusions

After determining the titer of the different recombinant baculoviruses used in this research, they were co-infected with 5 pfu/cell (negative controls: Bac-muNS/Bac-GFP or Bac-muNS-Mi/Bac-GFP; or samples object of the study: Bac-muNS/Bac-GFP-Xa-Intercoil or Bac-muNS-Mi/Bac-GFP-Xa-Intercoil) a flask with Sf9 cells in suspension ($1.5 \times 10^6$ cells/ml) with a viability greater than 99%. The cells were maintained in an Erlenmeyer being stirred at 120 rpm at 28° C. for three days (point in which the proteins which are expressed under polyhedrin promoter tend to reach maximum), and were then centrifuged for 10 min. at 1000×g. The pellet was resuspended in 10 ml of hypotonic buffer (10 mM Hepes pH 7.9, 10 mM KCl, 5 mM $MgCl_2$) and put in ice for 15 min. to facilitate cell lysate.

The resulting cell extract was centrifuged at 2000×g/10 min. at 4° C., and the resulting pellet was resuspended in 10 ml of hypotonic buffer and centrifuged at 2000×g for 10 min., being washed twice in a volume of 10 ml of hypotonic buffer. The pellet was then resuspended in the same volume of hypotonic buffer and sonicated (45 cycles of 6 pulses, 0.5 cycles and amplitude 50), in order to break the cell nuclei and fragment the DNA. The sonicated extract was centrifuged at 4° C. at 200×g for 5 min. and the pellet was resuspended in 5 ml of hypotonic buffer and washed 5 times in the same volume of hypotonic buffer (200×g/5 min.). The resulting pellet was then resuspended in 1 ml of hypotonic buffer in the case of negative controls (Bac-muNS/Bac-GFP and Bac-muNS-Mi/Bac-GFP) and in hypotonic buffer with 500 mM NaCl in the case of samples object of the study (BacmuNS/Bac-GFP-Xa-Intercoil or Bac-muNS-Mi/Bac-GFP-Xa-Intercoil). The sample resuspended in salt was centrifuged for 5 min. at 16000×g to remove the insoluble residues and the supernatant was passed through a desalting column (HiTrap™ Desalting Column, GE Healthcare, Madrid, Spain). The eluate was centrifuged for 5 min. at 16000×g to remove the insoluble residues leaving the supernatant. Finally, the supernatant containing mainly GFP-Xa-Intercoil (see Example 6) was incubated with Xa factor (New England Biolabs, Ipswich, England) (dilution 1/1000) and after two days of treatment, it was centrifuged for 5 min. at 16000×g, it is in the supernatant where it was observed that most GFP-Xa-Intercoil had been cleaved, GFP being obtained (see Example 6). To check that all the GFP-Xa-Intercoil has been digested, it was incubated for another day with Xa factor, centrifuged for 5 min. at 16,000×g and the resulting supernatant was loaded in a Q-Sepharose column (GE Healthcare, Madrid, Spain) pre-equilibrated with hypotonic buffer (10 mM Hepes pH 7.9, 10 mM KCl, 5 mM $MgCl_2$). The column was eluded with increasing NaCl concentrations and the fractions collected were analyzed by SDS-PAGE, the presence of GFP being detected in the elution of 400 mM of NaCl (data not shown). Finally, the protein was concentrated and loaded in a gel, a single band of about 30 kDa being observed which was confirmed as GFP by means of Western-blot.

An alternative protocol for purifying inclusions consists of two steps common with the preceding protocol: resuspending the cell pellet in 10 ml of hypotonic buffer and centrifuging at 2000×g for 10 min., being washed twice in a volume of 10 ml of hypotonic buffer. Then, instead of performing sonication, the pellets obtained are treated for 15 minutes with a buffer A (10 mM Hepes pH 7.9, 10 mM KCl), i.e., the same as the hypotonic buffer removing the magnesium. Most of the muNS protein are thus solubilized. Nevertheless, upon adding 5 mM of magnesium to the soluble muNS protein again, the latter reforms aggregates which can be easily recovered by centrifugation (see Example 6 (C)).

These purification protocols are those which have been used throughout the entire specification for isolating or purifying different inclusions generated by the invention.

Example 1

Minimum Region of muNS Protein Capable of Forming Inclusions

If the inclusions are exclusively generated by the interactions between muNS-muNS, each muNS monomer must contain several domains which will interact with same, necessary for constructing the three-dimensional lattice required for constructing an inclusion. For the purpose of identifying the muNS domains of the avian *Orthoreovirus* necessary for inclusion formation, the plasmids which expressed the deletion mutants in C-terminus and N-terminus (shown in FIGS. 1 and 2) were constructed and transfected in CEF cells. The capacity of the constructs to form globular cytoplasmic inclusions was analyzed by indirect immunofluorescence using polyclonal anti-muNS antibodies. Ubiquitin-conjugated and anti-vimentin antibodies were used for distingushing inclusions and structures containing aggregated/misfolded protein (some examples are shown in FIG. 2B).

First, the C-terminus truncations shown in FIG. 1 were confirmed. None of the truncated proteins seemed to aggregate or to misfold since they were not co-localized with the conjugated ubiquitin nor did they induced the re-distribution of induced vimentin (data not shown). Surprisingly, none of the C-terminus truncations analyzed was capable of forming inclusions, but they showed a diffused intracellular distribution. These results indicate that the sequences at the C-terminus end of muNS are very important for forming inclusions.

The following step was evaluating the importance of the N-terminus sequences by analyzing the capacity of the N-terminus truncations which are shown in FIG. 2A to form inclusions. The deletion of up to 140 residues from the N-terminus end of the muNS protein did not adversely affect the capacity of the viral protein to form inclusions and did not alter the morphology of the inclusions (FIG. 2A, compare panels 1 and 3), suggesting that these residues are non-essential for inclusion formation. However, the truncations of muNS where up to 380, 420 or 447 residues were deleted from the N-terminus formed inclusions which were smaller in size and more spherical than those formed by the complete muNS protein (FIG. 2A, compare panels 1 and 5), muNS protein (127-635) or muNS (140-635) (FIG. 2A, compare panels 3 and 5). These results suggest that the residues between the region of muNS 140-380 control the morphology and the size of the inclusions. Unlike the truncations mentioned previously which did not show co-localization with ubiquitin (FIG. 2B, lines 1 and 3) or reorganization of vimentin, the truncations of muNS (84-635), muNS (112-635), muNS (208-635) and muNS (271-635) were recognized by the anti-ubiquitin antibodies in most of the cells (FIG. 2A, panels 2 and 4; FIG. 2B, line 2), suggesting that they were misfolded/aggregated. Finally, the truncations where more than 447 residues were missing from N-terminus were not capable of forming inclusions, but were uniformly distributed throughout the cell (FIG. 2A, panel 6). Therefore, all the preceding results suggest that the segment comprising residues 448-635 is the minimum region of muNS which seems to be necessary and sufficient to form inclusions, therefore it has been designated as muNS-Mi throughout the specification.

Like the complete muNS, muNS-Mi formed globular inclusions when expressed from recombinant baculoviruses in insect cells, and these inclusions can be easily purified by means of the protocol described in the section of "Methods" in the examples. The analysis of the protein composition by SDS-PAGE revealed that these inclusions essentially contain muNS-Mi and not cellular proteins. However, even though the level of expression of muNS-Mi in insect cells was similar to that of the complete protein, the former generated several ball-shaped inclusions per cell, whereas the latter formed only one large inclusion occupying most of the cell cytoplasm (data not shown).

Example 2

Identification of the Domains Forming the muNS Protein.

The analysis of the sequence deduced from muNS of the avian Orthoreovirus revealed the presence of four different regions in muNS-Mi (Touris-Otero et al. Virology, 319; 94-10) (FIG. 3A): two "coiled-coil" elements (one comprising residues 448-477, designated as Coil1 or C1 and the other comprising residues 539-605 designated as Coil2 or C2); a spacer region of 61 residues binding the two said "coiled-coil" (designated as Intercoil or IC); and finally, a region of 30 residues towards the C-terminus end of the second "coiled-coil" comprising residues 605-635 (designated as C-Tail or CT).

The function performed by the different muNS-Mi domains in inclusion formation was inspected, arriving at following conclusions: i) Coil1 can be replaced with a dimerization domain and ii) C-tail plays a key role in orienting the contacts between µNS monomers to form basal oligomers, thus controlling the shape of the inclusions and their formation efficiency. Likewise, the inventors have shown that in the N-terminus area of the protein there is a domain which, even though is not essential for forming inclusions, controls the shape and the size thereof.

Finally, it is known that the Intercoil region of avian muNS contains a small consensus motif common to all the inspected homologous muNS proteins of different reovirus (Broering et al., 2005. J. Virol. 79: 6194-6206). This sequence contains two universally conserved residues, His 570 and Cys 572, and it has been shown that mutations in the mammalian Orthoreovirus muNS protein in one of these residues completely eliminate its inclusion-forming capacity (Broering et al., 2005. J. Virol. 79: 6194-6206). To check whether this also occurred with orthoavian reoviruses, the inventors generated constructs encoding point mutations in equivalent positions for residues of avian muNS (His 487 to Gln and Cys489 to Ser) and expressed the mutants in transfected cells. Such as shown in FIG. 3B, the mutants H487Q and C489S were uniformly distributed throughout the cell cytoplasm, showing that His487 and Cys489 are necessary for the avian muNS protein to form inclusions.

Example 3

Identification of the Regions of the muNS Protein which are Specifically and Efficiently Recruited into the Inclusions Formed by muNS.

In this example, taking the previously mentioned assays as the starting point, the authors decided to check whether different muNS domains are capable of being incorporated into the cytoplasmic inclusions formed by the whole protein, to check which of them are directly involved in the interaction between muNS monomers.

To perform this study, the muNS protein was first divided into 5 regions described in Example 2. Said regions or domains are: N-terminus region (residues 1-448), Coil1 or C1 (residues 448-477), Intercoil or IC (residues 477-542), Coil2 or C2 (residues 539-605) and C-Tail or CT (residues 605-635) (FIG. 4).

These domains were expressed fused to the HA epitope of the influenza virus at its carboxyl end to enable differentiating their expression from that of the whole muNS protein by means of immunofluorescence with anti-HA epitope antibodies. The analysis by Western-blot using polyclonal anti-muNS antibodies revealed that most of the proteins are well expressed and that they have the size expected for each of the mutants (data not shown). The domains Coil1 and C-Tail were not expressed individually nor fused to HA at its carboxyl end nor at its amino end. To enable analyzing the interaction between these two domains with the muNS inclusions, other domains which were correctly expressed were added to these domains, in order to compare whether its presence influences mutant recruitment. The muNS(1-477)-HA mutant, where the Coil1 was added to the N-terminus region, and the muNS(539-635)-HA mutant, where the C-Tail was added to the Coil2, were thus generated.

Figure 4:
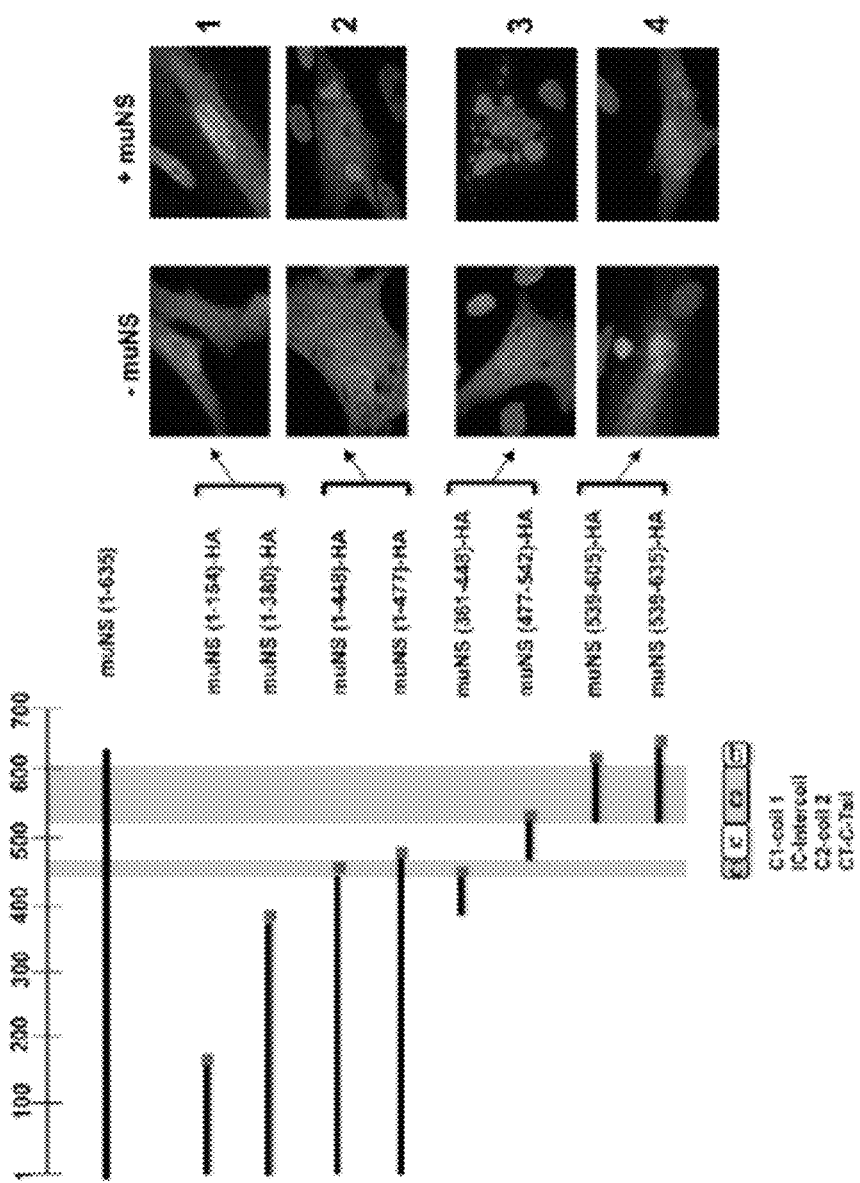
FIG. 4 describes different deletions of the muNS protein and its incorporation into inclusion bodies formed by the whole protein. muNS protein is schematically depicted by a black horizontal line covering residues 1-635 (top numbered positions). muNS mutants, with the HA fused at its C-terminus end, are shown as black lines covering approximately the muNS portion that they represent. The epitope HA is depicted as a square. The coiled-coil domains are depicted as vertical gray bars. A diagram depicting the minimum fraction of muNS conserving the inclusion-forming capacity (muNS-Mi) is shown at the bottom of the diagram. The four constituent domains of muNS-Mi are depicted as rectangles (Coil 1 or C1; the Intercoil or IC; the Coil 2 or C2 and the C-tail or CT). Fluorescence microscopy images of CEF cells transfected with plasmids expressing the proteins indicated on the left (−muNS) or co-transfected with those same plasmids and pCINeo-muNS (+muNS), are shown on the right of the figure. The cells were fixed at 24 h.p.t. and were then subjected to indirect immunofluorescence with polyclonal anti-influenza virus HA epitope antibody followed by a Cy3-conjugated secondary antibody. The nuclei were stained with DAPI.

Analysis by immunofluorescence revealed that, when expressed alone, all the muNS mutants were distributed in a diffused manner throughout the cytoplasm and nucleus (FIG. 4, photographs on the left). Furthermore, the fusion of HA at the carboxyl end does not seem to influence mutant intracellular distribution since it coincides precisely with the distribution in its absence (data not shown).

When a similar analysis was conducted in cells co-expressing muNS, the following results were obtained:

(i) The Intercoil domain comprising residues 477-542 is that which is incorporated more efficiently into the muNS inclusions, since the entire protein is detected in the inclusion bodies (FIG. 4, photographs on the right, line 3).

(ii) The N-terminus domain (muNS(1-448)) is incorporated into the inclusions, even though some of the protein was detected throughout the nucleus and cytoplasm (FIG. 4, photographs on the right, line 2). The region 1-477 (FIG. 4) had the same distribution pattern, i.e., fragment including the entire N-terminus region and Coil1 (FIG. 4, photographs on the right, line 2).

It is deduced from it that the first coiled-coil domain does not seem to be determinant in the incorporation into the inclusions and that in this region there is an interaction domain causing the incorporation thereof into the inclusions. The fragments of said region were then individually expressed in an attempt to locate said interaction domain. The mutants muNS(1-154)HA, muNS(1-380)HA and muNS (381-448)HA (FIG. 4) were thus grown.

The muNS(1-380) and muNS(1-154) regions were incorporated into the inclusions but poorly since much protein was detected throughout the nucleus and cytoplasm (FIG. 4, photographs on the right, line 1). However, the muNS(381-448) region was efficiently incorporated into the inclusions since the entire protein was detected in the inclusion bodies (FIG. 4, photographs on the right, line 3).

(iii) Coil2, residues 539 to 605, was also incorporated into the inclusions, even though it is not as efficient as the preceding regions since protein was detected both in the inclusion and throughout the cell and nucleus (FIG. 4, photographs on the right, line 4). Upon adding the C-Tail to this Coil2 to form the mutant muNS(539-635)-HA, it did not seem to influence the incorporation into the inclusions (FIG. 4, photographs on the right, line 4). This is a result contradicting the evidence shown in Example 2, where it was concluded that this C-Tail domain played a key role in orienting the contacts between the µNS monomers to form basla oligomers, thus controlling the shape of the inclusions and their formation efficiency. However, with the methodology used in this assay, the authors were not capable of detecting the participation thereof in the direct interaction between monomers.

Therefore, it can be concluded that the regions having a greater degree of specific interaction with the complete protein are the Intercoil (muNS(477-542)) and muNS(381-448) domains. On the other hand, the domains showing a lower degree of specific interaction are Coil2, C-Tail, and the N-terminus region of muNS between residues 1 to 380. Another less important region from the interaction viewpoint according to these results is the first coiled-coil or Coil1 (residues 448-477), since its deletion does not seem to influence the incorporation into the inclusions ((muNS(1-477) is incorporated as efficiently as muNS(1-448) (FIG. 4, photographs on the right, line 2). Likewise, the authors concluded that this tagging can be used for: i) sequestrating proteins in the inclusions; ii) purifying active proteins simply; iii) detecting intracellular protein-protein interactions. On the other hand, by means of adding different nuclear localization signals, this system can be adapted for generating nuclear inclusions and as a result of tagging with the mentioned domains, these inclusions can be used for: i) sequestrating nuclear proteins and ii) detecting the interaction between nuclear proteins in vivo.

Example 4

Incorporation of GFP in the Inclusions Through the Binding of Some muNS Domains.

Experiments were then performed to check if some of the muNS domains was capable of dragging an exogenous protein into the inclusions formed by the whole protein without affecting the integrity thereof. To that end, the GFP protein was fused to the amino-terminus end of the different muNS domains. The use of the fluorescent protein facilitates chimera detection and indicates if the protein associated with the inclusions is correctly folded. Analysis by Western-blot with polyclonal anti-muNS antibodies revealed that the proteins expressed have the size expected for each construct (data not shown). In the case of GFP chimeras were generated and detected with all the individual muNS domains. All the mutants shown in FIG. 5 were thus constructed.

Figure 5:
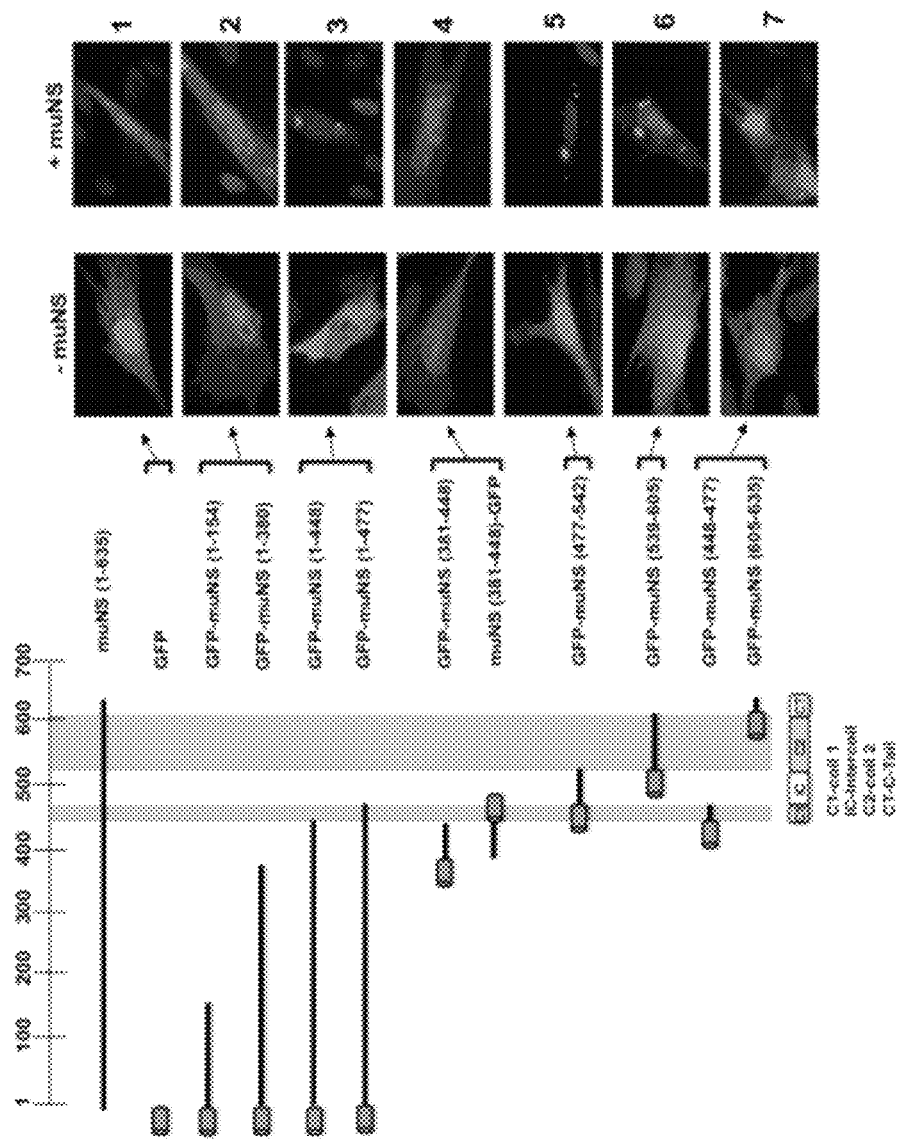
FIG. 5 shows the fusions of GFP to different domains of the muNS protein and its incorporation into inclusions formed by the whole muNS protein. The muNS protein as well as its chimaeras are depicted according to the same rules as in FIG. 1. GFP protein is depicted as a barrel. Fluorescence microscopy images of CEF cells transfected with plasmids expressing the proteins indicated on the left of the panels (−muNS) or co-transfected with the same plasmids and pCINeo-muNS (+muNS), are shown on the right. The cells were fixed at 24 h.p.t. and were then directly viewed with a fluorescence microscope. The nuclei were stained with DAPI.

Analysis by fluorescence microscopy revealed that GFP and all the fusion proteins were distributed in a diffused manner throughout the cell in the absence of muNS inclusions (FIG. 5, photographs on the left). A similar analysis was then conducted in cells co-expressing muNS. Only GFP protein continued to be distributed in a diffused manner throughout the entire cell, despite the fact that a small part was detected in the muNS inclusions (FIG. 5, photographs on the right, line 1), which indicated that GFP, even though it was not excluded from the inclusions, it was not incorporated into same. Similar results were obtained with the chimeras GFP-muNS(1-154) and GFPmuNS(1-380), GFP-Coil1 (muNS(448-477)) and GFP-C-Tail (muNS(605-635)) (FIG. 5, photographs on the right, lines 2 and 7). These results correspond with those obtained in Example 3, where it was shown that these areas were not efficiently incorporated into the inclusions.

The chimera containing the N-terminus region GFP-muNS(1-448) was efficiently incorporated into the inclusion bodies, even though some of the protein was detected throughout the nucleus and cytoplasm (FIG. 5, photographs on the right, line 3). Upon adding Coil1 to said chimera, generating the GFP-muNS(1-477) construct (FIG. 5, photographs on the right, line 3), it did not change the incorporation pattern, coinciding with the previously mentioned results. As seen previously, the GFP-muNS(1-380) chimera was not incorporated into the inclusions, whereas the muNS (381-448) region fused with GFP was not recruited as efficiently into the inclusions as expected, since it was detected both in the inclusion and throughout the cell (FIG. 5, photographs on the right, line 4). This could be due to the fact that the GFP blocks/conceals the area of interaction between the fragment with muNS. To solve this, the GFP was fused at its C-terminus end and this new chimera was also not efficiently incorporated into the inclusions (FIG. 5, line 4). Therefore, it can be concluded that the presence of GFP protein, regardless of its position (C-terminus or N-terminus) disrupts the interaction between this domain and the inclusions, whereas it does not disrupt the entire N-terminus region of muNS (1-448).

The Intercoil domain fused with GFP was very efficiently incorporated into the inclusions formed by muNS since the entire GFP protein was detected in the inclusion bodies (FIG. 5, line 5).

The Coil2 domain from 539 to 605 fused with GFP was recruited into the inclusions even though not as efficient as the Intercoil, since protein was detected both in the inclusion and in the rest of the cell (FIG. 2, line 6).

Example 5

Identification of the Regions of the muNS Protein which are Specifically and Efficiently Recruited into the Inclusions Formed by muNS-Mi.

A similar study was then conducted to find the muNS domains which interact with the minimum region of muNS (muNS-Mi) which is capable of generating cytoplasmic inclusions. This region contains the domains Coil1, Intercoil, Coil2 and CTail.

Figure 6:
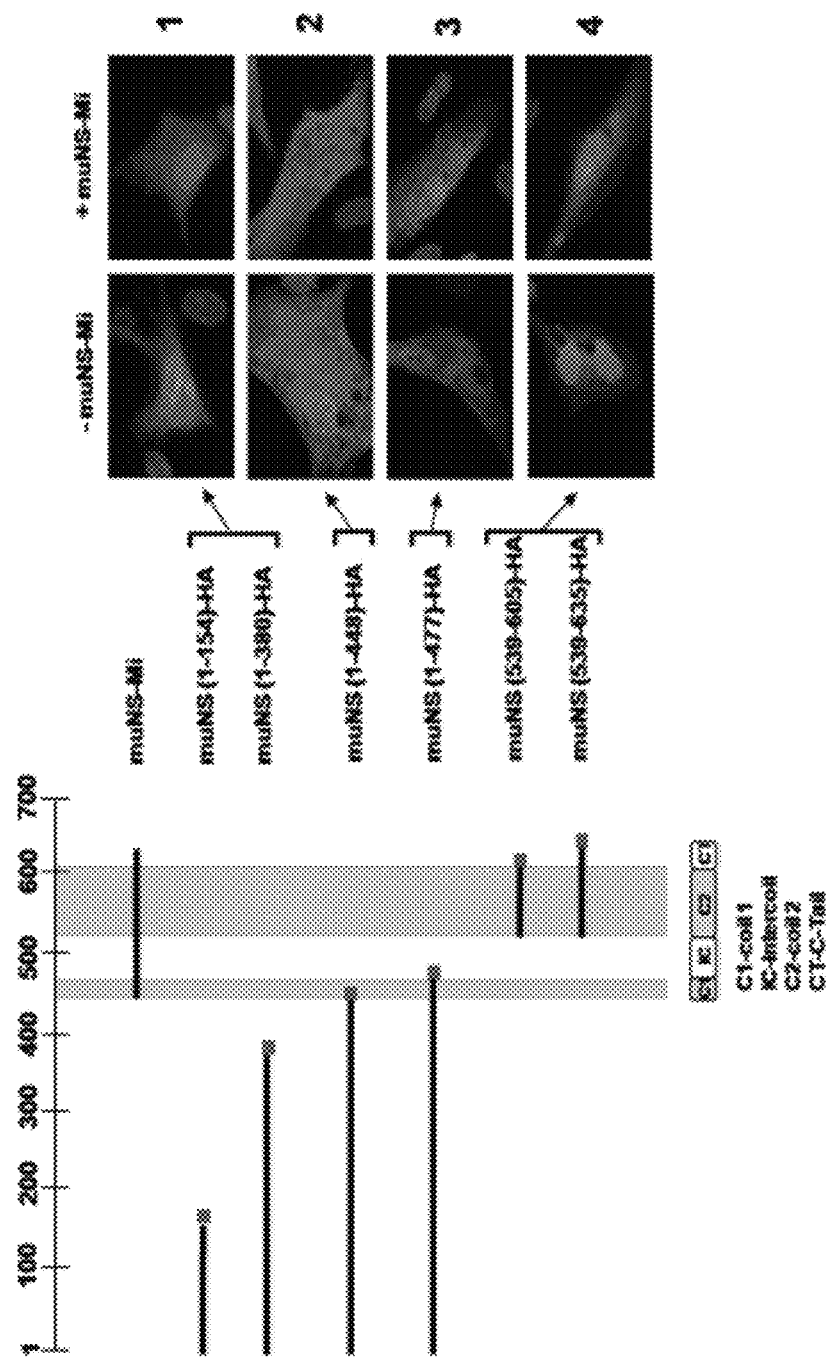
FIG. 6 describes deletions of the muNS protein and its incorporation into inclusions formed by the muNS-Mi protein. The muNS-Mi protein as well as the regions of muNS are depicted according to the same rules as in FIG. 1. Fluorescence microscopy images of CEF cells transfected with plasmids expressing the proteins indicated on the left of the panels (−muNS-Mi) or co-transfected with those same plasmids and pCINeo-muNS-Mi (+muNS-Mi), are shown on the right. The cells were fixed at 24 h.p.t. and were then subjected to indirect immunofluorescence with polyclonal anti-influenza virus HA epitope antibodies, followed by a Cy3-conjugated secondary antibody. The nuclei were stained with DAPI.

Unlike what happened when they were co-expressed with the whole protein, the constructs containing the N-terminus region of muNS were not incorporated into the muNS-Mi inclusions, since, even in their presence they were distributed in a diffused manner throughout the cell (FIG. 6, lines 1 and 2). Therefore, it is deduced that the amino-terminus region of muNS (1-448) does not interact with muNS-Mi and that its capacity to interact with muNS depends on the presence of an identical region in the inclusion-forming protein.

However, the region including the entire amino end and the first coiled-coil (muNS(1-477)) was indeed incorporated into the inclusions even though in a very inefficient manner (FIG. 6, line 3), which forms the first evidence that this domain is also involved in the muNS monomer-monomer interactions.

The Intercoil (muNS(477-542)) fused with HA cannot be detected when it was co-expressed with muNS-Mi. The only explanation for this result is that the HA epitope remains concealed inside the inclusions, and therefore the antibody cannot access the epitope and no signal is obtained.

The domain Coil2, i.e., the region 539 to 605 was incorporated into the inclusions, even though inefficiently, since protein was detected both in the inclusion and throughout the cell (FIG. 6, line 4). No improvement was seen upon adding the C-Tail to Coil2 (FIG. 6, line 4) which again indicated that this domain must not participate directly in the protein-protein interactions between muNS monomers.

Whether the different muNS domains were capable of directing the GFP protein to the muNS -Mi inclusions upon fusing them to the carboxyl end of the fluorescent protein was then checked. What was first performed as a control was co-expressing muNS-Mi with GFP and it was seen that the GFP protein continued to be distributed in a diffused manner throughout the cell, despite that a small part was detected in the inclusions (FIG. 7, line 1) which indicated that GFP alone is not incorporated into the inclusions. Similar results were obtained when co-expressing the GFP-C-Tail fusion with muNS-Mi (FIG. 7, right panels, compare lines 1 and 6), which corresponded with the results obtained in Example 4 and confirming that the C-terminus region does not seem to provide direct interaction between the muNS monomers.

Figure 7:
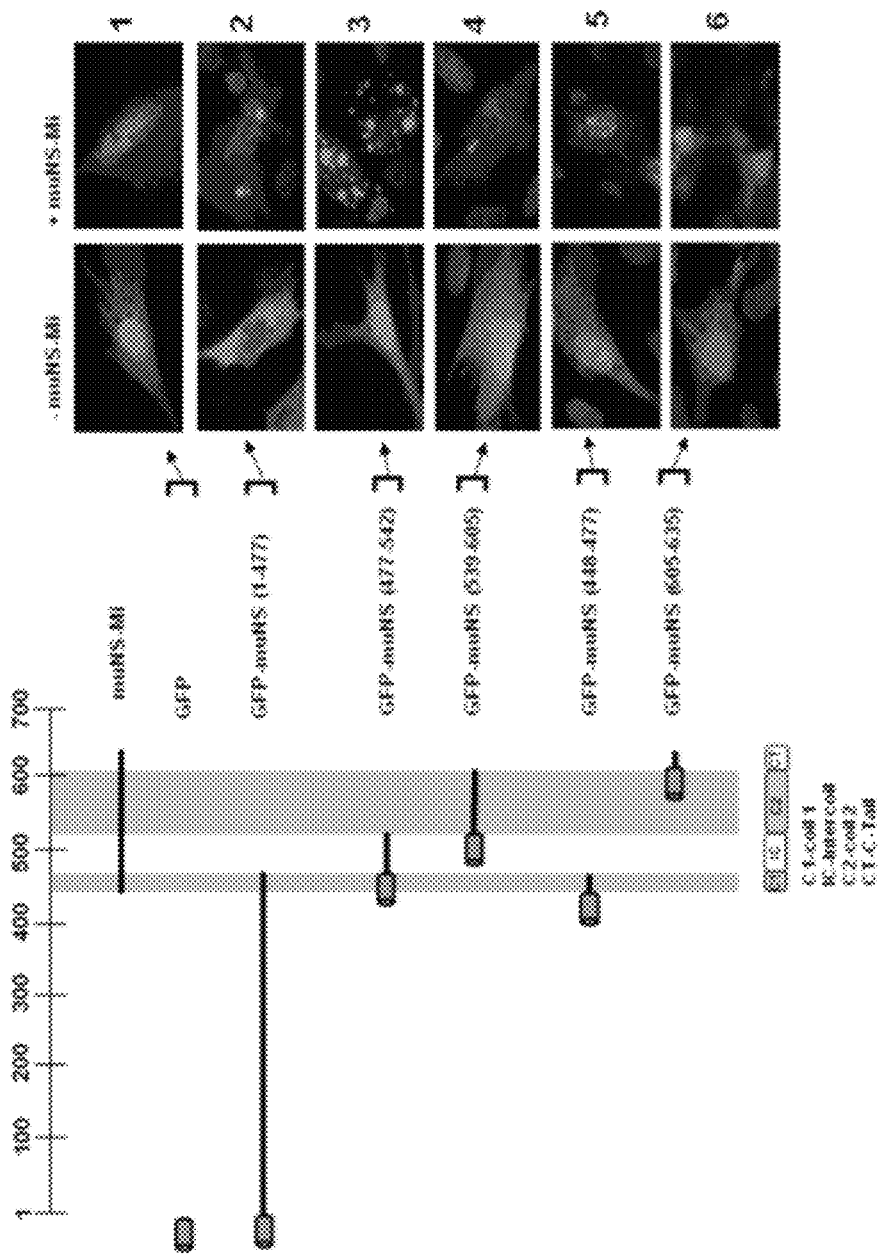
FIG. 7 shows the fusions of GFP to different domains of the muNS protein and its incorporation into inclusions formed by the muNS-Mi protein. The muNS-Mi protein as well as its chimaeras are depicted according to the same rules as in FIG. 1. The GFP protein is depicted as a barrel. Fluorescence microscopy images of CEF cells transfected with plasmids expressing the proteins indicated on the left of the panels (−muNS-Mi) or co-transfected with the same plasmids and pCINeo-muNS-Mi (+muNS-Mi), are shown on the right. The cells were fixed at 24 h.p.t. and were then viewed with a fluorescence microscope. The nuclei were stained with DAPI.

GFP-Coil1 (GFP-muNS(448-477)) was recruited into the inclusion bodies more efficiently than the GFP alone, even though a part of the protein was distributed throughout the cell (FIG. 7, right panels, compare line 1 with 5). The same occurred upon adding the Coil1 to the N-terminus region of muNS which did not interact with muNS-Mi, generating the GFPmuNS(1-477) chimera (FIG. 7, right panels, compare line 1 with 5). Similarly to what has been shown in Example 4, these results demonstrate that the Coil1 domain is recruited into the inclusions not very efficiently.

Once more, the 477-542 or Intercoil region fused with GFP was incorporated very efficiently into the inclusion bodies formed by muNS-Mi, since all the fluorescence was detected in the inclusions (FIG. 7, line 3).

Coil2 also recruited GFP into the inclusions, but not as efficiently as the Intercoil, since protein was detected both in the inclusion and throughout the cell (FIG. 7, line 4).

The results show that different domains of the muNS protein can be used as molecular tags for directing proteins into the inclusions formed by muNS-Mi. Similarly to the preceding example, the Intercoil domain seems to be the most suitable and the recruited protein (GFP) also does not lose its activity. Likewise, it can concluded that the muNS domains located towards the N-terminus end of the protein, specifically that located between residues 381-448 do not interact with muNS-Mi, whereas they do interact very efficiently with the complete protein.

Example 6

Method for Purifying Proteins Based on Recruiting Proteins into the Inclusions

Figure 8:
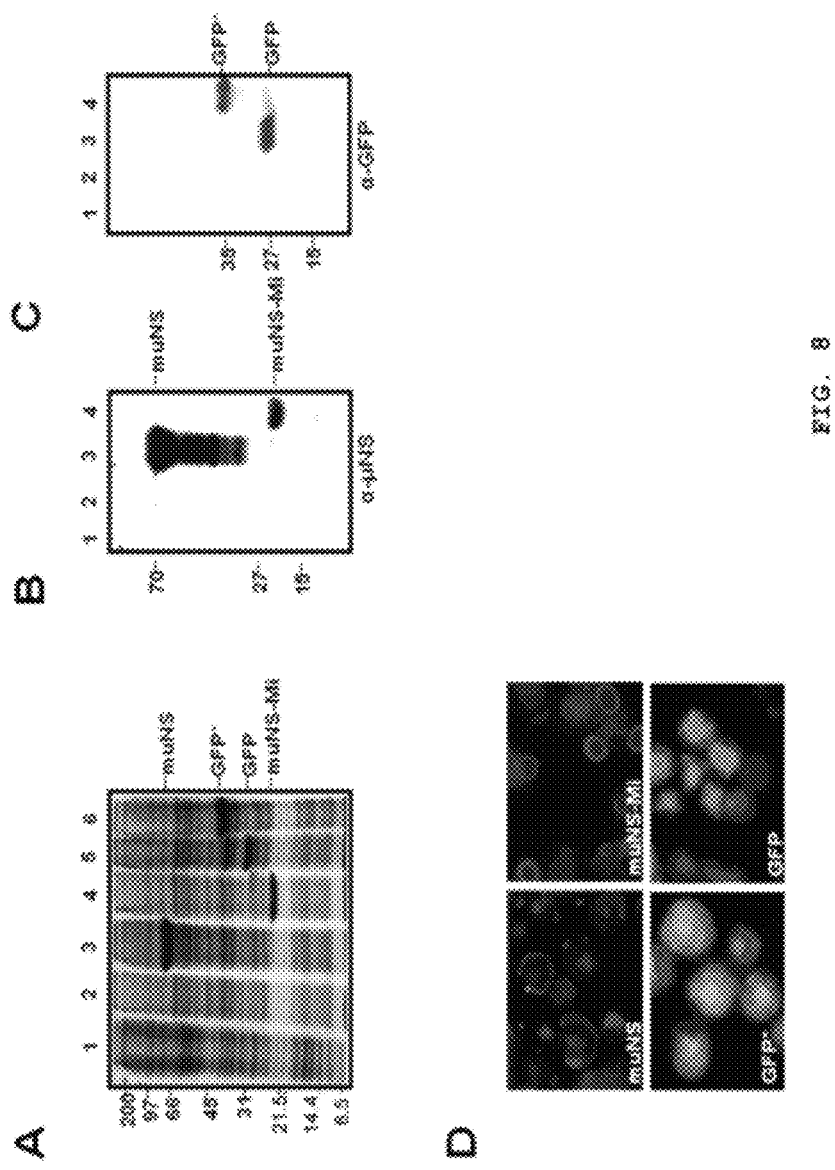
FIG. 8 shows the analysis of the baculovirus expression of muNS, muNS-Mi, GFP and GFP-Intercoil in Insect Sf9 cells. (A) 12.5% gel stained with Coomassie blue where samples corresponding to non-infected Sf9 cells (lane 1) or Sf9 cells infected with the following recombinant baculoviruses were run: Bac-Wt (lane 2) Bac-muNS (lane 3), Bac-muNS-Mi (lane 4), Bac-GFP (lane 5) and Bac-GFP-Intercoil (GFP *, lane 6). The samples were lysed at 72 h.p.i. in Laemmli buffer before subjecting them to electrophoresis. (B) Analysis of the lysates of non-infected Sf9 cells (lane 1), and Sf9 cells infected with Bac-Wt (lane 2), Bac-muNS (lane 3) or Bac-muNS-Mi (lane 4) by means of Western-blot using polyclonal anti-muNS antibodies. (C) Analysis of the lysates of non-infected Sf9 cells (lane 1), Sf9 cells infected with Bac-Wt (lane 2), Bac-GFP (lane 3) or Bac-GFP* (lane 4) by means of Western-blot using a monoclonal anti-GFP antibody. (D) Fluorescence microscopy images of Sf9 cells which had been infected with the following baculovirus: Bac-muNS, Bac-muNS-Mi, Bac-GFP and Bac-GFP-Intercoil (GFP*). The cells were fixed at 24 h.p.t. and were subjected to indirect immunofluorescence with polyclonal anti-muNS antibodies followed by an Alexa 488-conjugated secondary antibody (top panels) or were viewed directly with a fluorescence microscope, in the case of those expressing GFP (bottom panels). The nuclei were stained with DAPI.

Taking into account that: i) the cytoplasmic inclusions formed by the muNS proteins and muNS-Mi are capable of sequestrating active proteins when they are tagged with the Intercoil domain and ii) that it was shown that the inclusion bodies formed by muNS or muNS-Mi expressed in the baculovirus/insect cells system are easily purified conserving its structure (see Example 1), this system could be used as a simple method for purifying proteins. The generation of the recombinant baculoviruses which expressed the muNS-Mi and muNS proteins and the characterization of the expression thereof in insect cells have been described in Example 1 and are shown in FIG. 8.

For checking the method for purifying proteins, two new baculovirus were constructed: one expressing GFP (Bac-GFP) and another expressing GFP fused to the Intercoil domain, with a target sequence for Xa factor protease separating both protein domains (Bac-GFP-Xa-Intercoil). The use of green fluorescent protein facilitated tracking the purification process and allowed easily checking the correct folding and functionality of the protein to be purified. Like in the case of muNS and muNS-Mi, the expression of GFP recombinant protein and GFP-Xa-Intercoil in insect cells was analyzed by means of electrophoresis and Western-blot at 72 h.p.i. As shown in FIG. 8A, a protein of 30 kDa in size and another of 38 kDa were detected in the extracts of insect cells infected with the corresponding recombinant baculoviruses (lanes 5 and 6), but not in the extracts of cells non-infected (lane 1) or infected with wild-type baculovirus (lane 2). Furthermore, these proteins were recognized by monoclonal anti-GFP antibody (FIG. 8C). Both GFP and GFP-Xa-Intercoil showed a diffused distribution throughout the cell (FIG. 8D, bottom panels).

Figure 9:
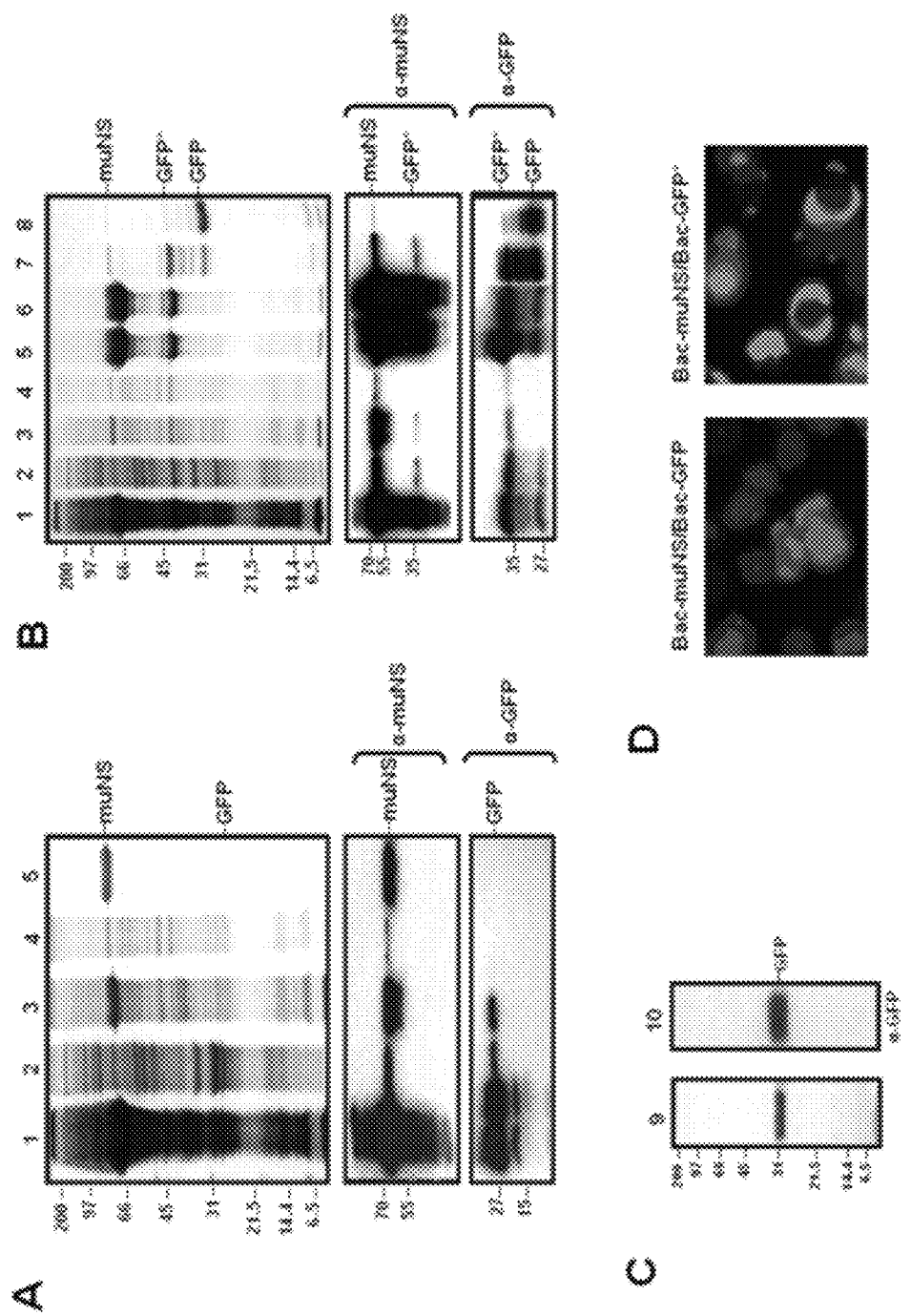
FIG. 9 describes the expression and purification of GFP-Intercoil as a result of its integration into inclusions formed by muNS. (A) Expression, purification and analysis by means of Western-blot of muNS inclusions co-expressed with GFP. The Sf9 cells co-infected with Bac-muNS and Bac-GFP were lysed at 72 h.p.i. in a hypotonic buffer and the resulting cell extract (lane 1) was fractioned by centrifugation into pellet and supernatant (lane 2). The pellet was washed twice in the hypotonic buffer, resuspended in the same volume of hypotonic buffer and sonicated. The sonicated extract (lane 3) was centrifuged and fractioned into pellet and supernatant (lane 4). The pellet was washed and centrifuged five times (lane 5). All the samples were run in a 12.5% polyacrylamide gel stained with Coomassie blue. Samples from each of the purification steps were analyzed by means of Western-blot using polyclonal anti-muNS antibodies (central panel) or a monoclonal anti-GFP antibody (bottom panel). The position of muNS and GFP is indicated on the right of the panels and that of the molecular markers is indicated on the left. (B) Expression, purification and analysis of GFP-Intercoil co-expressed with muNS by means of Western-blot. The first steps of purification were performed such as indicated above. The pellet washed and resuspended in salt (lane 5) was centrifuged and the supernatant (lane 6) was passed through a desalting column. The eluate was centrifuged and the supernatant (lane 7) was incubated with Xa factor (lane 8). All the samples were run in a 12.5% gel stained with Coomassie blue (top panel). Samples from each of the purification steps were analyzed by means of Western-blot using polyclonal anti-muNS antibodies (central panel) or a monoclonal anti-GFP antibody (bottom panel). The position of muNS and GFP is indicated on the right of the panels and that of the molecular markers is indicated on the left. (C) GFP purification: The extract incubated with Xa factor (9B, lane 8) was centrifuged and the supernatant was loaded in a Q-sepharose column. The eluted protein was concentrated and analyzed by means of SDS-PAGE (lane 9) and Western-blot using monoclonal anti-GFP antibody (lane 10). (D) Fluorescence microscopy images of Sf9 cells co-infected with BacmuNS/Bac-GFP or with Bac-muNS/Bac-GFP-Intercoil (Bac-GFP*). The cells were fixed at 24 h.p.t. and were viewed directly with a fluorescence microscope. The nuclei were stained with DAPI.

(A) Method for Purifying Proteins Based on Recruiting Proteins into the Inclusions Formed by the muNS Protein The protocol which was used for purifying the inclusion bodies containing the GFP protein tagged with the Intercoil domain was that described in the Section of "Methods" of the examples of the present specification, which prevented the use of detergents and high salt concentrations. To check the purification system, Sf9 insect cells were co-infected with the recombinant baculoviruses which expressed the proteins: muNS (Bac-muNS) and GFP-Intercoil (Bac-GFP-Intercoil) (FIG. 9B) control. The cells were co-infected with the baculovirus which expressed muNS proteins (Bac-muNS) and GFP (Bac-GFP) (FIG. 9A) as a negative control. At 72 hours post-infection, the cells were centrifuged for 10 minutes at 1000×g, after which they were resuspended in 10 ml of hypotonic buffer (10 mM Hepes pH 7.9, 10 mM KCl, 5 mM $MgCl_2$) and kept in ice for 15 minutes to facilitate their lysis. The total extract, which is shown in lane 1 of FIGS. 9 (A and B), was centrifuged at 2000×g for 10 minutes and the supernatant loaded in lane 2 of FIGS. 9 (A and B). The resulting pellet was washed several times more (see section of Methods) and was finally resuspended in 10 ml of hypotonic buffer and sonicated to break the nuclei and fragment the DNA. The sonicated extract (FIGS. 9A and B, lane 3) was centrifuged at 200×g a pellet and a supernatant (FIGS. 9A and B, lane 4) being obtained. The pellet was washed several times until obtaining the purified extract as shown in lane 5 of FIGS. 6A and 6B. In all cases, the identity of the proteins expressed was confirmed by means of Western-blot using anti-muNS antibodies (FIGS. 9A and 9B, intermediate panels) and anti-GFP antibodies (FIGS. 9A and 9B, bottom panels).

How most of the tag-free GFP protein is released from the supernatant after cell lysis (lane 2) is seen in the negative control (FIG. 9A). Traces of GFP remaining in the pellet were removed completely in the washings performed in the purification process, which can be observed in the Western-blot performed with anti-GFP antibodies (FIG. 9A, bottom panel, compare lanes 2, 3, 4 and 5). In contrast, the GFP protein tagged with the Intercoil domain (FIG. 9B, GFP*) was firmly associated with the muNS inclusions since the most remained associated with muNS in the final purified pellet (FIG. 9B, lane 5).

These results were confirmed by means of analyzing the cells by fluorescence microscopy (FIG. 9D). Therefore, it was observed that the tagged GFP protein (right panel) was clearly associated with the inclusions formed by the muNS protein, whereas this did not occur with untagged protein (left panel).

In order to purify the GFP-Intercoil protein, the muNS inclusions contained in the final pellet were dismantled by incubation with 500 mM NaCl. The sample resuspended in salt was centrifuged for 5 minutes at 16,000×g to remove the insoluble residues and the supernatant (FIG. 9B, lane 6) was passed through a desalting column to allow the reassociation of the muNS monomers and the subsequent release of GFP-Intercoil. The eluate was centrifuged for 5 minutes at 16,000×g to remove insoluble residues, it being maintained with the supernatant (FIG. 9B lane 7) which barely contained muNS protein (FIG. 9B compare lane 7 with lane 6), and which contained the GFP-Intercoil protein and some secondary bands which corresponded with the fragments from Intercoil degradation, since they were detected with the monoclonal anti-GFP antibody (FIG. 9B lane 7, bottom panels). The salt-free extract was then incubated with the Xa factor to release GFP from its binding to the Intercoil (FIG. 9B lane 8, top panel), which was confirmed by means of Western-blot, (FIG. 9B lane 8, bottom panel). For the purpose of completing the purification and removing the residues from muNS, Intercoil and protease, the extract shown in lane 8 of FIG. 9B was passed through a Q-sepharose column pre-equilibrated with 20 mM Tris-HCl pH 8. The column was eluded with increasing NaCl concentrations and the fractions collected were analyzed by SDS-PAGE, GFP being detected in the elution of 400 mM of NaCl (data not shown). Finally, the fractions containing GFP were concentrated and the sample was analyzed by SDS-PAGE, a single band of 30 kDa being observed (FIG. 9B, left panel) which was confirmed as GFP (FIG. 9B, right panel) by means of Western-blot.

Figure 10:
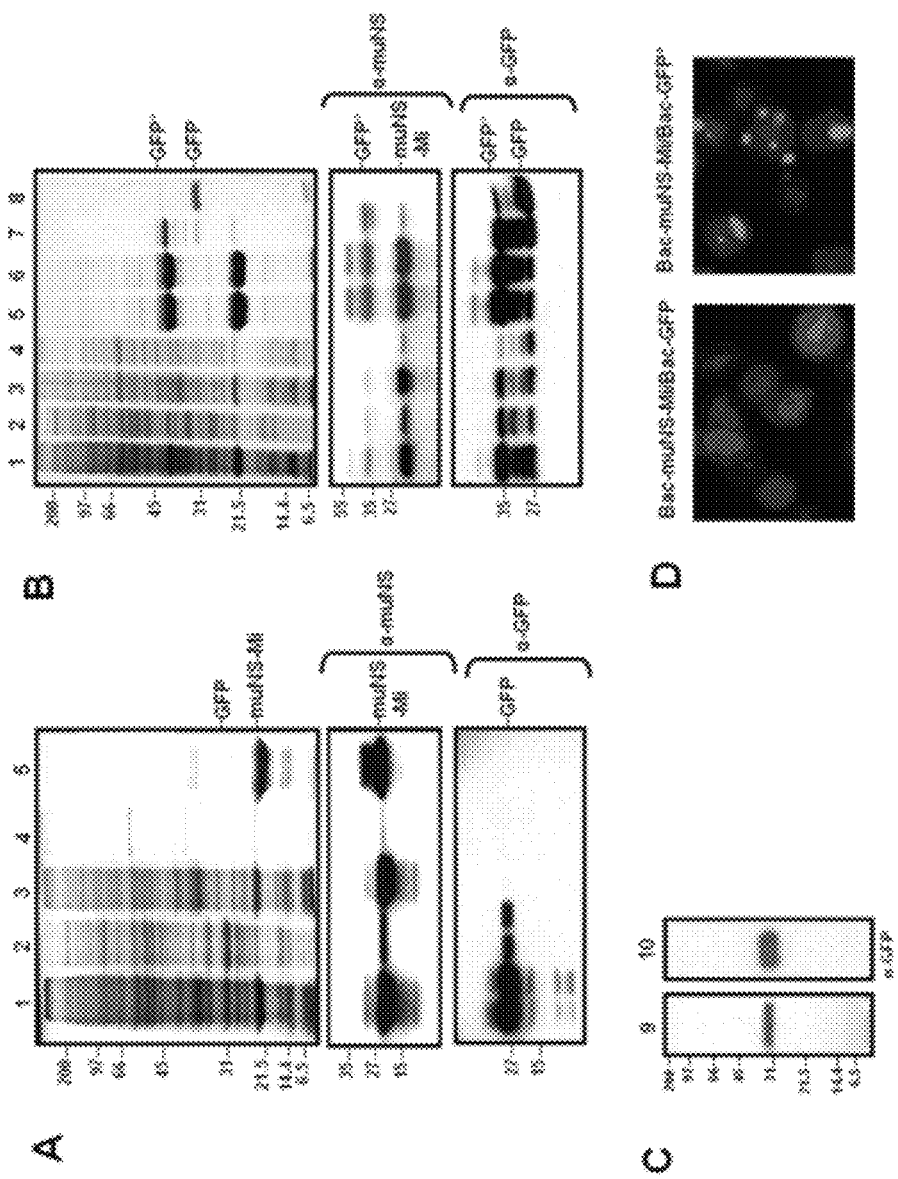
FIG. 10 describes the expression and purification of GFP-Intercoil as a result of its integration into inclusions formed by muNS-Mi. The distribution of the figure and of its samples is completely similar to that described for FIG. 9. The only difference lies in the use of muNS-Mi (FIG. 7) instead of muNS (FIG. 5).

(B) Method for Purifying Proteins Based on Recruiting Proteins into the Inclusions Formed by the muNS-Mi Protein As has been shown previously, the Intercoil domain is also capable of directing proteins to the inclusions formed by muNS-Mi. Therefore, the inventors decided to test the protein purification system with these inclusions which are smaller and more compact than those forming the whole muNS protein. Therefore, an alternative system for adapting to hypothetical proteins which may be purified with the muNS inclusions, or the size of which is similar to that of muNS could become available. To analyze this purification system, exactly the same method as with the whole protein was carried out and the results are shown in FIG. 10, the distribution of which is exactly the same as FIG. 9 in order to facilitate the analysis thereof. In this case, the tag-free GFP protein was also used as a negative control (FIG. 10A) and the chimera GFP-Intercoil (FIG. 10B) was purified. The results obtained were identical to those already described for the whole muNS protein. Therefore, the tag-free GFP protein did not associate with the inclusions, whereas protein tagged with Intercoil was easily purified. Similarly, the purified inclusions were dismantled with salt and the tagged protein was easily recovered in native conditions. These results show that both types of inclusions form the base of a simple and efficient protein purification system.

(C) Method for Purifying Proteins Based on Removing Divalent Ions in the Hypotonic Buffer The purification protocol described in the section of "Methods" and used by the authors of the invention consists of treating the pellets obtained from the cell lysis for 15 minutes with a buffer A (10 mM Hepes pH 7.9, 10 mM KCl), i.e., the same as the hypotonic buffer removing the magnesium. Most of the muNS protein (FIG. 11A, lane 1) is thus solubilized. Nevertheless, upon adding 5 mM of magnesium to the soluble muNS protein again, the latter reforms aggregates which can be easily recovered by centrifugation (FIG. 11B). The same result was obtained with the rest of the versions of muNS forming inclusions (FIG. 11A, lanes 2 to 4). Likewise, the same magnesium effect was obtained with other divalent ions, such as Cd, Ca, Co, Cu, Fe, Mn, Ni, Sr and Zn (results not shown), which were also capable of causing the formation of muNS aggregates in vitro.

Figure 11:
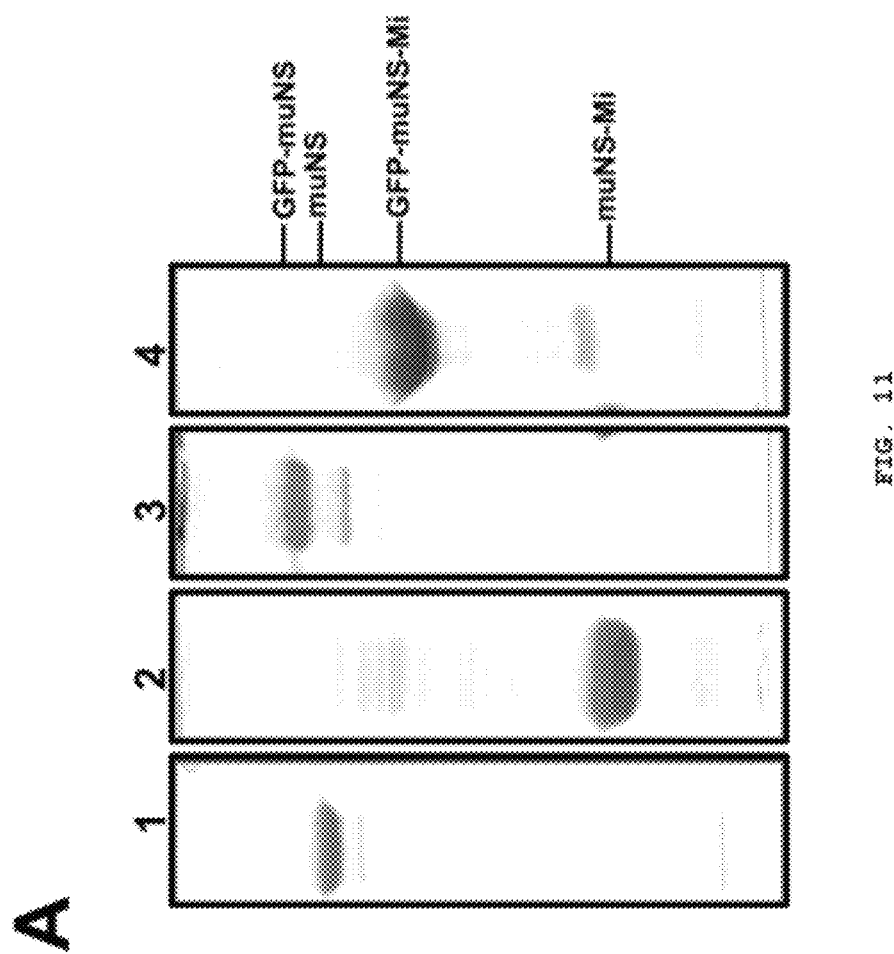
FIG. 11 describes the effect of magnesium on the solubility of muNS and derivatives. (A) polyacrylamide gel stained with Coomassie, where the purification of muNS (lane 1) or its derivatives muNS-Mi (2), GFP-muNS (3) or GFP-muNS-Mi (4) by solubilization due to the absence of magnesium, as described in the text, is shown. (B) Descriptive diagram of the method for purifying, solubilizing in the absence of divalent ions and reconstructing muNS inclusions and derivatives.
Figure 11:
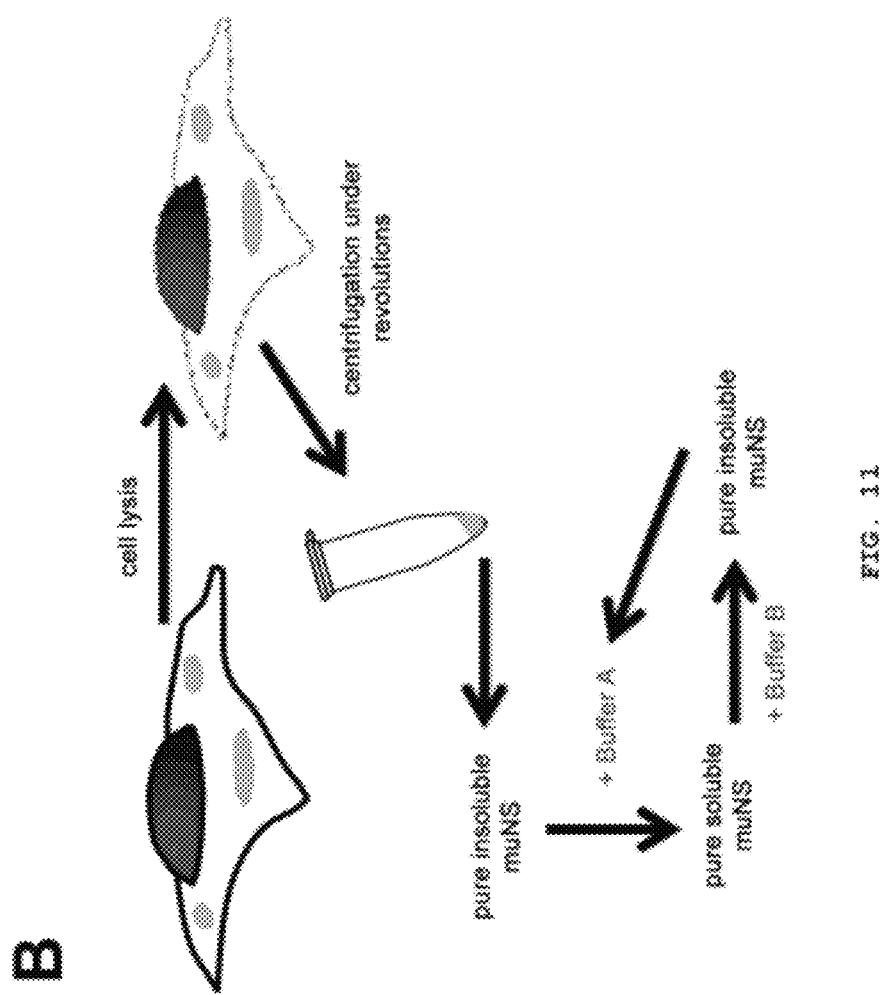
Figure 12:
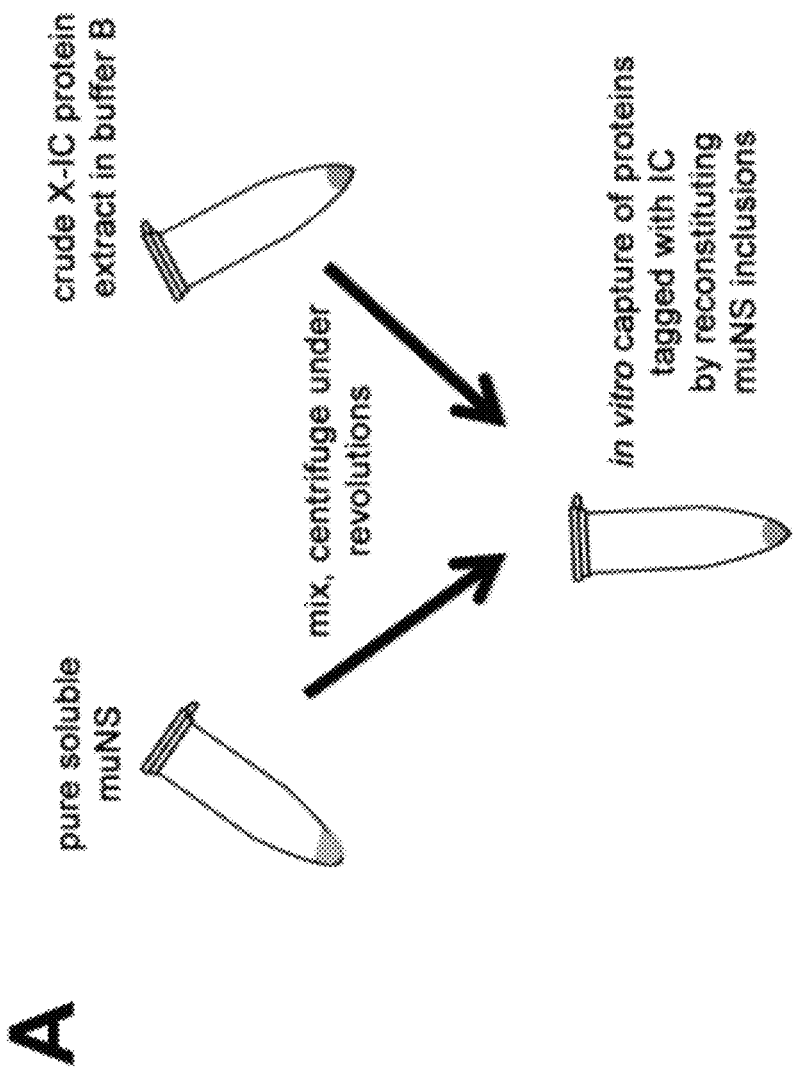
FIG. 12 describes the in vitro intake of proteins tagged with the IC domain. (A) Explicative diagram of the intake strategy as explained in the text. (B) Soluble extracts (s/n lane of the gel) of GFP or GFP-IC in buffer B (as indicated in the top part of the figure), were mixed with magnesium-free soluble muNS (lanes 1 and 3) or its derivatives in identical conditions (mNS-Mi, lanes 5 and 7; GFP-muNS, lanes 9 and 11; GFP-muNS-Mi, lanes 13 and 15). The reconstituted inclusions were washed several times in buffer A and are shown in lanes "p" for muNS or its derivatives, as indicated in the top part of the figure.
Figure 12:
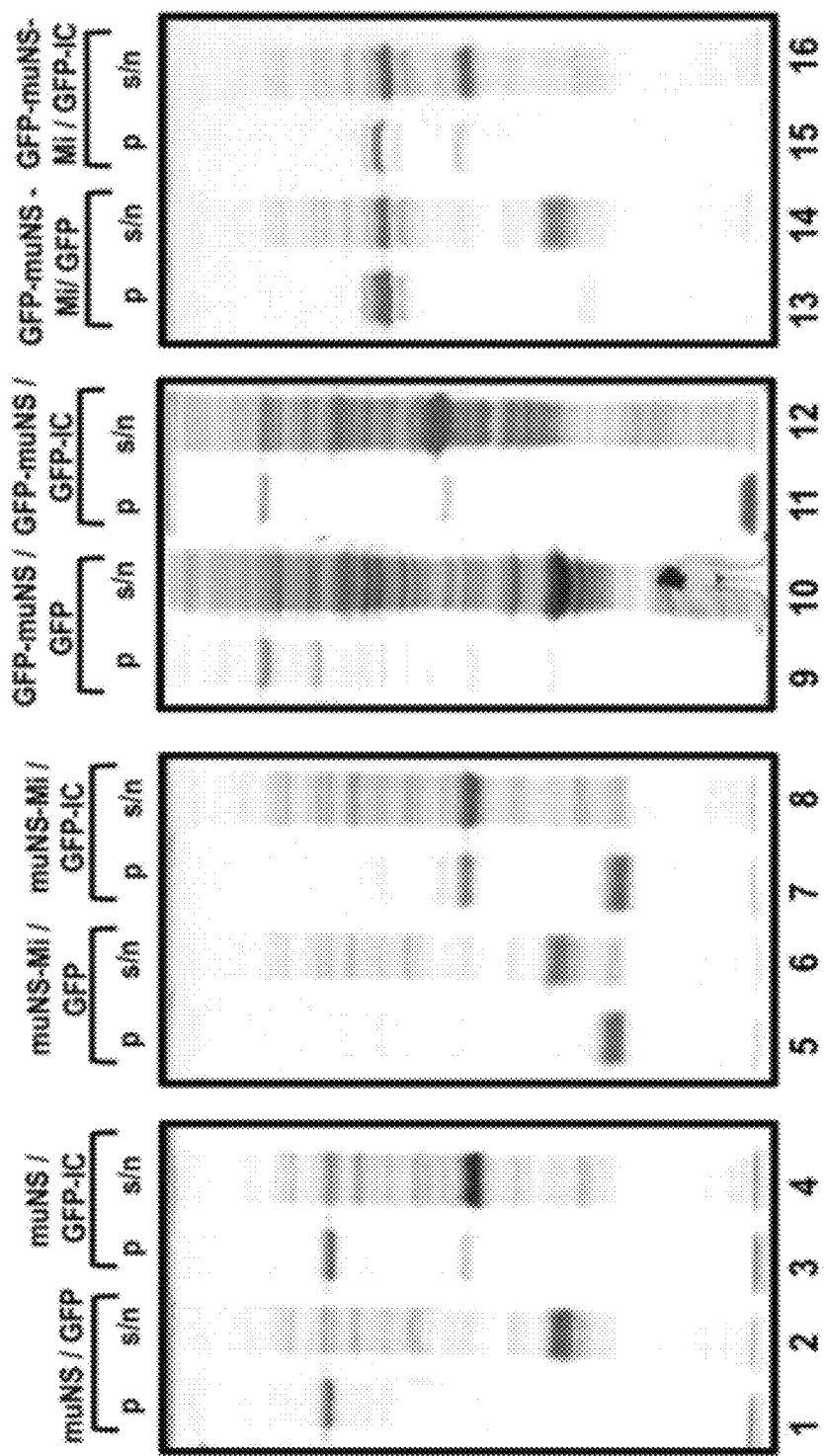

The results shown in FIG. 11 immediately suggest a possible in vitro method for purifying proteins tagged with the Intercoil domain which is schematically described in FIG. 12B. The method consists of mixing the inclusions formed by muNS (or muNS derivatives) solubilized in the absence of magnesium (buffer A) with crude extracts from cells where the polypeptide of interest tagged with the Intercoil domain has been expressed and which have been lysed in the presence of magnesium (buffer B). Upon mixing both extracts, the presence of magnesium in buffer B causes the formation of muNS aggregates capturing only those proteins which have been tagged with the Intercoil domain by affinity.

Upon experimentally testing the validity of the strategy described in FIG. 12A with the four versions of muNS (muNS, muNS-Mi, GFP-muNS and GFP-muNS-Mi), it is confirmed that: (i) the reconstitution of inclusions does not capture the GFP protein or other cell proteins (FIG. 12B, lanes 1, 5, 9, 13); (ii) the presence of the Intercoil domain (IC) induces the in vitro capture of GFP by the reconstituted inclusions (FIG. 12B, lanes 3, 7, 11, 15) and (iii) even though the four different versions of muNS are capable of capturing GFP tagged with IC by means of this method, muNS-Mi has a better efficiency (FIG. 12B, lane 7).

The in vitro method described herein can have on some occasions advantages over the in vivo capturing method. Specifically, if wanting to "decorate" the inclusions with several proteins, for example, for generating multi-epitope vaccines, expressing each protein individually is much more effective. This is because when co-expressing several proteins with the baculovirus method in the same cells, the promoters of the baculovirus compete for the cell polymerase and subsequently the mRNAs compete for the ribosomes. However, all the cell resources are fully available to those proteins which are expressed alone. Furthermore, this system can be used for performing "pull-down" by performing in vitro capture of proteins tagged with IC which have been expressed in any cell system in order to purify them and to analyze other proteins which co-purify with the tag.

Example 7

Figure 13:
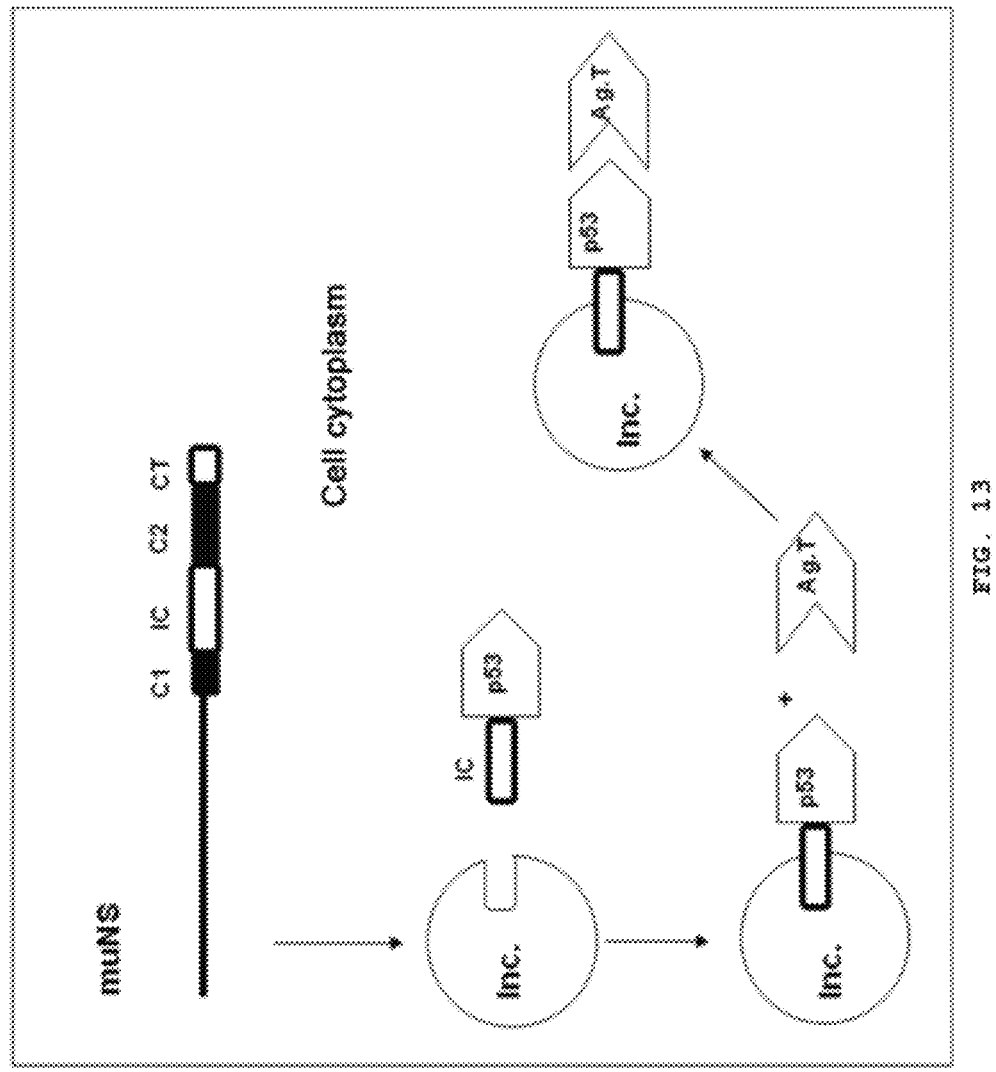
FIG. 13 describes the strategy used for generating muNS inclusions as a platform for detecting protein associations inside eukaryotic cells. The muNS protein is depicted schematically by a black horizontal line, followed by the four domains present in the C-terminus region (muNS-Mi) which are depicted as rectangles (the Coil 1 or C1; the Intercoil or IC; the Coil 2 or C2 and the C-tail or CT). The muNS protein forms inclusions (Inc.) in the cell cytoplasm and would incorporate therein p53 tagged with the Intercoil (IC) region. The p53-Intercoil held in the inclusions would act as a bait for recruiting its ligand, the SV40 T-antigen (Ag.T).

Method for Detecting the Interaction Between Proteins in the Cytoplasm of Eukaryotic Cells Being able to direct the proteins of interest to the inclusions formed by muNS and muNS-Mi has several potential applications in addition to protein purification. One of these applications is to identify interactions between proteins inside eukaryotic cells. Therefore, if a protein of interest is tagged with the Intercoil domain for directing it to the inclusion bodies, it could attract other proteins interacting strongly therewith and relocating them in the inclusions in the absence of a tag. To check the efficiency of said method the SV40 p53-T-antigen system was used. These two proteins interact strongly with one another inside the cell and said interaction is very well characterized (Ali et al., 2001, Semin. Cancer Biol. 11, 15-23). In fact, this pair forms the positive control of other methods well known for detecting interactions between proteins such as the "Two-Hybrid" system (Clontech). The protein p53 was thus tagged with the Intercoil domain and it was able to be checked: i) whether the p53 protein tagged with Intercoil is efficiently recruited into the muNS inclusions and ii) whether it is capable of attracting its common ligand, the SV40 T-antigen, to the inclusions (see FIG. 13).

(A) Recruitment of p53-Intercoil by the muNS Protein and its GFP-Fused Version

The first step for developing the system was to construct a plasmid expressing human p53 protein fused at its carboxyl end to the Intercoil domain, p53-Intercoil being obtained. The identity of said construct was confirmed by means of sequencing its expression plasmid and by means of analyzing the lysates of CEF transfected cells with this plasmid by Western-blot using anti-muNS and anti-p53 antibodies (data not shown).

Figure 14:
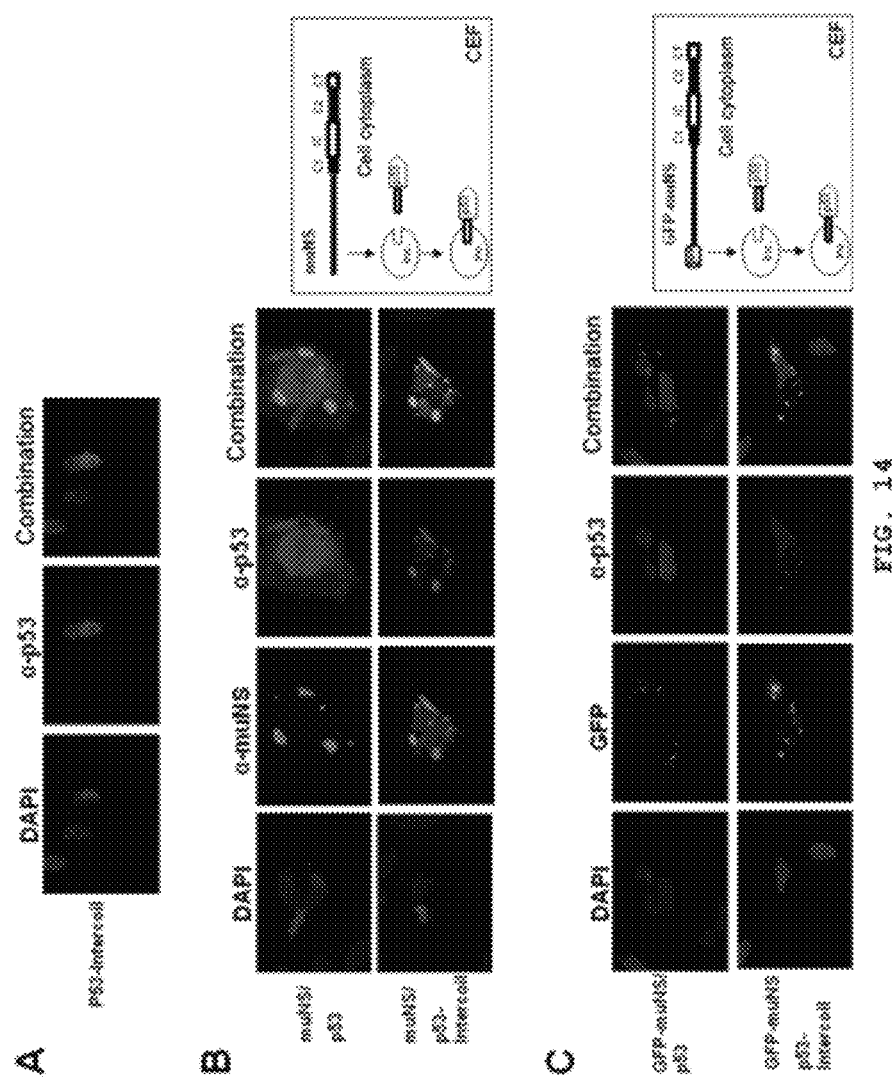
FIG. 14 describes the intracellular distribution of p53 or p53-Intercoil in the presence of the inclusions formed by muNS or GFP-muNS in CEF cells. (A) Subcellular localization of p53-Intercoil. The semi-confluent CEF cells were transfected with plasmid expressing the chimaera p53-Intercoil. (B) Subcellular localization of p53 or p53-Intercoil in the presence of inclusions formed by muNS. (C) Subcellular localization of p53 or p53-Intercoil in the presence of inclusions formed by GFPmuNS. In (A), (B) and (C) the semi-confluent CEF cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

For determining the intracellular distribution of p53-Intercoil, CEF cells were transfected with the plasmid p53-Intercoil, fixed for 24 h and analyzed by immunofluorescence using anti-p53 antibodies. p53-Intercoil fusion protein was mainly localized in the nucleus, which is the common localization of p53 (FIG. 14A). This result shows that the fusion of the Intercoil domain to the carboxyl end of p53 does not modify its intracellular localization. The proteins p53 and muNS were then co-expressed and their intracellular distribution was analyzed by means of immunofluorescence. The p53 protein was mainly localized in the nucleus and not in the cytoplasmic inclusions formed by muNS (FIG. 14B, top panels). This result shows that: i) p53 does not associate with the inclusion bodies and; ii) the specific anti-p53 antibody does not recognize the inclusions. However, in the cells which co-expressed p53-Intercoil and muNS, p53 was mainly localized in the inclusions, even though in may cells a small part of p53 remained in the nucleus (FIG. 14B, bottom panels).

The experiment was then repeated using GFP-muNS instead of muNS, since it has the advantage that antibodies are not required for detecting the inclusions and through the earlier work it is known that the fusion of GFP protein did not affect the formation of inclusions by muNS. Such as in the case above, p53 remained in the nucleus when it was co-expressed with GFP-muNS, which shows that: i) p53 does not associate with the GFP-muNS inclusions and; ii) the specific anti-p53 antibody recognizes the inclusions formed by GFP-muNS (FIG. 14C, top panels). However, in the cells co-expressing p53-Intercoil and GFP-muNS, p53 was mainly localized in the inclusions (FIG. 14C, bottom panels), showing, like in the case above, that the incorporation of p53 into the inclusions formed by GFP-muNS did not affect the integrity thereof.

(B) Binding Endogenous SV40 T-Antigen to the Inclusion-Bound p53-Intercoil

Whether tagging p53 with the Intercoil domain and its subsequent relocalization in the muNS inclusions also caused the relocalization of known ligands of the p53 protein was then checked. To that end, Cos-7 cells having integrated therein a copy of the SV40 genome and therefore express the SV40 T-antigen (Ag.T) (Gluzman, 1981, Cell, 23: 175-82) which is mainly localized in the nucleus (Kalderon et al., 1985, Cell 39: 499-509), were used.

Figure 15:
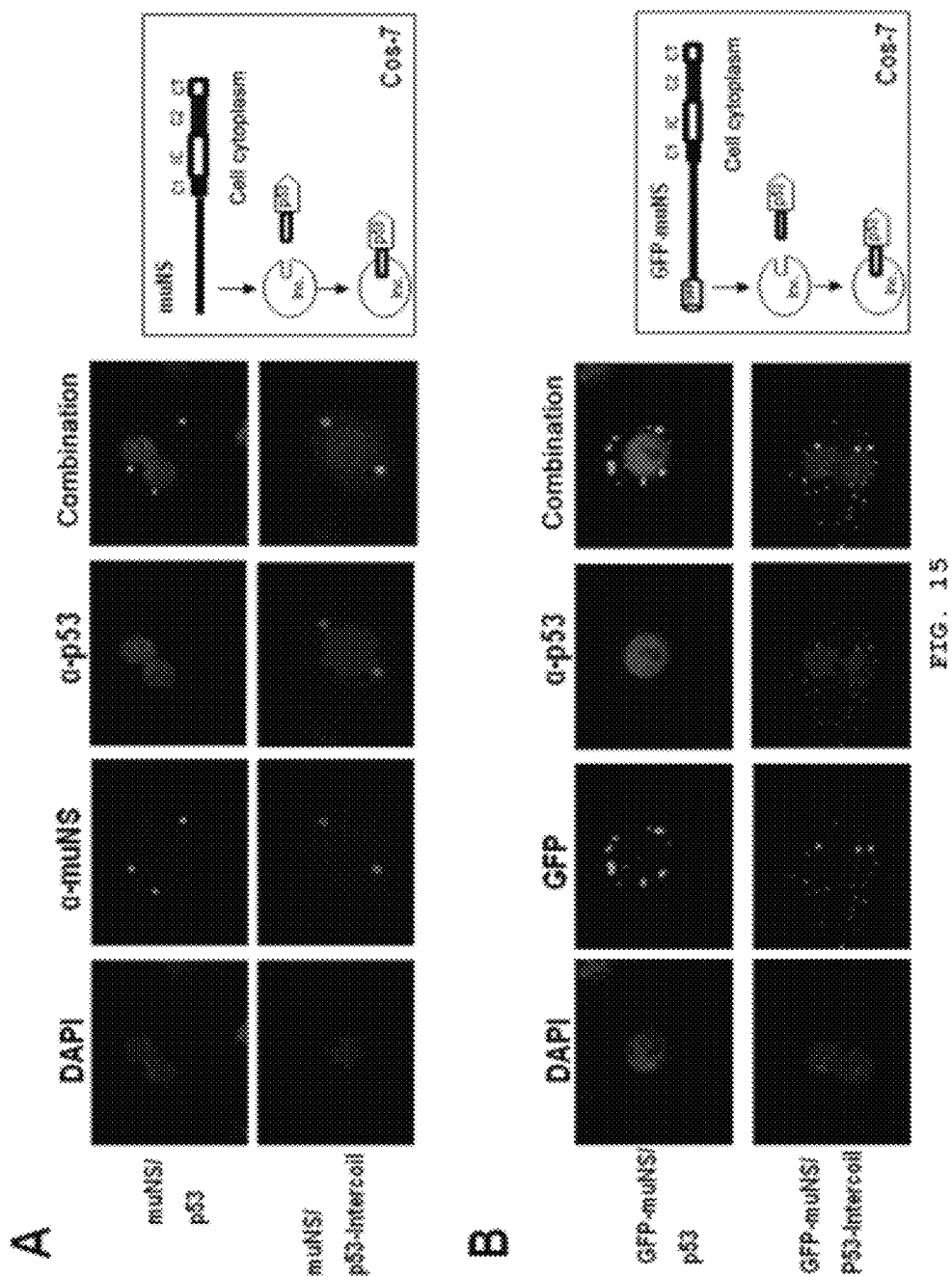
FIG. 15 describes the intracellular distribution of p53 or p53-Intercoil in the presence of the inclusions formed by muNS or GFP-muNS in Cos-7 cells. (A) Subcellular localization of p53 or p53-Intercoil in the presence of inclusions formed by muNS. (B) Subcellular localization of p53 or p53-Intercoil in the presence of inclusions formed by GFP-muNS. Semi-confluent Cos-7 cells were transfected with the plasmids expressing the proteins indicated on the left of the figure. In (A) and (B), the cells were fixed at 24 h.p.t. and were then subjected to indirect immunofluorescence with a monoclonal anti-p53 antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

The p53 protein was exclusively localized in the nucleus of the Cos-7 cells when it was co-expressed with muNS (FIG. 15A, top panels) or with GFP-muNS (FIG. 15B, top panels). However, p53-Intercoil was mainly localized in the inclusions formed by muNS or GFP-muNS (FIGS. 15A and 15B, bottom panels), which shows that the system for recruiting proteins into muNS inclusions works perfectly in different cell types.

Figure 16:
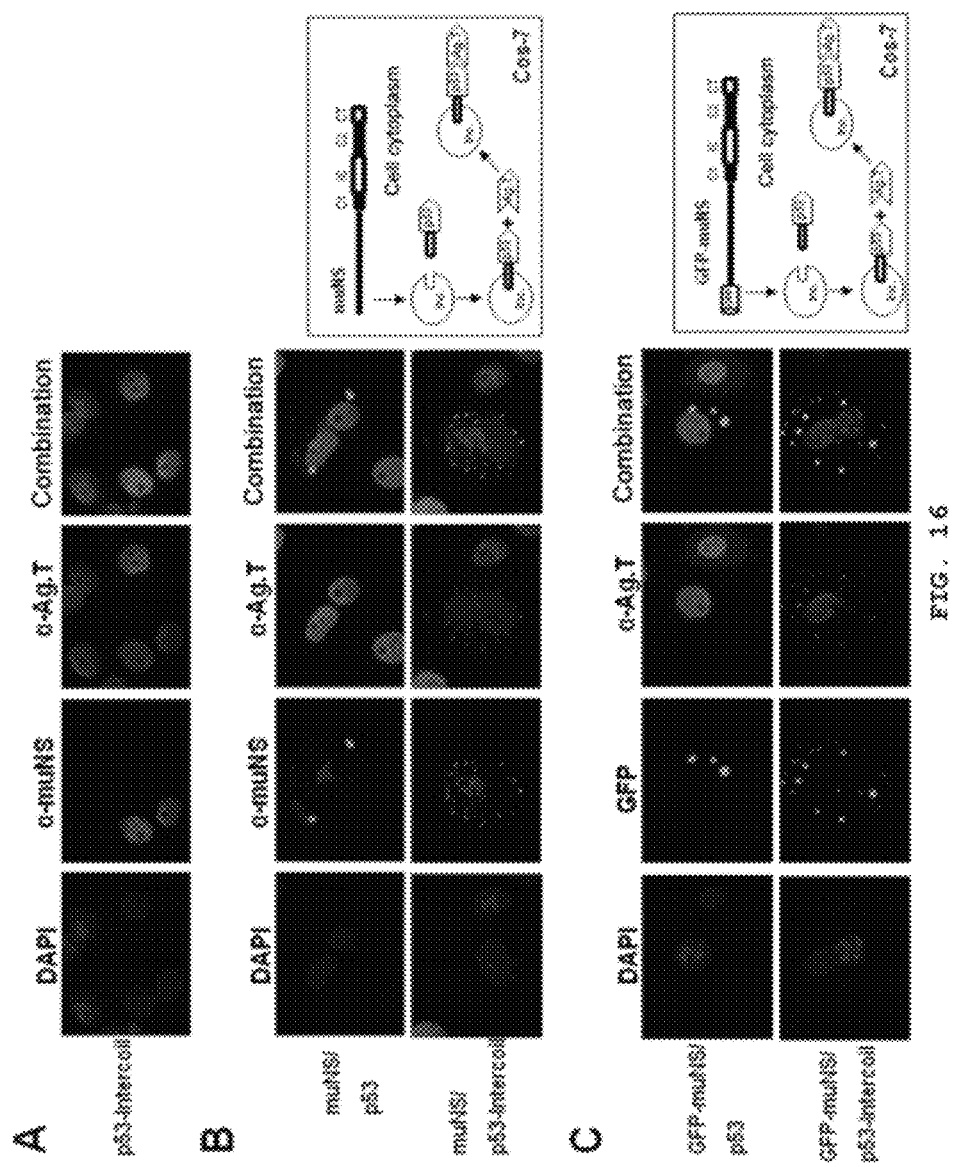
FIG. 16 describes the intracellular distribution of the SV40 T-antigen in the presence of muNS or GFP-muNS co-expressed with p53 or p53-Intercoil in Cos-7 cells. (A) Subcellular localization of p53-Intercoil and T-antigen in Cos-7 cells. (B) Subcellular localization of the T-antigen in cells co-expressing muNS and p53 or muNS and p53-Intercoil. (C) Subcellular localization of the T-antigen in cells co-expressing GFP-muNS and p53 or GFP-muNS and p53-Intercoil. In (A), (B) and (C), the semi-confluent Cos-7 cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody and polyclonal anti-muNS antibodies followed by an Alexa 488-conjugated secondary antibody, where appropriate. The GFP-muNS was viewed directly and the nuclei were stained with DAPI. A diagram of what is shown in the immunofluorescence images is depicted on the right of the panels according to the standards of the diagram of FIG. 13.

It was then confirmed that in the Cos-7 cells where p53 and muNS or GFP-muNS were expressed, the T-antigen was found exclusively in the nucleus, which is its common localization (FIGS. 16B and C, top panels). These results show that: i) T-antigen does not associate with the inclusions and ii) the specific anti-T-antigen antibody does not recognize the inclusions. However, in Cos-7 cells which expressed p53-Intercoil in the presence of muNS or GFP-muNS, T-antigen was mainly detected in the inclusions, despite that a small part remained in the nucleus (FIGS. 16B and C, bottom panels). This result shows that: i) T-antigen is recruited into the inclusions by association with p53; ii) the incorporation of the T-antigen into the inclusion bodies by association with p53 does not affect the integrity thereof; and iii) the system of tagging with Intercoil domain can be used as a platform to see whether two proteins interact with one another in the cytoplasm of eukaryotic cells, even when the test proteins are nuclear proteins.

Finally, as a control to show that the anti-T-antigen antibody does not recognize p53, the p53-Intercoil construct was expressed and detected using anti-muNS and anti-T-antigen antibodies. The expression of the p53-Intercoil construct was detected with anti-muNS antibodies due to the presence of the Intercoil domain, but the anti-T-antigen antibody did not generate any signal above the cellular background, therefore it can be concluded that the anti-T-antigen antibody does not recognize p53 (FIG. 16A).

(C) Binding Exogenous SV40 T-Antigen to Inclusion-Bound p53-Intercoil

Once it is shown that p53 is capable of attracting T-antigen endogenously expressed by the Cos-7 cells into the inclusions, whether the system also worked with the exogenous T-antigen (Ag.T) expressed by means transfecting CEF cells was investigated, since these cells do not express Ag.T. This has the added theoretical difficulty that three different plasmids must be put in the same cell. However, it is known that when performing co-transfections with several plasmids, the transfected cells tend to incorporate all the plasmids used or none of them. Currently there are many technical examples based on co-transfecting several plasmids, such as the two-hybrid system (Clontech) for mammalian cells, or the reverse genetic systems developed for reovirus, orbivirus, etc. (Boyce et al., 2008, J. Virol. 82: 8339-48).

Figure 17:
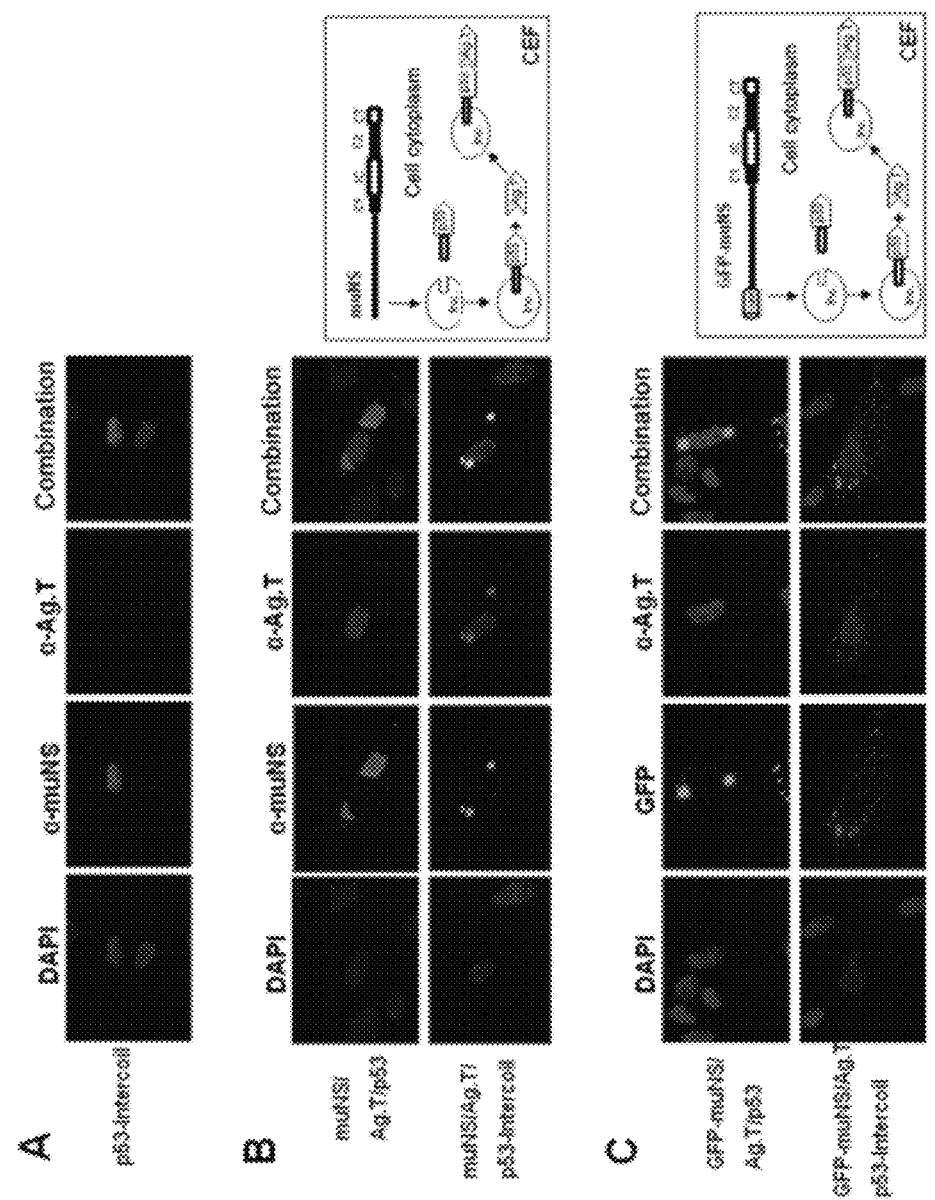
FIG. 17 describes the intracellular distribution of the SV40 T-antigen in the presence of muNS or GFP-muNS co-expressed with p53 or p53-Intercoil in CEF cells. (A) Subcellular localization of p53-Intercoil in CEF cells. (B) Subcellular localization of the T-antigen in cells co-expressing muNS and p53 or muNS and p53-Intercoil. (C) Subcellular localization of the T-antigen in cells co-expressing GFP-muNS and p53 or GFP-muNS and p53-Intercoil. In (A), (B) and (C), the semi-confluent CEF cells were transfected with the plasmid expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

Like the preceding case of Cos-7 cells, the T-antigen expressed from plasmids was localized exclusively in the nucleus of CEF cells wherein it was co-expressed together with muNS and p53 or with GFP-muNS and p53 (FIGS. 17B and C, top panels). However, upon replacing p53 with p53-Intercoil, the T-antigen became mainly localized in the inclusions (FIGS. 17B and C, bottom panels), which again shows the validity of this system for studying interactions between proteins which can be expressed endogenously by the cells used or by means of using recombinant plasmids.

Again, as a control to show that the anti-T-antigen antibody does not recognize p53, the p53-Intercoil construct was expressed and detected using anti-muNS and anti-T-antigen antibodies. As expected, p53-Intercoil reacted with anti-muNS but not with the anti-T-antigen antibody (FIG. 17A).

(D) Binding Endogenous SV40 T-Antigen to p53-Intercoil Bound to the Inclusions Formed by muNS-Mi Whether the system for detecting interactions between proteins also worked upon replacing muNS and GFP-muNS with muNS-Mi and GFP-muNS-Mi was checked so that an alternative system become available. To that end, the methodology to be followed was the same as that used for the case of muNS/GFP-muNS, i.e., the interaction between p53 with T-antigen was studied both in Cos-7 cells and in CEF cells.

Figure 18:
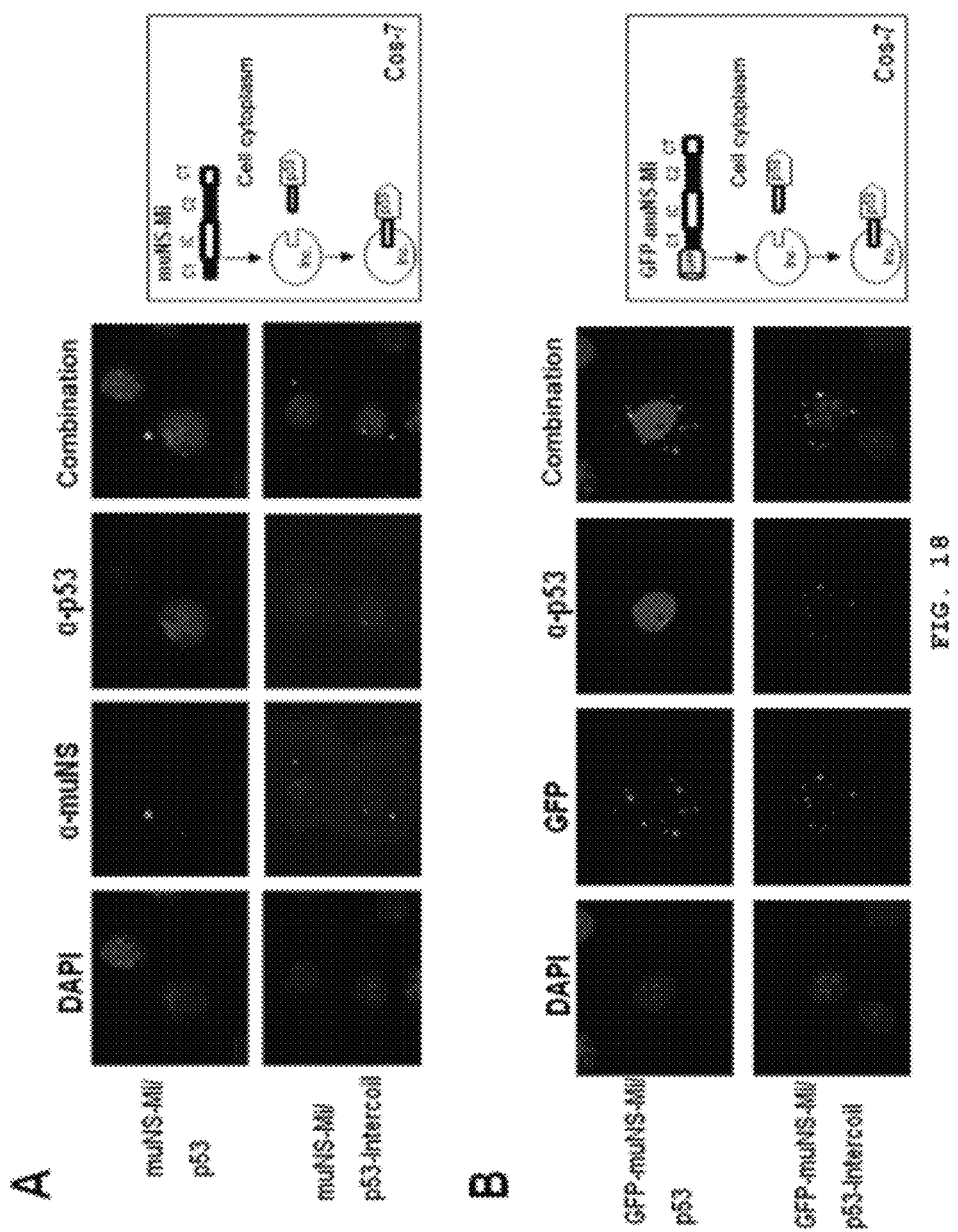
FIG. 18 describes the intracellular distribution of p53 or p53-Intercoil in the presence of the inclusions formed by muNS-Mi or GFP-muNS-Mi in Cos-7 cells. (A) Subcellular localization of p53 or p53-Intercoil in the presence of inclusions formed by muNS-Mi. (B) Subcellular localization of p53 or p53-Intercoil in the presence of inclusions formed by GFP-muNS-Mi. In (A) and (B), the semi-confluent Cos-7 cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

In terms of the endogenous antigen, such as in the case of muNS, p53 was detected exclusively in the nucleus of the Cos-7 cells and not in the inclusions formed by muNS-Mi in the cells which co-expressed muNS-Mi and p53 (FIG. 18A, top panels); showing that: i) p53 does not associate with the inclusion bodies formed by muNS-Mi and ii) the anti-p53 antibody does not recognize the inclusions formed by muNS-Mi. However, upon replacing p53 with p53-Intercoil, p53 was mainly localized in the inclusions (FIG. 18A, bottom panels), showing that its incorporation into the inclusion bodies did not affect the integrity thereof. It must be highlighted that in this case the presence of nuclear and cytoplasmic inclusions was observed, which can be due to the fact that the p53-Intercoil drags the muNS-Mi into the nucleus, due to its small size and to the presence of nuclear localization signals in p53. The process was then repeated using GFP-muNS-Mi, thus preventing the use of anti-muNS antibodies. As in the preceding case, p53 remained in the nucleus when it was co-expressed with GFP-muNS-Mi, which showed that: i) p53 does not associate with the inclusions and ii) the specific anti-p53 antibody does not recognize the inclusion bodies formed by GFP-muNS-Mi (FIG. 18B, top panels). Upon replacing p53 with p53-Intercoil, p53 was almost exclusively localized in the inclusions (FIG. 18B, bottom panels), showing that the incorporation of p53 into the inclusions formed by GFP-muNS-Mi did not affect the formation/integrity thereof.

Figure 19:
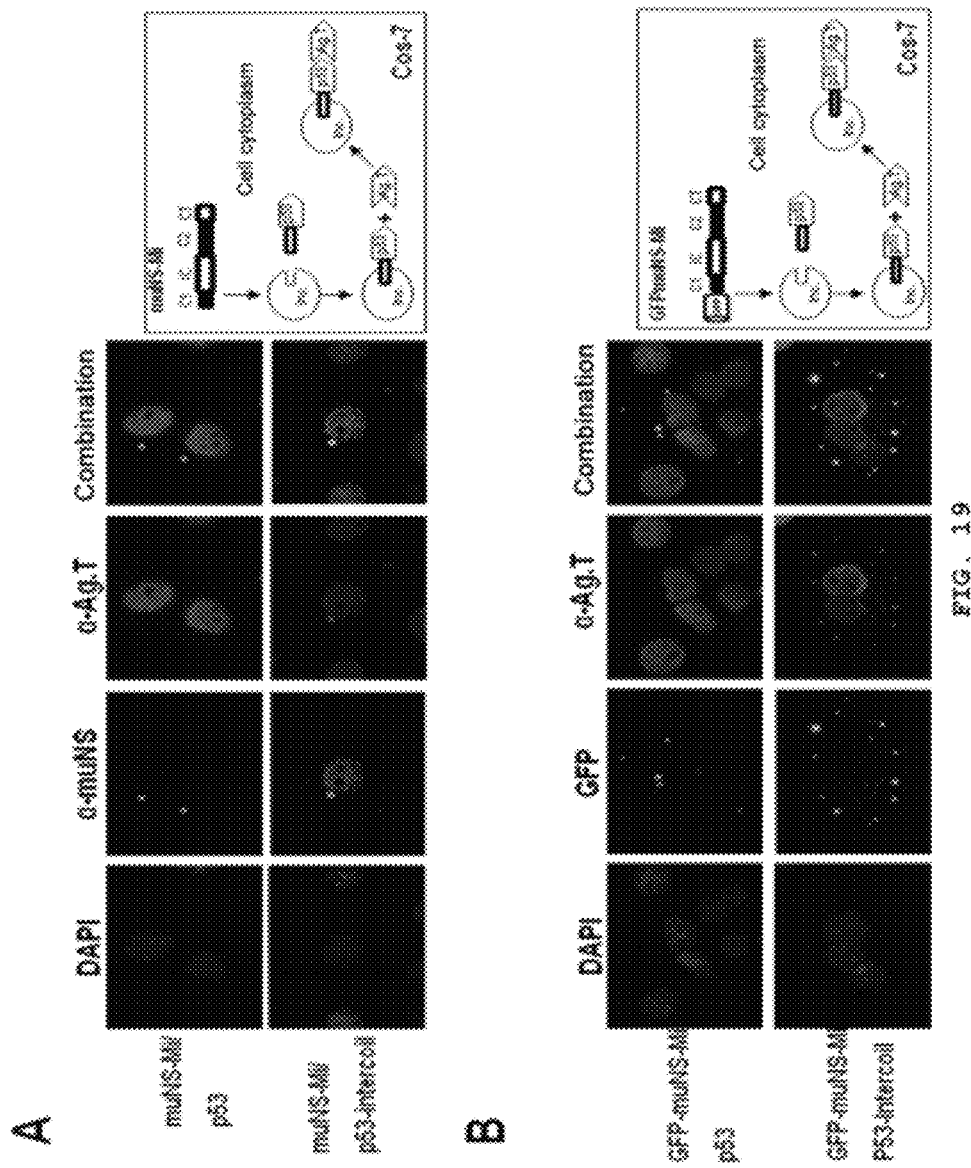
FIG. 19 shows the intracellular distribution of the SV40 T-antigen in the presence of muNS-Mi or GFP-muNS-Mi co-expressed with p53 or p53-Intercoil in COST cells. (A) Subcellular localization of the T-antigen in cells co-expressing muNS-Mi and p53 or muNS-Mi and p53-Intercoil. B-Subcellular localization of the T-antigen in cells co-expressing GFP-muNS-Mi and p53 or GFP-muNS-Mi and p53-Intercoil. In (A) and (B), the semi-confluent Cos-7 cells were co-transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

The distribution of Ag.T in Cos-7 cells where p53-Intercoil was expressed together with muNS-Mi or GFP-muNS-Mi was then analyzed. By expressing p53 in the presence of muNS-Mi or GFP-muNS-Mi, the T-antigen was localized exclusively in the nucleus (FIGS. 19A and B top panels); showing that: i) T-antigen does not associate with the inclusions formed by muNS-Mi and; ii) the specific anti-T-antigen antibody does not recognize the muNS inclusions-Mi. Nevertheless, upon replacing p53 with p53-Intercoil, the T-antigen became mainly localized in the inclusions (FIGS. 19A and B bottom panels). Like in the preceding case, some nuclear inclusions were observed upon using muNS-Mi. These results show that: i) the incorporation of the T-antigen into the inclusion bodies of muNS-Mi by association with p53 does not affect the integrity/formation thereof; and ii) the inclusions formed by muNS-Mi or GFP-muNS-Mi can be used as a platform to see whether two proteins interact with one another in the cytoplasm.

Figure 20:
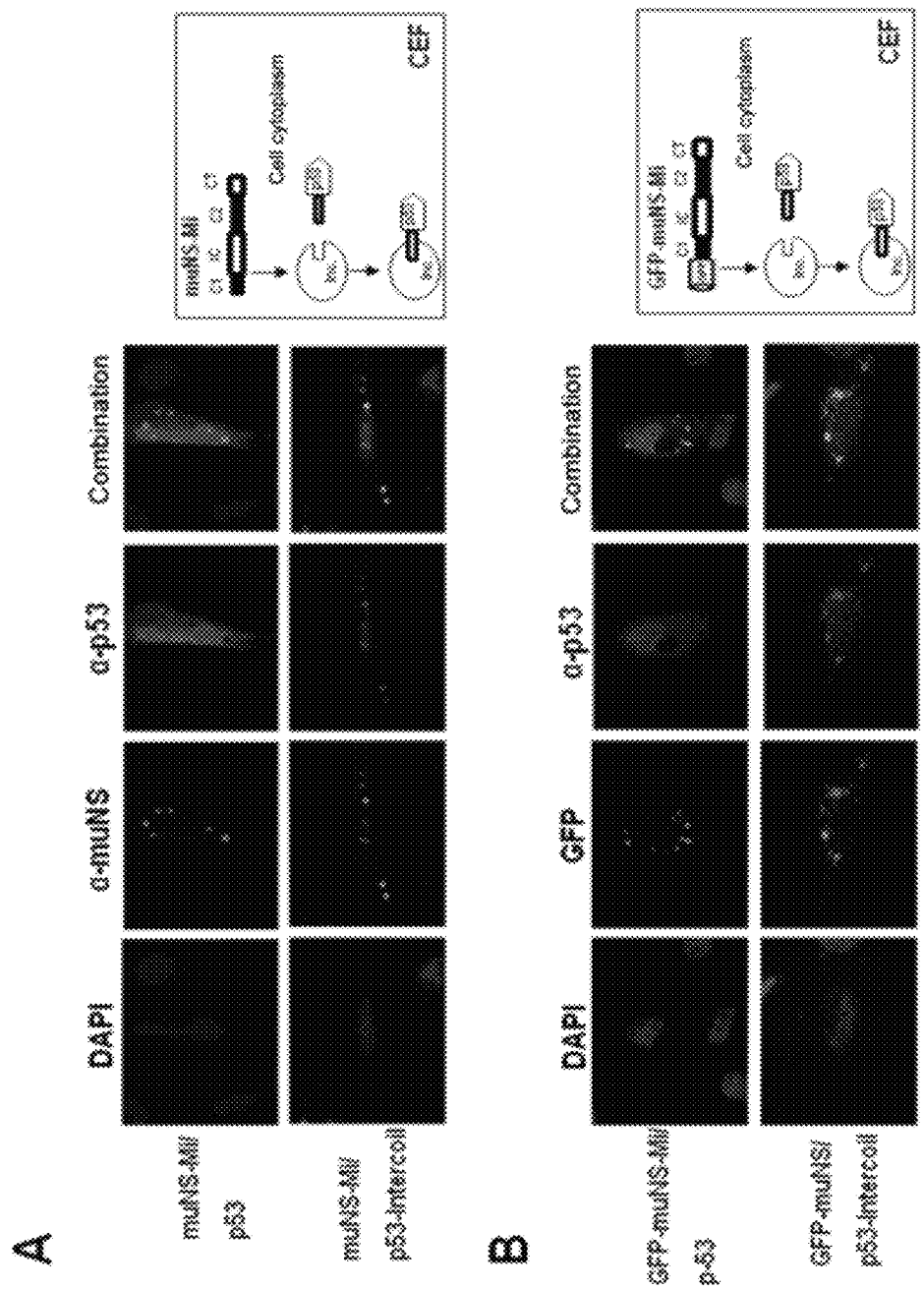
FIG. 20 shows the intracellular distribution of p53 or p53-Intercoil in the presence of the inclusions formed by muNS-Mi or GFP-muNS-Mi. (A) Subcellular localization of p53 or p53-Intercoil in the presence of inclusions formed by muNS-Mi. (B) Subcellular localization of p53 or p53-Intercoil in the presence of inclusions formed by GFP-muNS-Mi. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.
Figure 21:
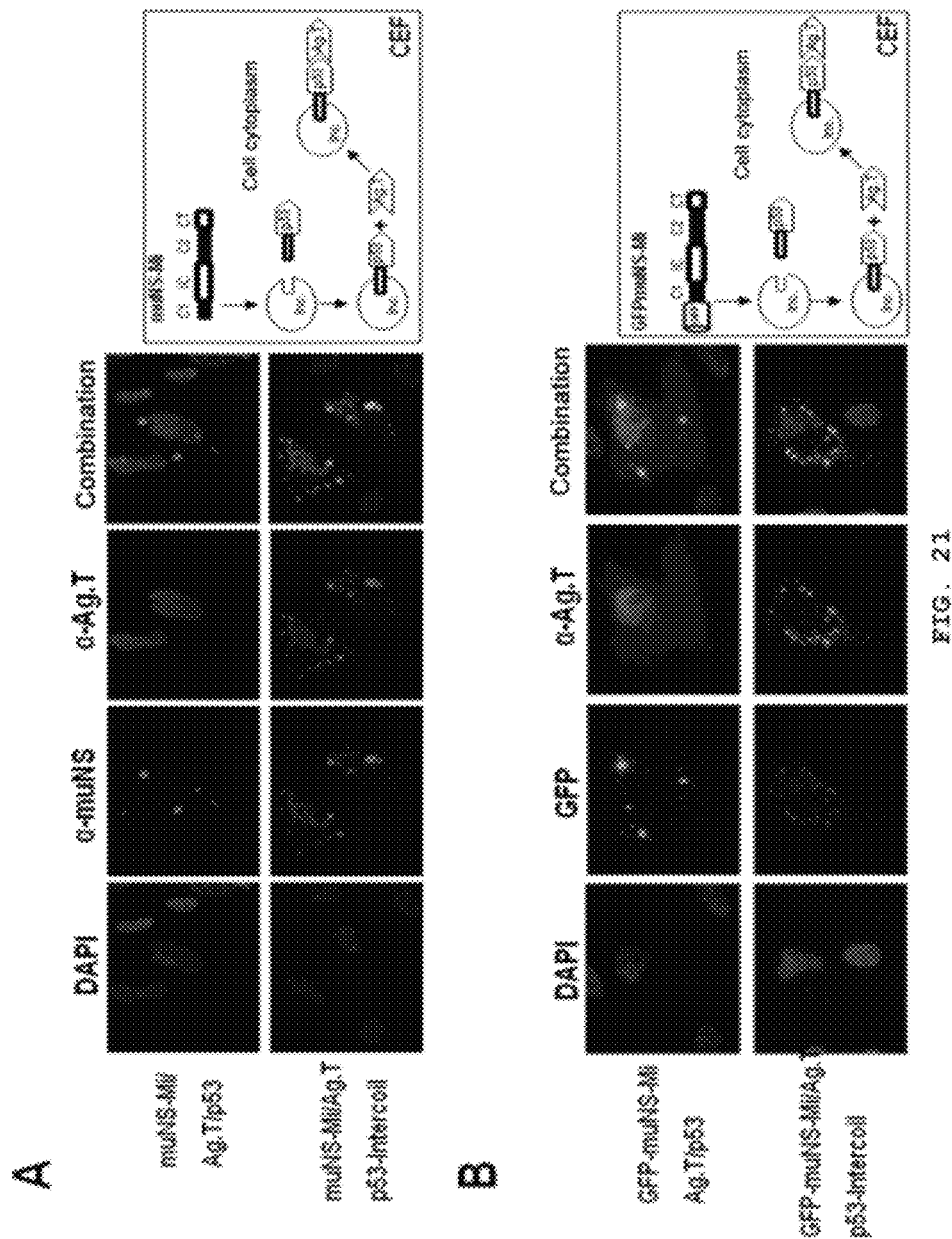
FIG. 21 shows the intracellular distribution of the SV40 T-antigen in the presence of muNS-Mi or GFP-muNS-Mi co-expressed with p53 or p53-Intercoil in CEF cells. (A) Subcellular localization of the T-antigen in cells co-expressing muNS-Mi and p53 or muNS-Mi and p53-Intercoil. B-Subcellular localization of the T-antigen in cells co-expressing GFP-muNS-Mi and p53 or GFP-muNS-Mi and p53-Intercoil. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and polyclonal anti-muNS antibodies followed by an Alexa 488-conjugated secondary antibody, where appropriate. The nuclei were stained with DAPI. A diagram of what is shown in the immunofluorescence images is depicted on the right of the panels according to the standards of the diagram of FIG. 13.

(E) Binding Exogenous SV40 T-Antigen to p53-Intercoil Bound to the Inclusions Formed by muNS-Mi Just as it was done with muNS, the interaction between p53 and the exogenous T-antigen expressed from plasmids using muNS-Mi as a platform was studied. To that end, CEF cells were transfected with each of the constructs and their distribution was analyzed by means of immunofluorescence as done previously. Again, p53 was localized exclusively in the nucleus of the cells which co-expressed muNS-Mi or GFP-muNS-Mi and not in the inclusions, even being excluded therefrom (FIGS. 20A and B top panels). However, upon replacing p53 with p53-Intercoil, the latter was mainly detected in the inclusions (FIGS. 20A and B bottom panels). Such as the case of Cos-7 cells, the presence of nuclear and cytoplasmic inclusions was observed. Furthermore, the T-antigen was localized exclusively in the nucleus of the cells where it was co-expressed with p53 and muNS-Mi or GFP-muNS-Mi (FIGS. 20A and B, top panels). However, by replacing p53 with p53-Intercoil, the T-antigen was mainly localized in the cytoplasmic and nuclear inclusion bodies (FIGS. 20A and B, bottom panels).

Example 8

Nuclear muNS Inclusions

The appearance of small inclusions in the nucleus upon using the system with muNS-Mi and two nuclear proteins (p53 and Ag. T) suggested that the sequestration system and detection system for detecting interactions between proteins could be adapted to cell nucleus and the method could thus be used for nuclear proteins. The first objective was to attempt obtaining inclusions formed by the muNS protein in the nucleus. To that end, two different strategies were followed: i) short nuclear localization sequences (NLS) (T-antigen NLS (PKKKRKV) (Kalderon et al., mentioned ad supra) and the Avian reovirus p17 protein NLS (IAAKRGRQLD) (Costas-Iglesias et al., 2005, J. Virol. 79: 2141-50)) were fused to muNS and ii) a fusion was generated between muNS and the activation domain used in the two-hybrid system for mammalian cells (Mammalian Matchmaker, Clontech) containing the Ag.T NLS fused to the Herpes virus VP16 protein, if the short NLSs were not correctly arranged around the protein to allow the capture thereof by cell transporters. The identity of each construct was confirmed by means of sequencing and Western-blot. For determining the intracellular distribution of each of the constructs, CEF cells were transfected with each of the plasmids expressing them, and they were fixed at 24 h.p.t and subjected to immunofluorescence with polyclonal anti-muNS antibodies.

The results obtained were the following: i) the VP16-muNS fusion protein resulted in the formation of nuclear inclusions in most of the cells (FIG. 22A, top panels); ii) the muNS with the T-antigen NLS (NLS-Ag.T-muNS) at its amino end resulted in nuclear inclusions in most of the cells, even though in some cells some inclusions were also detected in the cytoplasm (FIG. 22A, bottom panels); iii) the inclusion of the p17 NLS did not produce nuclear inclusions (data not shown). In view of these results, developing the system with the VP16-muNS and NLS-AgT-muNS constructs was attempted.

Directing muNS-Mi to the nucleus to form therein inclusion bodies was also attempted. However, in contrast to muNS, the VP16-muNS-Mi construct did not result in nuclear inclusions, but was distributed in a diffused manner throughout the nucleus (results not shown). Furthermore, neither did the introduction of different NLS (T-antigen NLS and avian reovirus p17 NLS) at the amino end of muNS-Mi produced nuclear inclusion bodies (data not shown). These negative results may be due to the fact that the proximity of the added NLS (strong basic character) and the first coiled-coil (highly hydrophobic) affects the correct muNS-Mi folding.

Figure 22:
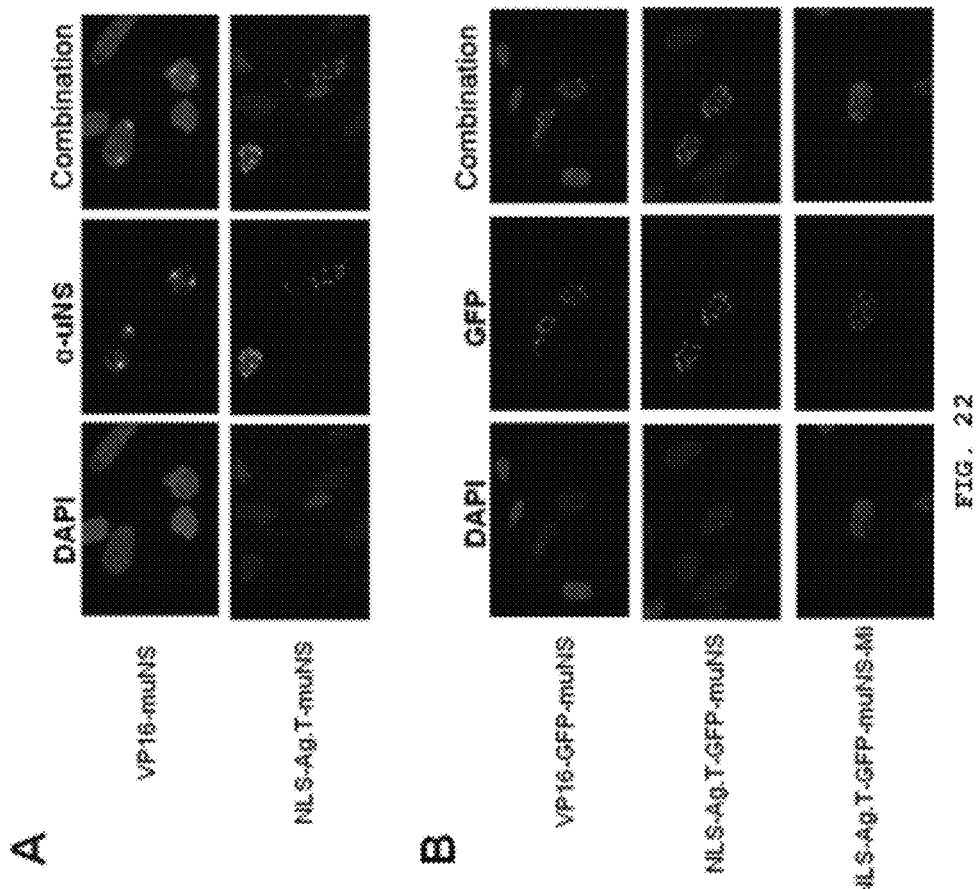
FIG. 22 describes the subcellular localization of the inclusions formed by different chimaeras of muNS and muNS-Mi. (A) Intracellular distribution of VP16-muNS and NLS-Ag.T-muNS. (B) Intracellular distribution of VP16-GFP-muNS, NLS-Ag.T-GFP-muNS and NLS-Ag.T-GFP-muNS-Mi. In (A) and (B), the semi-confluent CEF cells were transfected with the plasmids expressing the proteins indicated on the left of the figure. The cells were fixed at 24 h.p.t. and were then subjected to indirect immunofluorescence with polyclonal anti-muNS antibodies followed by an Alexa 488-conjugated secondary antibody or to direct detection in the case of (B). The nuclei were stained with DAPI.

As mentioned above, the fusion of GFP to the amino end of muNS and muNS-Mi did not affect its inclusion-forming capacity, and had the advantage that antibodies are not required for detecting its intracellular distribution. By taking this into account, a decision was made to generate nuclear fluorescent inclusions following the following strategies: i) fusing VP16 to GFP-muNS and GFP-muNS-Mi; and ii) introducing T-antigen NLS at the amino end of the chimeras GFP-muNS and GFP-muNS-Mi. The different fusion proteins, i.e., VP16-GFP-muNS, NLS-Ag.T-GFP-muNS and NLS-Ag.T-GFP-muNS-Mi produced nuclear inclusion bodies in most of the cells (FIG. 22B, bottom panels). In the case of VP16-GFP-muNS-Mi no nuclear inclusions were produced (data not shown).

Incorporation of GFP-Intercoil into Nuclear Inclusions

Figure 23:
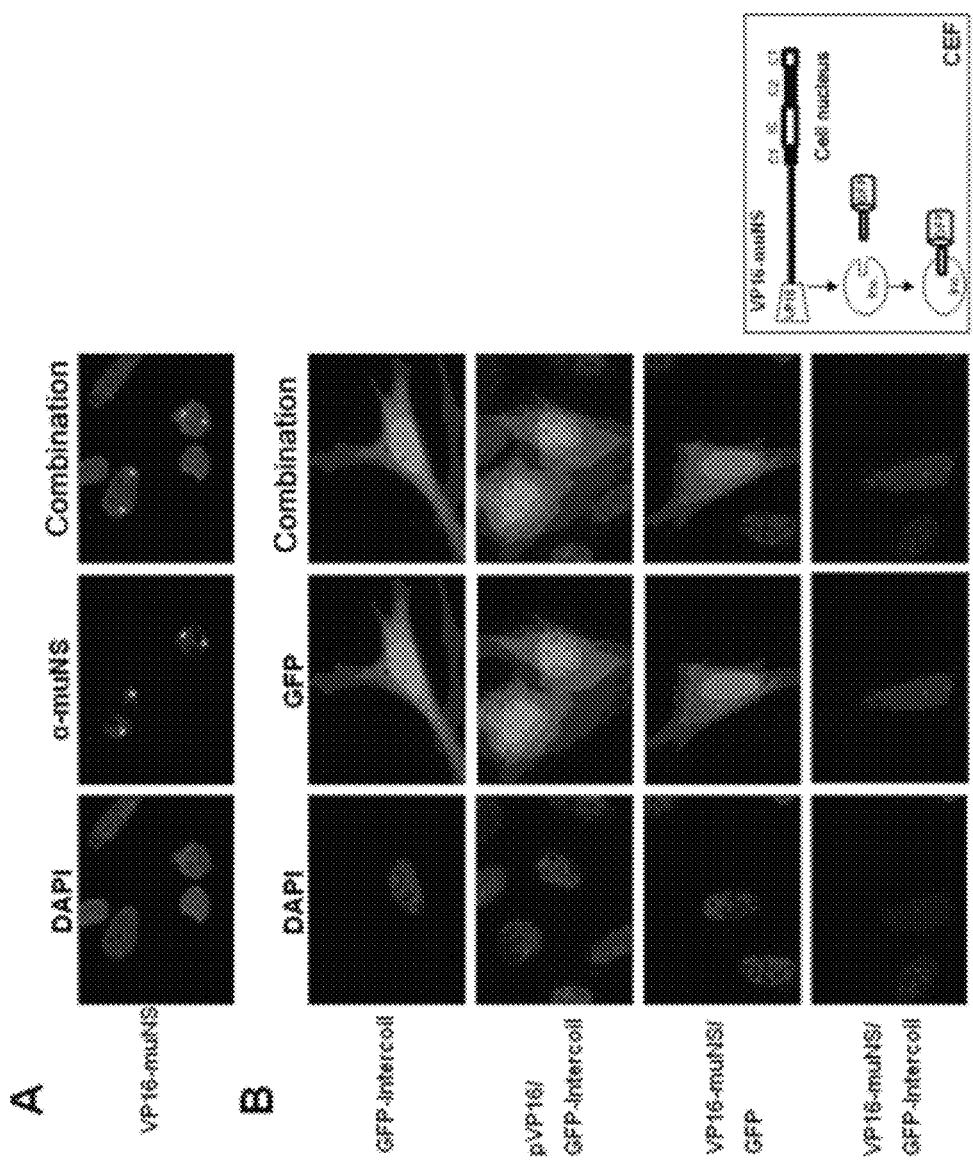
FIG. 23 shows the intracellular distribution of GFP-Intercoil in the presence of the nuclear inclusions formed by VP16-muNS. (A) Subcellular localization of VP16-muNS. (B) Subcellular localization of GFP and GFP-Intercoil in the presence of the nuclear inclusions formed by VP16-muNS. In (A) and (B), the semi-confluent CEF cells were transfected with the plasmid expressing the protein indicated on the left of the figure. The cells were fixed at 24 h.p.t. and were then subjected to indirect immunofluorescence with polyclonal anti-muNS antibodies followed by an Alexa 488-conjugated secondary antibody or to direct fluorescence detection in the case of (B). The nuclei were stained with DAPI. A diagram of what is shown in the immunofluorescence images is depicted on the right of the panels according to the standards of the diagram of FIG. 13.
Figure 24:
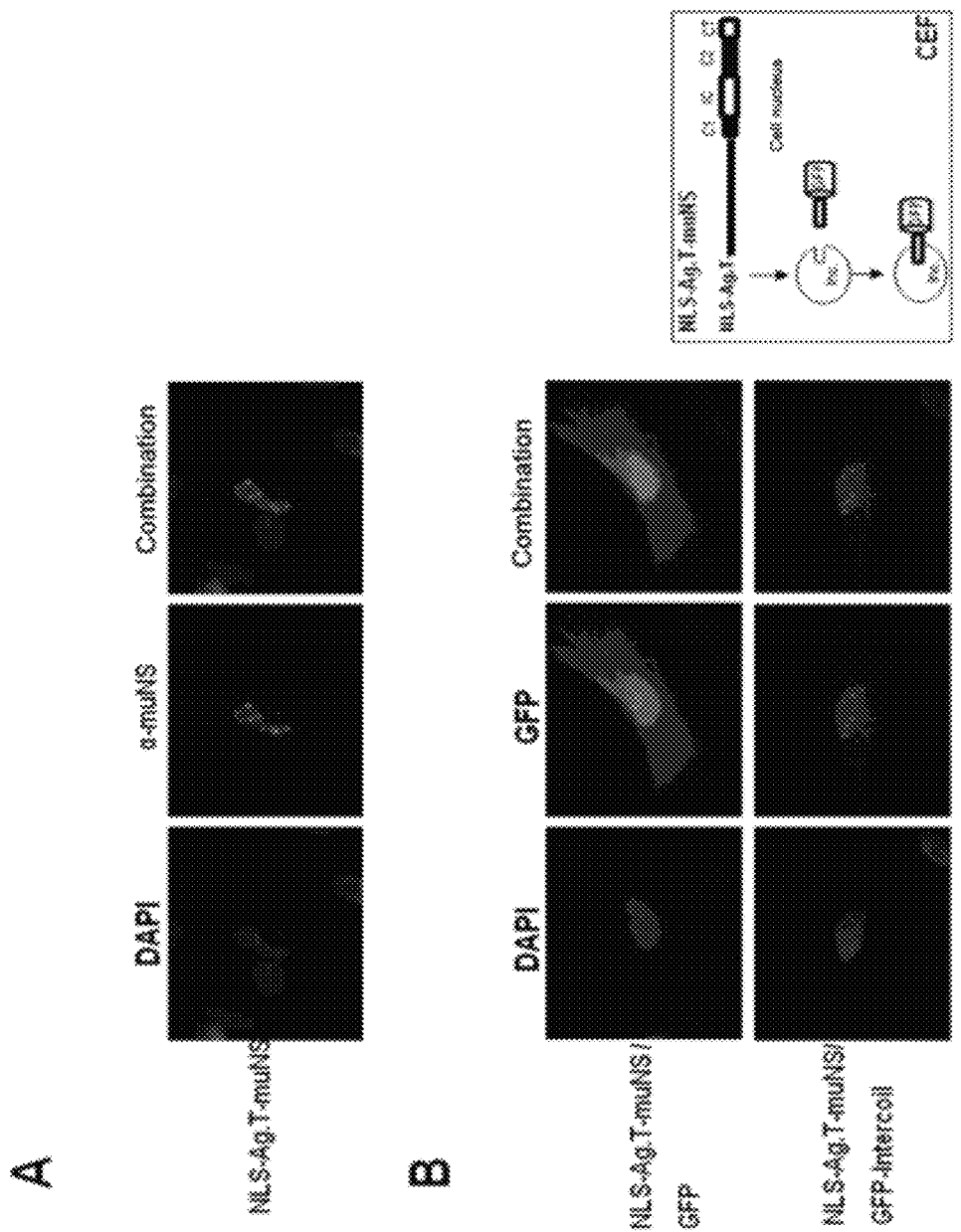
FIG. 24 shows the intracellular distribution of GFP-Intercoil in the presence of the nuclear inclusions formed by NLS-Ag.T-muNS. (A) Subcellular localization of NLS-Ag.T-muNS. (B) Subcellular localization of GFP and GFP-Intercoil in the presence of the nuclear inclusions formed by NLS-Ag.T-muNS. In (A) and (B), the semi-confluent CEF cells were transfected with the plasmid expressing the protein indicated on the left of the figure. The cells were fixed at 24 h.p.t. and were then subjected to indirect immunofluorescence with polyclonal anti-muNS antibodies followed by an Alexa 488-conjugated secondary antibody or were directly viewed in the case of (B). The nuclei were stained with DAPI. A diagram of what is shown in the immunofluorescence images is depicted on the right of the panels according to the standards of the diagram of FIG. 13.

The following step was to check whether the nuclear inclusions obtained were capable of recruiting GFP-Intercoil without affecting the integrity thereof. To that end, CEF cells were co-transfected with each of the nuclear inclusion-forming constructs together with GFP-Intercoil or untagged GFPs which were used as controls. The cells were fixed at 24 h.p.t and viewed with a fluorescence microscope for detecting their intracellular distribution. The GFP protein was distributed in a diffused manner throughout the cell upon being expressed together with any of the nuclear inclusion-forming chimeras (FIGS. 23B, third line and 22B, top panels). However, GFP-Intercoil was almost exclusively localized in the inclusions formed both by VP16-muNS (FIG. 23B, bottom panels), and by NLS-Ag.T-muNS (FIG. 24B, bottom panels). These results show that the nuclear inclusions described in this specification are capable of capturing proteins tagged with the Intercoil domain without altering the integrity of the inclusions or the activity of the protein incorporated.

Example 9

Binding Endogenous and Exogenous SV40 T-Antigen to p53-Intercoil Bound to Nuclear Inclusions The objective was to show that this system can be used for detecting the interaction between proteins in cell nucleus. Like in the preceding cases, the system was analyzed with the example p53-Ag.T, both in Cos-7 cells (where the Ag.T is expressed endogenously) and in CEF cells (where the Ag.T is expressed endogenously).

(A) Endogenous Ag.T, COS7 Cells

Figure 25:
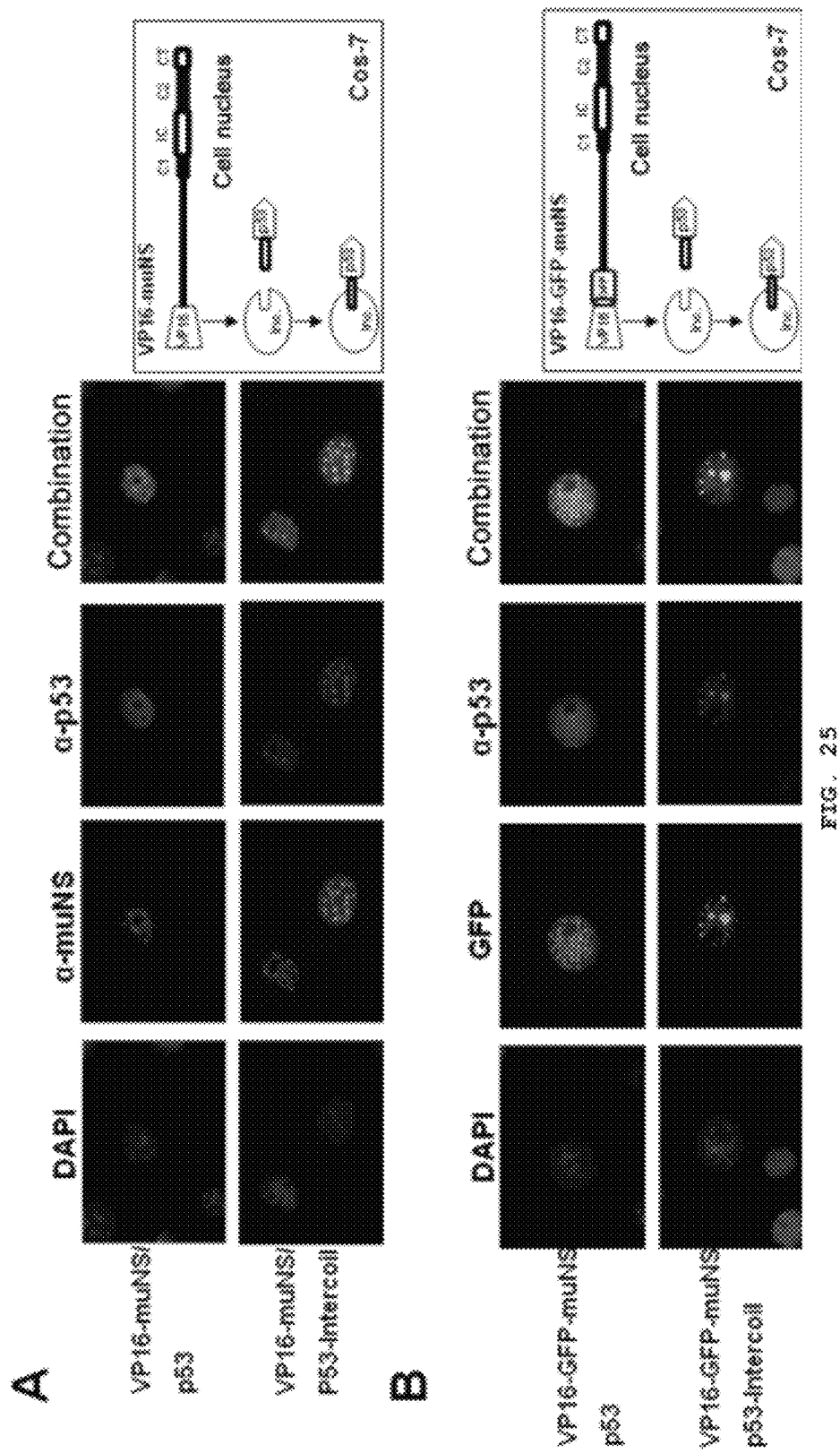
FIG. 25 shows the intracellular distribution of p53 or p53-Intercoil in the presence of the nuclear inclusions formed by VP-16-muNS or VP16-GFP-muNS in Cos-7 cells. (A) Subcellular localization of p53 or p53-Intercoil in the presence of inclusions formed by VP16-muNS. (B) Subcellular localization of p53 or p53-Intercoil in the presence of inclusions formed by VP16-GFP-muNS. In (A) and (B), the Cos-7 cells were co-transfected with the plasmids expressing the proteins indicated on the left of the figure, they were fixed at 24 h.p.t. and were then subjected to indirect immunofluorescence with monoclonal anti-p53 antibody followed by an Alexa 592-conjugated secondary antibody and in the case of (A), polyclonal anti-muNS antibodies followed by an Alexa 488-conjugated secondary antibody. The VP16-GFP-muNS was viewed directly. The nuclei were stained with DAPI. A diagram of what is shown in the immunofluorescence images is depicted on the right of the panels according to the standards of the diagram of FIG. 13.

In the case of Cos-7 cells, it was observed that p53 was distributed in a diffused manner in the nucleus without co-localizing with the nuclear inclusions in the cells expressing any of the different constructs with capacity to form said inclusions (VP16-muNS, VP16-GFP-muNS, NLS-Ag.T-muNS, NLS-Ag.T-GFP-muNS or NLS-Ag.T-GFP-muNS-Mi) (FIGS. 25A and B; FIGS. 29A and B and FIG. 31A, top panels); showing that: i) p53 does not associate with the nuclear inclusions; and ii) anti-p53 antibody does not recognize the nuclear inclusions. However, upon using p53-Intercoil, it was almost exclusively localized in the inclusions in most of the cells (FIGS. 25A and B; FIGS. 29A and B and FIG. 31A, bottom panels) therefore the incorporation of p53-Intercoil did not affect the integrity of the inclusions.

Figure 26:
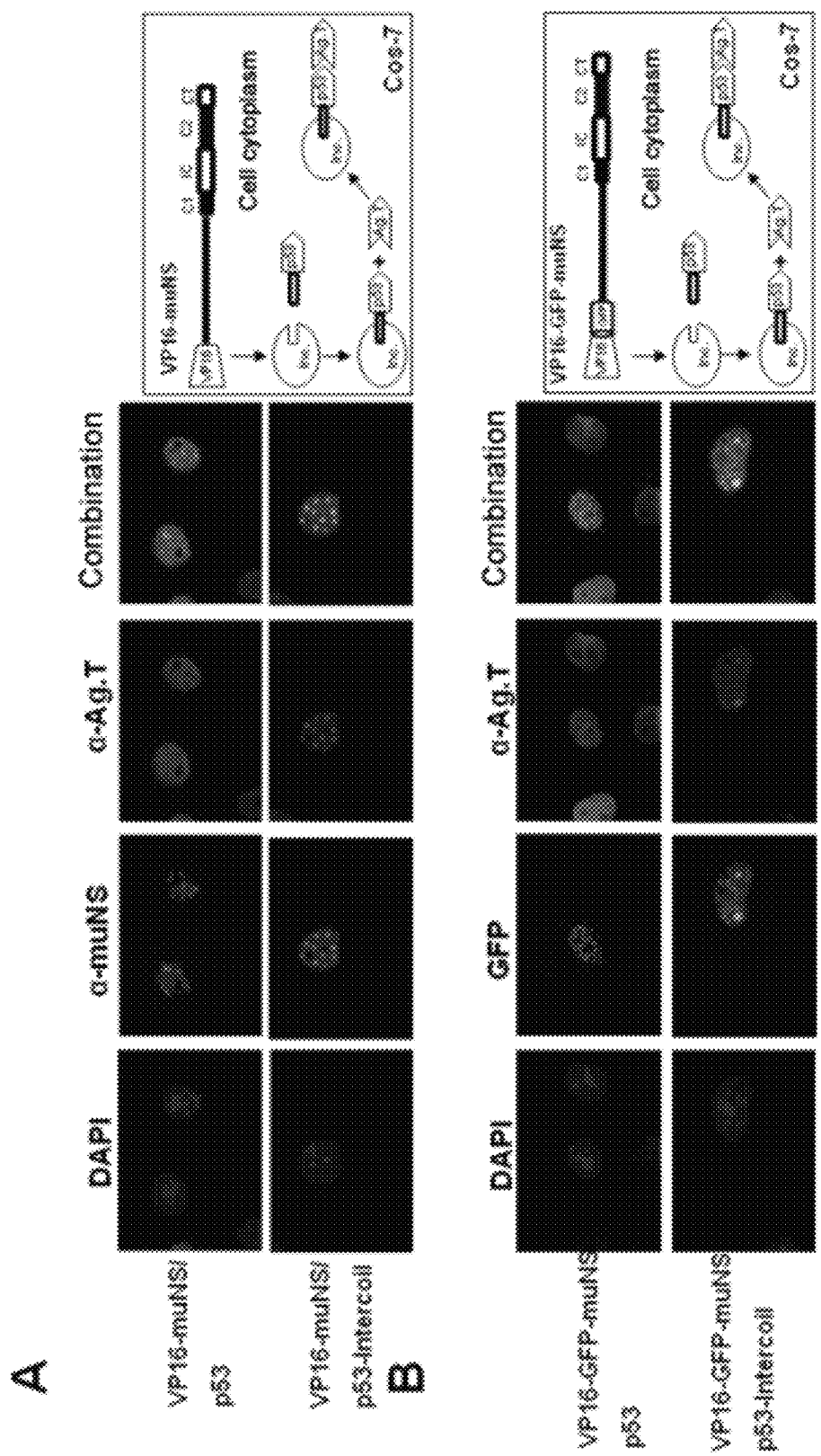
FIG. 26 shows the intracellular distribution of the SV40 T-antigen in the presence of VP16-muNS or VP16-GFP-muNS co-expressed with p53 or p53-Intercoil in Cos-7 cells. (A) Subcellular localization of the T-antigen in cells co-expressing VP16-muNS and p53 or VP16-muNS and p53-Intercoil. (B) Subcellular localization of the T-antigen in cells co-expressing VP16-GFP-muNS and p53 or VP16-GFP-muNS and p53-Intercoil. In (A) and (B), the semi-confluent Cos-7 cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and in the case of (A), polyclonal anti-muNS antibodies followed by an Alexa 488-conjugated secondary antibody. The nuclei were stained with DAPI. The VP16-GFP-muNS was viewed directly. The nuclei were stained with DAPI. A diagram of what is shown in the immunofluorescence images is depicted on the right of the panels according to the standards of the diagram of FIG. 13.
Figure 27:
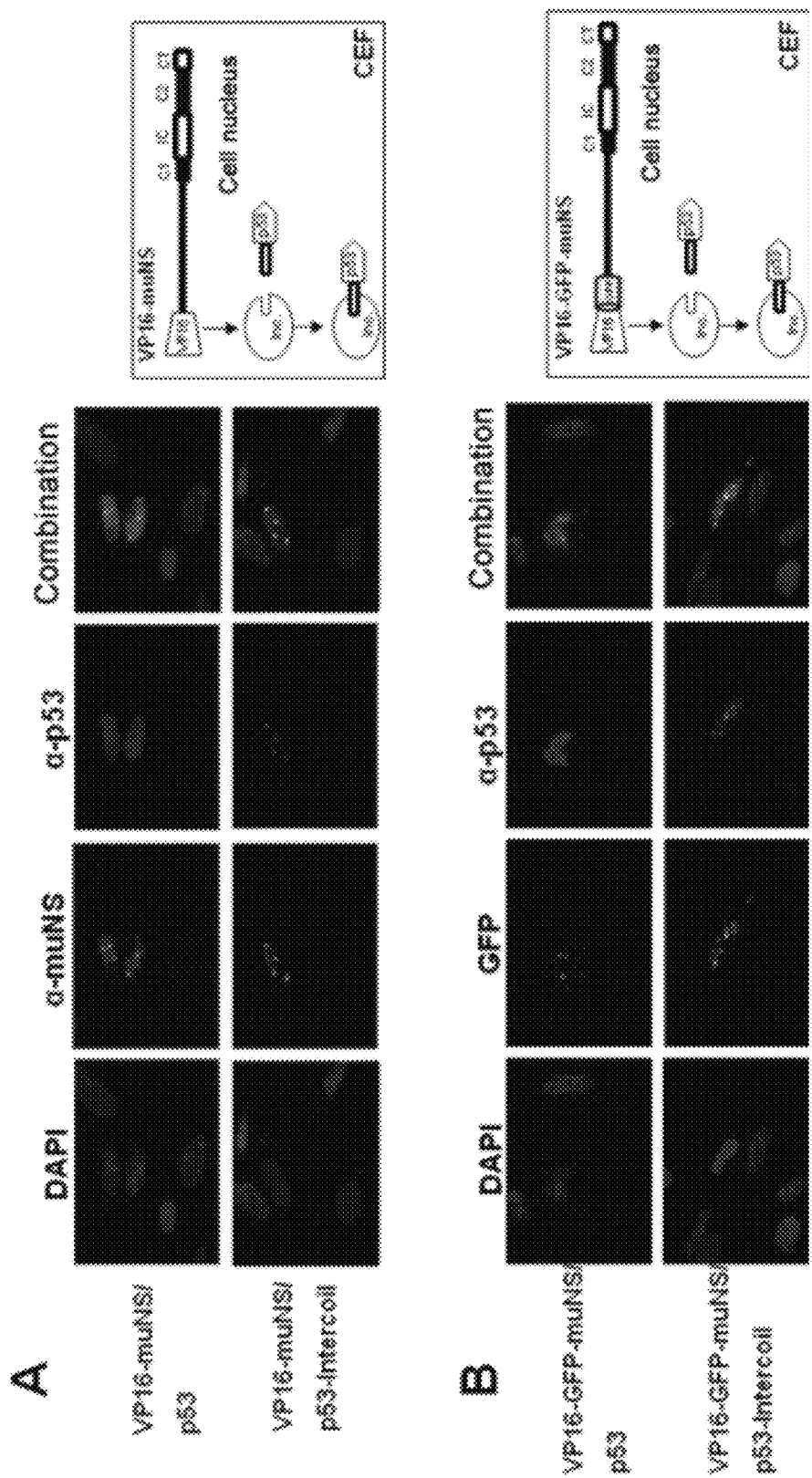
FIG. 27 shows the intracellular distribution of p53 or p53-Intercoil in the presence of the nuclear inclusions formed by VP16-muNS or VP16-GFP-muNS in CEF cells. (A) Subcellular localization of p53 or p53-Intercoil in the presence of inclusions formed by VP16-muNS. (B) Subcellular localization of p53 or p53-Intercoil in the presence of inclusions formed by VP16-GFP-muNS. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and in the case of (A), polyclonal anti-muNS antibodies followed by an Alexa 488-conjugated secondary antibody. The VP16-GFP-muNS was viewed directly and the nuclei were stained with DAPI. A diagram of what is shown in the immunofluorescence images is depicted on the right of the panels according to the standards of the diagram of FIG. 13.
Figure 28:
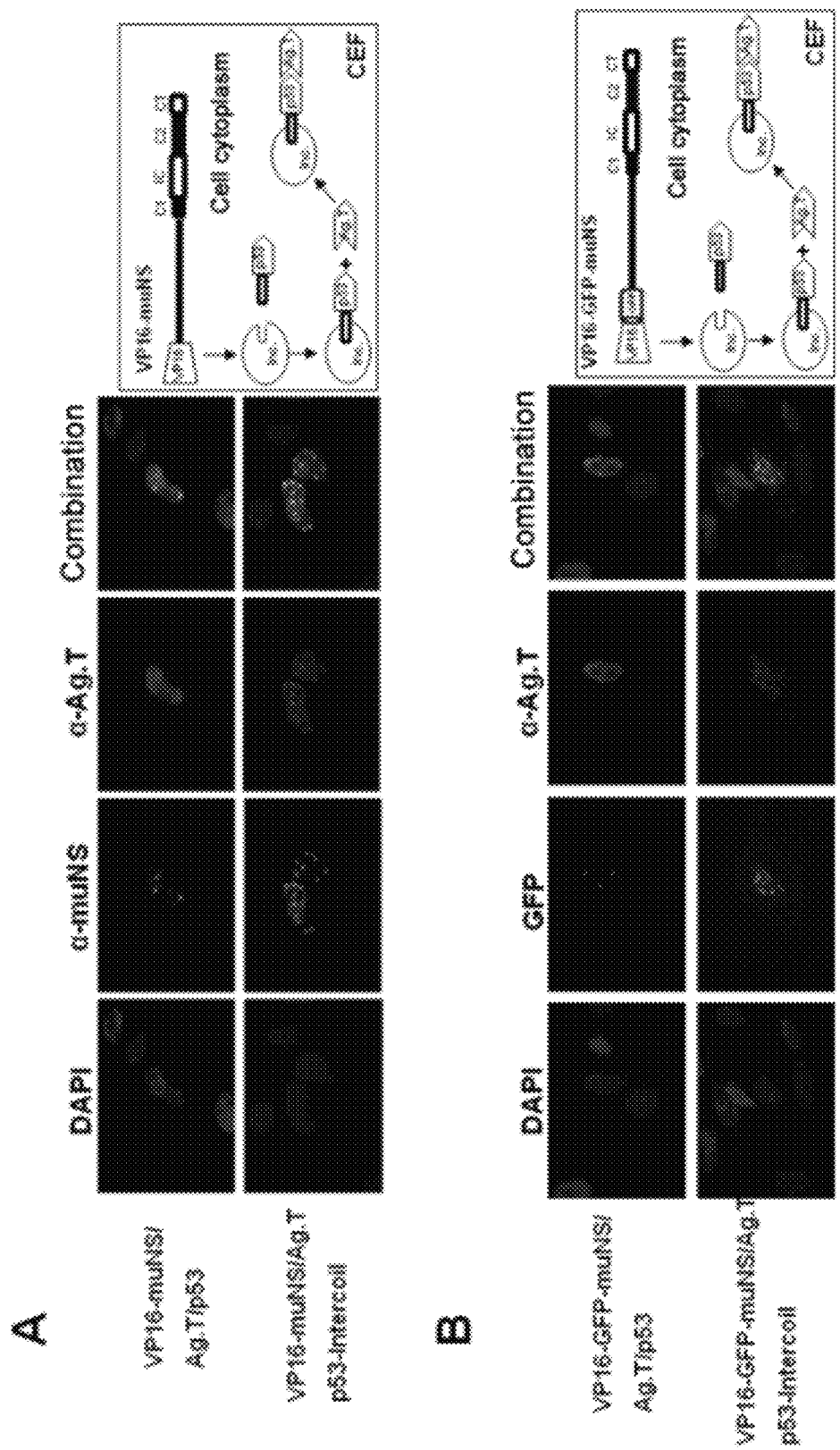
FIG. 28 shows the intracellular distribution of the SV40 T-antigen in the presence of VP16-muNS or VP16-GFP-muNS co-expressed with p53 or p53-Intercoil in CEF cells. (A) Subcellular localization of the T-antigen in cells co-expressing VP16-muNS and p53 or VP16-muNS and p53-Intercoil. (B) Subcellular localization of the T-antigen in cells co-expressing VP16-GFP-muNS and p53 or VP16-GFP-muNS and p53-Intercoil. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and in (A), polyclonal anti-muNS antibodies followed by an Alexa 488-conjugated secondary antibody. The VP16-GFP-muNS was viewed directly. The nuclei were stained with DAPI. A diagram of what is shown in the immunofluorescence images is depicted on the right of the panels according to the standards of the diagram of FIG. 13.
Figure 30:
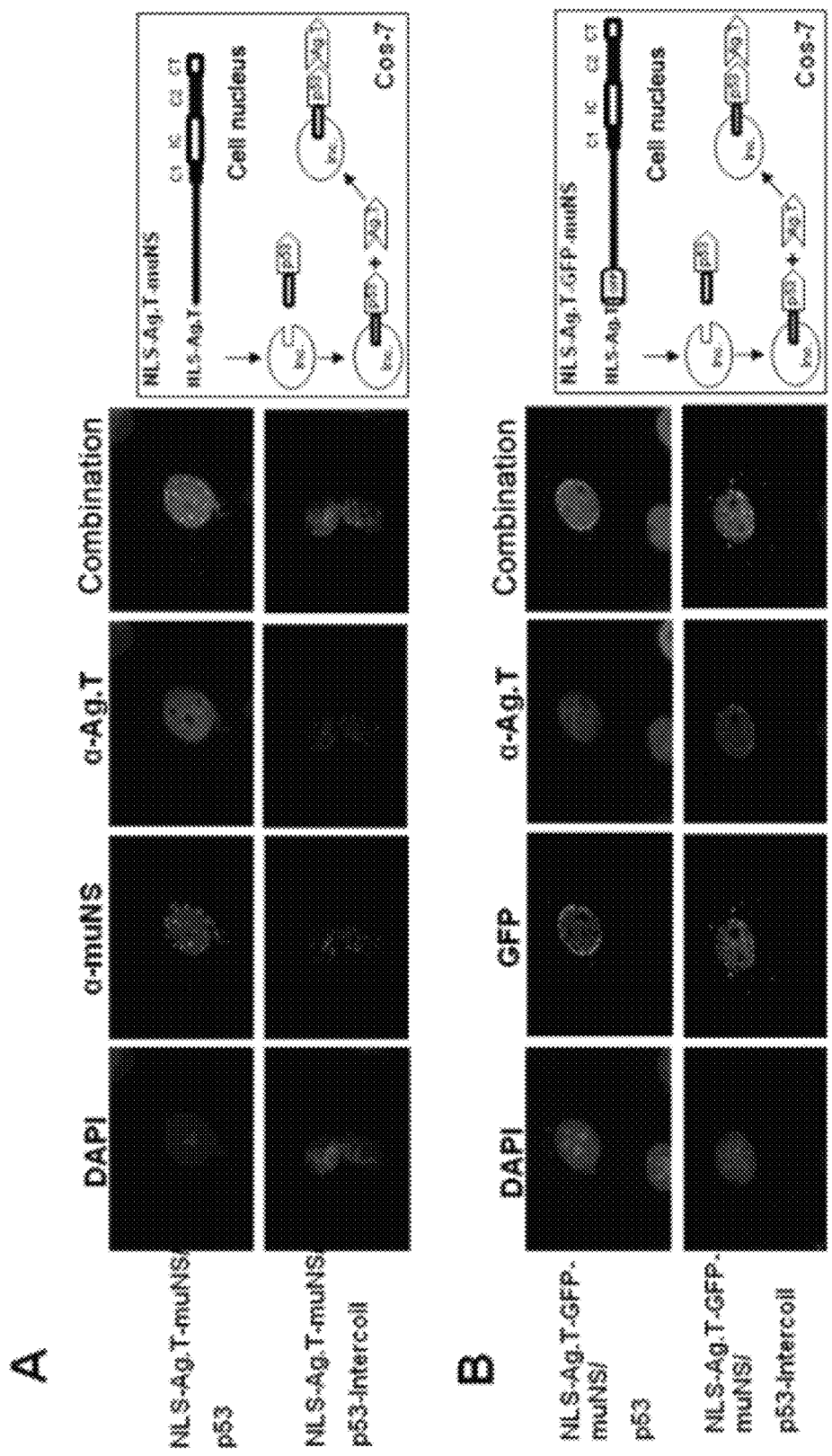
FIG. 30 shows the intracellular distribution of the SV40 T-antigen in the presence of NLS-Ag.T-muNS or NLS-Ag.T-GFP-muNS co-expressed with p53 or p53-Intercoil in Cos-7 cells. (A) Subcellular localization of the T-antigen in cells co-expressing NLS-Ag.T-muNS and p53 or NLS-Ag.T-muNS and p53-Intercoil. (B) Subcellular localization of the T-antigen in cells co-expressing NLS-Ag.T-GFP-muNS and p53 or NLS-Ag.T-GFP-muNS and p53-Intercoil. In (A) and (B), the semi-confluent Cos-7 cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and in (A), polyclonal anti-muNS antibodies followed by an Alexa 488-conjugated secondary antibody. The nuclei were stained with DAPI. The NLS-Ag.T-GFP-muNS was viewed directly. A diagram of what is shown in the immunofluorescence images is depicted on the right of the panels according to the standards of the diagram of FIG. 13.
Figure 32:
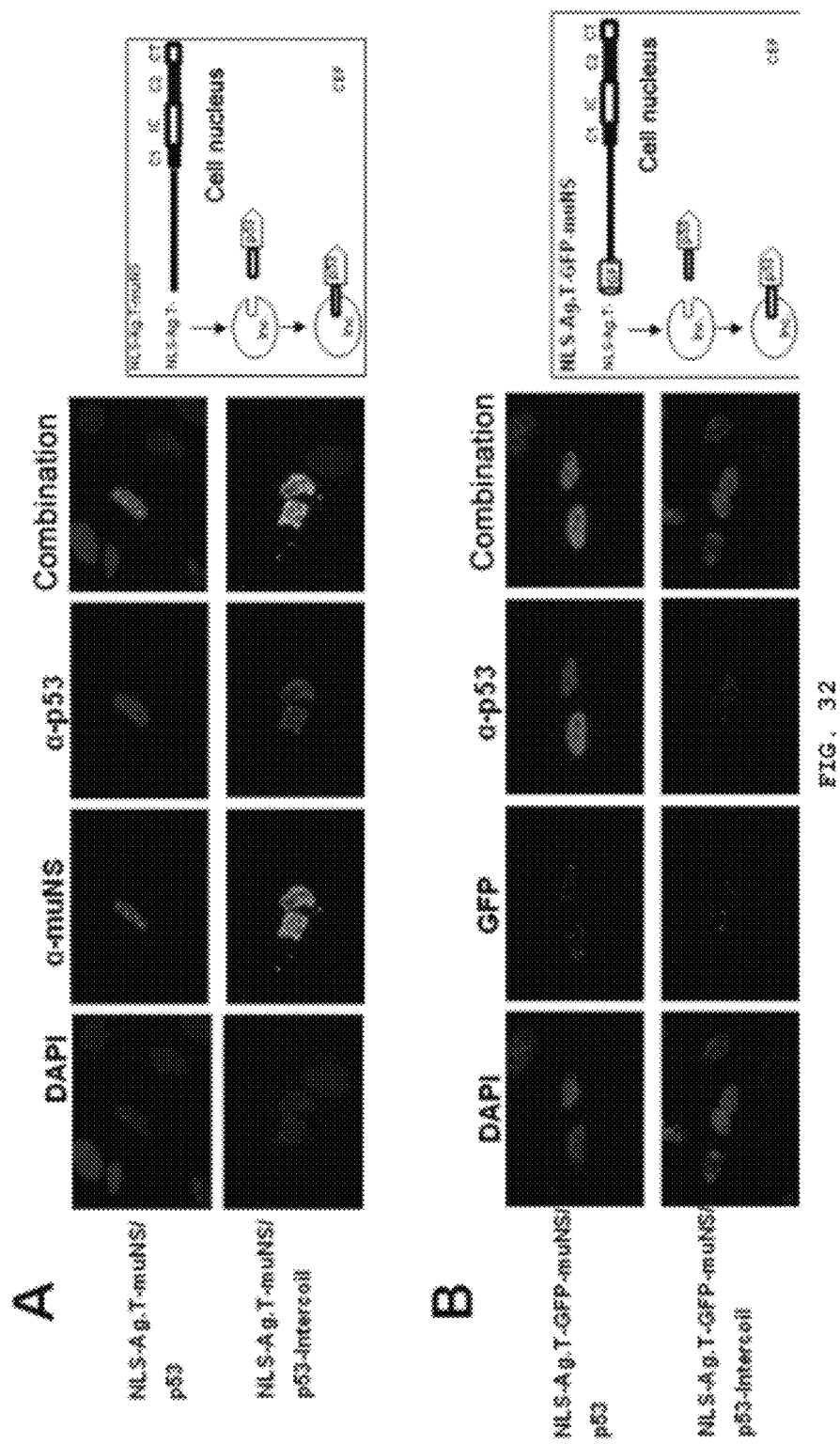
FIG. 32 shows the intracellular distribution of p53 or p53-Intercoil in the presence of the nuclear inclusions formed by NLS-Ag.T-muNS or NLS-Ag.T-GFP-muNS in CEF cells. (A) Subcellular localization of p53 or p53-Intercoil in the presence of inclusions formed by NLS-Ag.T-muNS. (B) Subcellular localization of p53 or p53-Intercoil in the presence of inclusions formed by NLS-Ag.T-GFP-muNS. In (A) and (B), the semi-confluent CEF cells were co-transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, and in (A), polyclonal anti-muNS antibodies followed by an Alexa 488-conjugated secondary antibody. The NLS-Ag.T-GFP-muNS was viewed directly. The nuclei were stained with DAPI. A diagram of what is shown in the immunofluorescence images is depicted on the right of the panels according to the standards of the diagram of FIG. 13.
Figure 33:
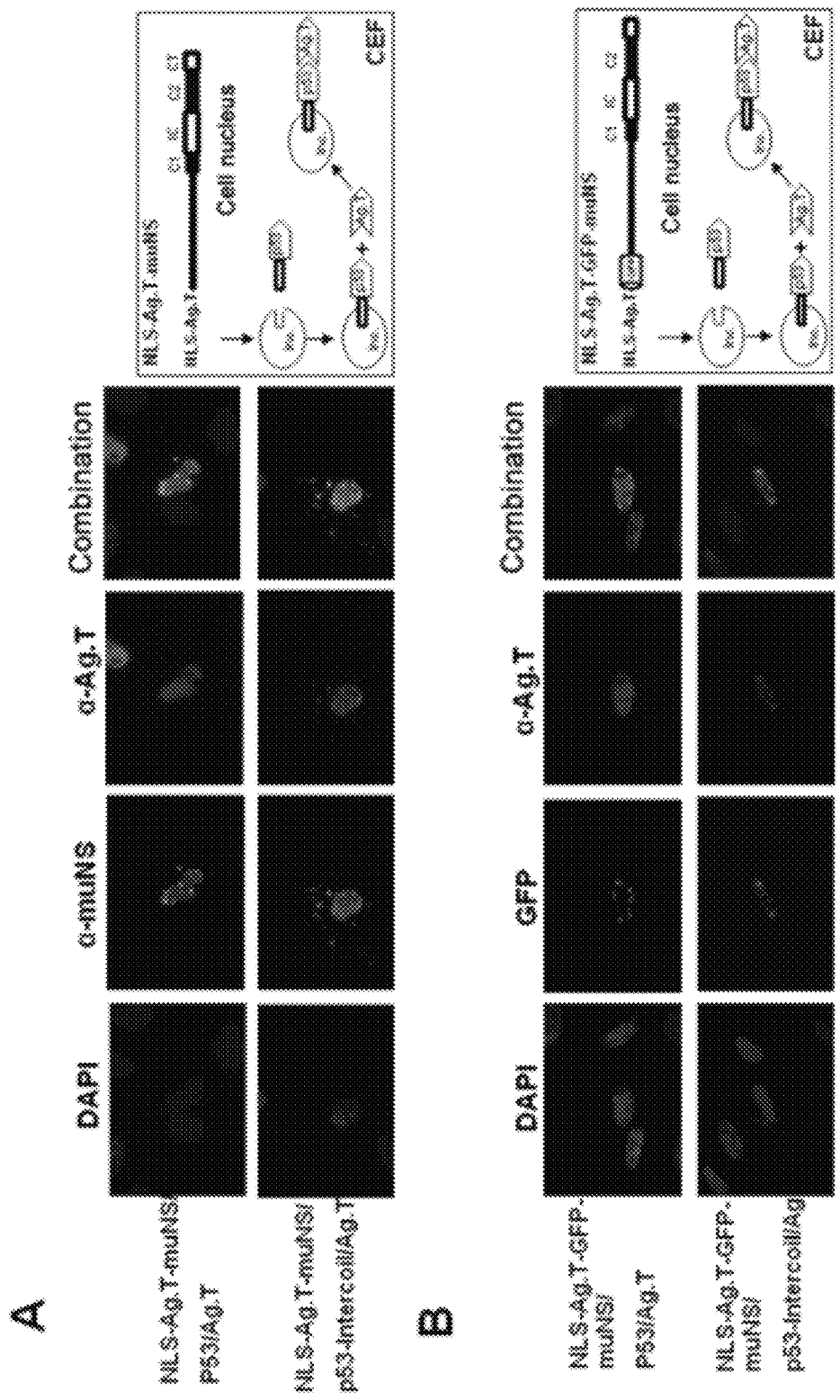
FIG. 33 shows the intracellular distribution of the SV40 T-antigen in the presence of NLS-Ag.T-muNS or NLS-Ag.T-GFP-muNS co-expressed with p53 or p53-Intercoil in CEF cells. (A) Subcellular localization of the T-antigen in cells co-expressing NLS-Ag.T-muNS and p53 or NLS-Ag.T-muNS and p53-Intercoil. (B) Subcellular localization of the T-antigen in cells co-expressing NLS-Ag.T-GFP-muNS and p53 or NLS-Ag.T-GFP-muNS and p53-Intercoil. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-T-antigen antibody followed by an Alexa 592-conjugated secondary antibody, and in (A), polyclonal anti-muNS antibodies followed by an Alexa 488-conjugated secondary antibody. The NLS-Ag.T-GFP-muNS was viewed directly. The nuclei were stained with DAPI. A diagram of what is shown in the immunofluorescence images is depicted on the right of the panels according to the standards of the diagram of FIG. 13.
Figure 34:
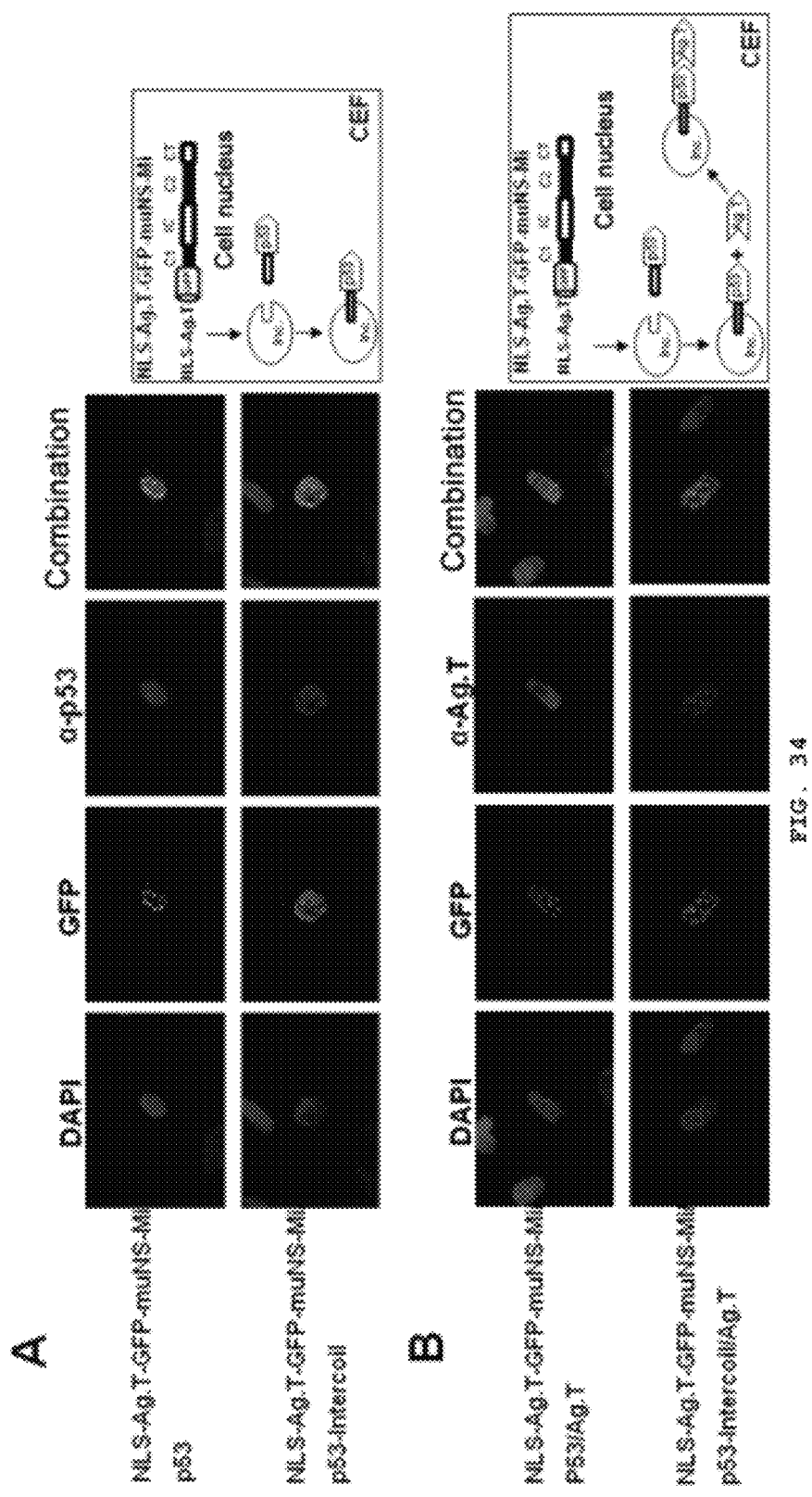
FIG. 34 describes the intracellular distribution of the SV40 T-antigen in the presence of NLS-Ag.T-GFP-muNS-Mi co-expressed with p53 or p53-Intercoil in CEF cells. (A) Subcellular localization of p53 or p53-Intercoil in the presence of inclusions formed by NLS-Ag.T-GFP-muNS-Mi. (B) Subcellular localization of the T-antigen in cells co-expressing NLS-Ag.T-GFP-muNS-Mi and p53 or NLS-Ag.T-GFP-muNS-Mi and p53-Intercoil. In (A) and (B), the semi-confluent CEF cells were transfected with the plasmids expressing the proteins indicated on the left of the figure. The cells were fixed at 24 h.p.t. and were then subjected to indirect immunofluorescence with a monoclonal anti-p53 antibody in (A) or T-antigen in (B) followed by an Alexa 592-conjugated secondary antibody. The NLS-Ag.T-GFP-muNS-Mi was viewed directly. The nuclei were stained with DAPI. A diagram of what is shown in the immunofluorescence images is depicted on the right of the panels according to the standards of the diagram of FIG. 13.

The interaction between p53 and T-antigen was analyzed by detecting the T-antigen instead of p53 in a similar experiment. It was thus found that, in the cells which expressed p53 and the different versions with capacity to form nuclear inclusions (VP16-muNS or VP16-GFP-muNS or NLS-Ag.T-muNS or NLS-Ag.T-GFP-muNS or NLS-Ag.T-GFP-muNS-Mi), the T-antigen was localized exclusively in the nucleus without coinciding with the inclusion bodies (FIGS. 26A and B; FIGS. 30A and B and FIG. 31B, top panels); showing that: i) T-antigen does not associate with the nuclear inclusion bodies; and ii) the specific anti-T-antigen antibody does not recognize the nuclear inclusions. In contrast, upon replacing p53 with p53-Intercoil, the T-antigen was mainly localized in the inclusions (FIGS. 26A and B; FIGS. 30A and B and FIG. 31B, bottom panels). These results show that: i) the incorporation of T-antigen into the nuclear inclusion bodies by association with p53 does not affect the integrity thereof; and ii) the systems described herein can be used as platforms to see whether two proteins interact with one another in the nucleus of eukaryotic cells.

(B) Exogenous Ag.T, CEF Cells

By studying the interaction between p53 and T-antigen in CEF cells expressing the T-antigen by transfecting the cells with expression plasmids, data similar to that in the case of endogenous T-antigen which can be seen in FIGS. 27, 28, 32, 33 and 34, was obtained.

Example 10 muNS-Mi and muNS Protein Efficiently Recruit p53-Intercoil and GFP-Intercoil

Figure 35:
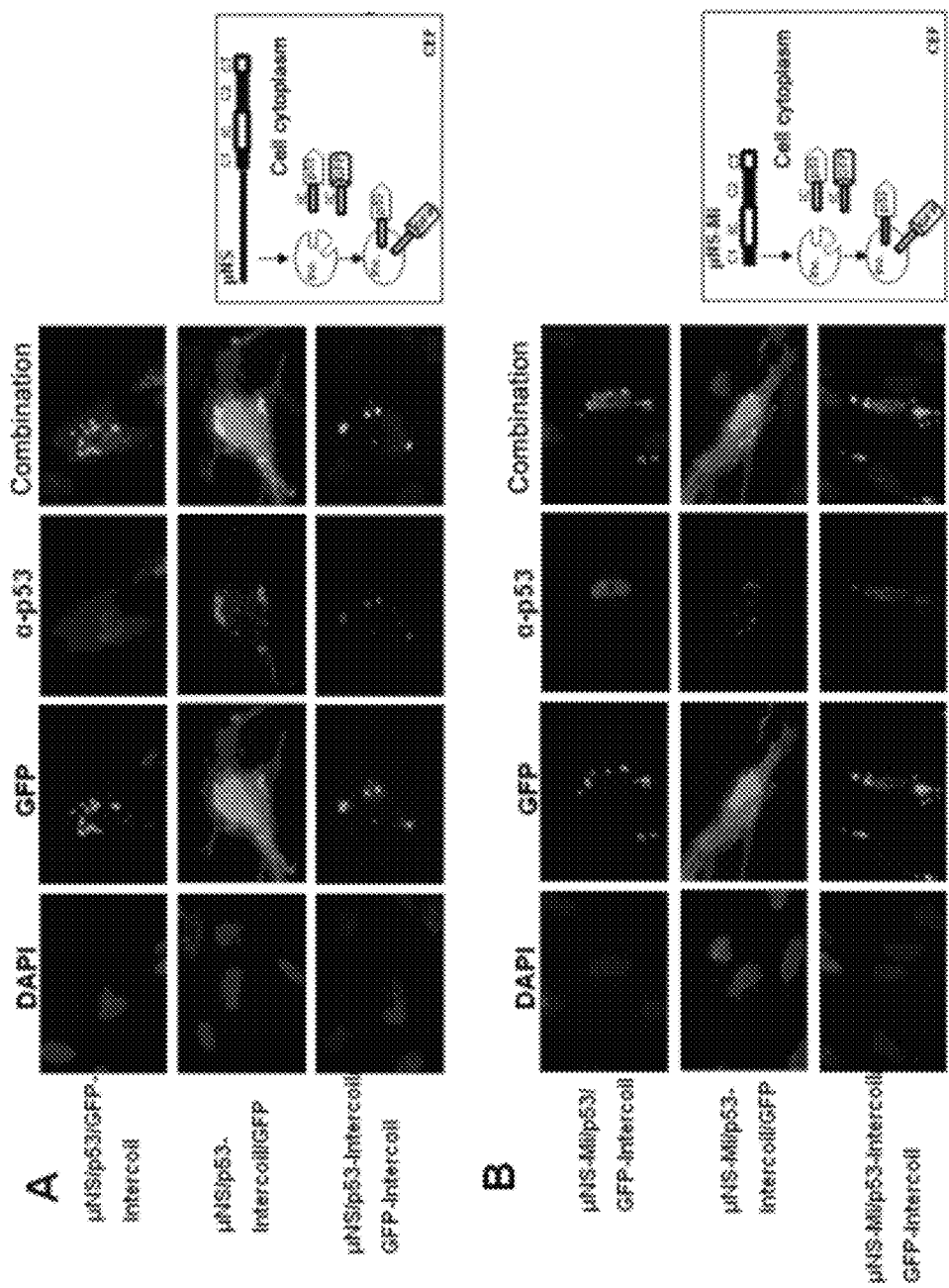
FIG. 35 shows the intracellular distribution of p53-Intercoil and GFP-Intercoil in the presence of the inclusions formed by muNS or muNS-Mi. (A) Subcellular localization of p53-Intercoil and GFP-Intercoil in the presence of the inclusions formed by muNS. Semi-confluent CEF cells were transfected with the plasmids expressing the proteins indicated on the left of the figure. The cells were fixed at 24 h.p.t. and were then subjected to indirect immunofluorescence with a monoclonal anti-p53 antibody followed by an Alexa 592-conjugated secondary antibody, the GFP-Intercoil or GFP were viewed directly. The nuclei were stained with DAPI. (B) Subcellular localization of p53-Intercoil and GFP-Intercoil in the presence of inclusions formed by muNS-Mi. CEF cells were co-transfected with the plasmids expressing the proteins indicated on the left of the figure, they were fixed at 24 h.p.t. and were then subjected to immunofluorescence such as indicated above. A diagram of what is shown in the immunofluorescence images is depicted on the right of the panels according to the standards of the diagram of FIG. 13.

GFP and p53 protein were chosen to check whether two proteins could be directed to the inclusions, since as has been seen previously, they were incorporated efficiently into the inclusions when fused with the Intercoil. CEF cells were co-transfected with each of the inclusion-forming constructs together with: i) GFP-Intercoil and p53-Intercoil; ii) GFP and p53-Intercoil serving as a control, to determine that Intercoil-free GFP was not incorporated into the inclusions by association with p53; and iii) GFP-Intercoil and untagged p53 which was also used as a control, to show that Intercoil-free p53 was not incorporated into the inclusions by association with GFP. The cells were fixed at 24 h.p.t and subjected to immunofluorescence with monoclonal anti-p53 antibody. The proteins GFP-Intercoil and p53-Intercoil were exclusively localized in the inclusions formed both by muNS (FIG. 35A, bottom panels), and by muNS-Mi (FIG. 35B, bottom panels). Furthermore, in the cells which co-expressed muNS or muNS-Mi together with GFP-Intercoil and p53, the GFP-Intercoil was localized in the inclusions whereas p53 remained in the nucleus (FIGS. 35A and 35B, top panels), and in cells which co-expressed muNS or muNS-Mi together with GFP and p53-Intercoil, the p53-Intercoil was localized in the inclusion bodies whereas GFP was distributed throughout the cell without being efficiently incorporated into the inclusions (FIGS. 35A and 35B, central panels), showing that p53 and GFP was incorporated into the inclusions when they are tagged with the Intercoil and not by association between them. These results show that the inclusions formed by muNS or muNS-Mi are capable of capturing several proteins tagged with the Intercoil domain without altering the integrity of the inclusions nor the activity of the protein incorporated, since GFP continues to emit its characteristic fluorescence, which could be used to: i) favor the assembly of supramolecular complexes in cells for structural study, as has been mentioned above and ii) use these inclusions for generating polyvalent vaccines upon exposing several epitopes in one and the same particulate material.

Figure 36:
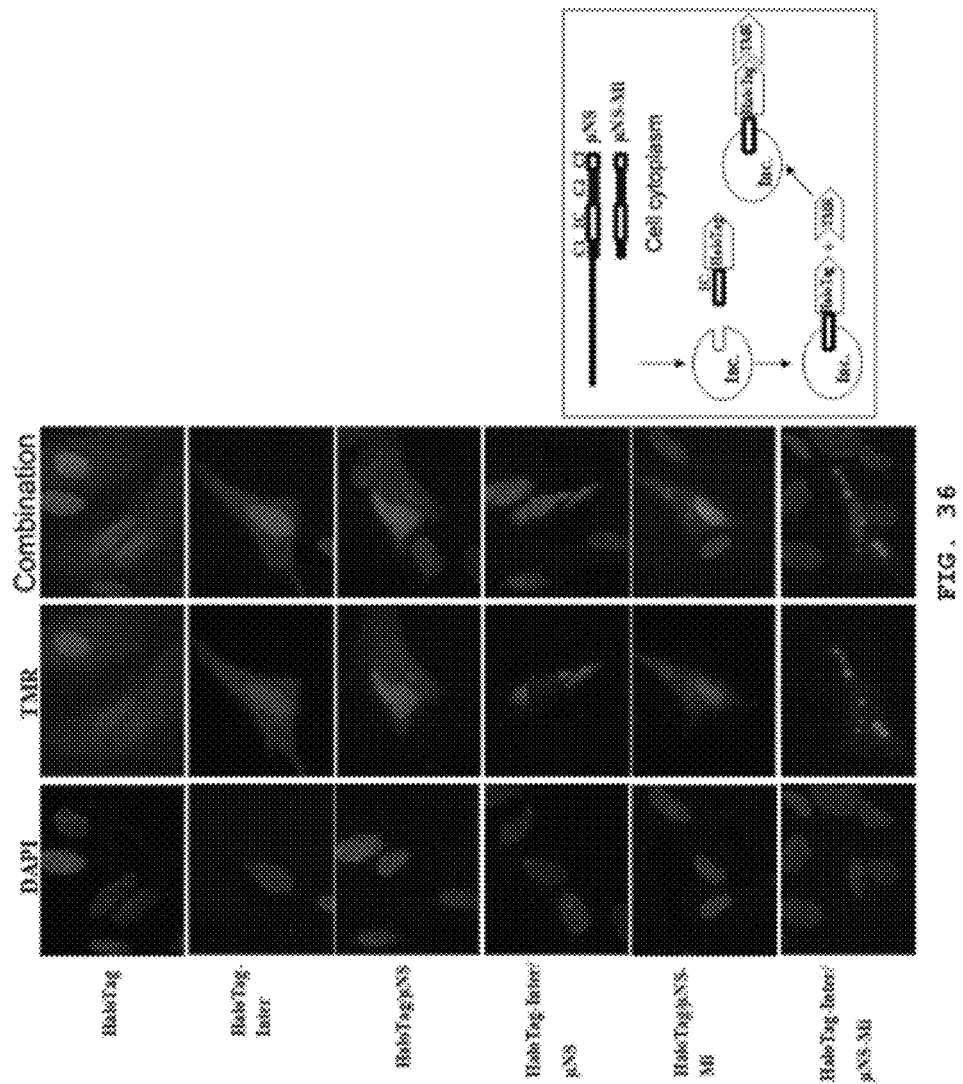
FIG. 36 shows the intracellular distribution of HaloTag and HaloTag-Intercoil in the presence of the inclusions formed by muNS or muNS-Mi. Semi-confluent CEF cells were transfected with the plasmids expressing the proteins indicated on the left of the figure. The cells were tagged with TMR at 24 h.p.t. and were then observed with a fluorescence microscope. The distribution of the HaloTag and the Halotag-intercoil is seen in the central figures. The nuclei were stained with DAPI. A diagram of what is shown in the immunofluorescence images is depicted on the right of the panels according to the standards of the diagram of FIG. 13.

Example 11 muNS-Mi and muNS Protein Efficiently Recruit Halotag-Intercoil without the Latter Losing its Enzymatic Activity The results exposed in other examples show that the GFP protein tagged with the Intercoil is efficiently incorporated into the inclusions formed by muNS and muNS-Mi. Furthermore, it was also confirmed that the recruited protein (GFP) is perfectly folded and is functional, since it continues emitting its characteristic fluorescence. The HaloTag protein was used as an example of another protein which maintains its activity upon being incorporated into the muNS and muNS-Mi inclusions. Said protein is a genetically modified version of a hydrolase catalyzing its covalent binding to a group of ligands (coumarin, Oregon Green, Alexa Flour 448, TMR Ligand and diAcFAM Ligand), which easily cross cell membranes and can be used for labeling proteins fused with HaloTag localized in different cell compartments. To show that the HaloTag is incorporated into the inclusions and maintains its activity once inside the inclusions, the first step was to construct a plasmid expressing the HaloTag protein fused at its carboxyl end to the Intercoil domain, HaloTag-Intercoil being obtained. The identity of said construct was confirmed by means of sequencing the expression plasmid thereof and by means of analyzing the lysates of CEF cells transfected with this plasmid by Western-blot using anti-muNS antibodies (data not shown). For determining the intracellular distribution of HaloTag-Intercoil, CEF cells were transfected with the plasmid HaloTag-Intercoil, and at 24 h post-transfection the cells were tagged with the TMR ligand following the manufacturer's instructions (Promega, Madrid, Spain), they were fixed and analyzed with a fluorescence microscope. Like the untagged HaloTag, the HaloTag-Intercoil fusion protein was distributed in a diffused manner throughout the cell, showing that the fusion of the Intercoil domain to the carboxyl end HaloTag does not modify its intracellular localization (FIG. 36, see top panels). The proteins HaloTag and muNS were then co-expressed and their intracellular distribution was analyzed by means of fluorescence after previously labeling with the TMR ligand. The HaloTag protein only continued to be distributed in a diffused manner throughout the cell, despite that a small part was detected in the muNS inclusions (FIG. 36, central panels), which indicates that the HaloTag, even though not excluded from the inclusions, is not incorporated into same. However, in the cells co-expressing Halotag-Intercoil and muNS, the Halotag is mainly localized in the inclusions (FIG. 36, central panels). This shows that: i) the HaloTag is incorporated into the inclusions when it is fused to the Intercoil, and ii) the HaloTag-Intercoil incorporated into the inclusions is perfectly folded and is functional, since it is capable of catalyzing its covalent binding to its TMR ligand. The same results were repeated upon co-expressing µNS-Mi with HaloTag or HaloTag-Intercoil, which can be seen in the bottom panels in FIG. 36.

The invention claimed is:

1. A fusion protein comprising:
   (i) a first component containing at least one polypeptide of interest; and
   (ii) a second component selected from the group of:
   a polypeptide comprising sequence SEQ ID NO: 2, corresponding to residues 381-448 of avian *Orthoreovirus* muNS protein;
   a polypeptide comprising sequence SEQ ID NO: 3, corresponding to residues 448-477 of avian *Orthoreovirus* muNS protein;
   a polypeptide comprising sequence SEQ ID NO: 4, corresponding to residues 477-542 of avian *Orthoreovirus* muNS protein; and
   a polypeptide comprising sequence SEQ ID NO: 5, corresponding to residues 539-605 of avian *Orthoreovirus* muNS protein,
   wherein the second component does not contain a polypeptide comprising the amino acids of mammalian *Orthoreovirus* muNS protein corresponding to sequence 606-635 (SEQ ID NO: 78) of said avian protein,
   and wherein the first component and the second component originate from different or heterologous proteins.

2. A polynucleotide encoding the fusion protein according to claim 1.

3. A cell including the fusion protein according to claim 1.

4. Fusion protein according to claim 1, further comprising at least one component selected from the group of a peptide to facilitate its purification and a nuclear signaling peptide.

5. A cell including the fusion protein according to claim 4.

6. A cell including the polynucleotide according to claim 2.

* * * * *

SEQUENCE LISTING

<160> NUMBER OF SEQ ID NOS: 78

<210> SEQ ID NO 1
<211> LENGTH: 188
<212> TYPE: PRT
<213> ORGANISM: Avian reovirus

<400> SEQUENCE: 1

```
Pro Ala Ala Leu Leu Ser Lys Ile Ala Asp Leu Gln Arg Ala Asn Arg
1               5                  10                  15

Glu Leu Ser Leu Lys Leu Val Asp Val Gln Pro Ala Arg Glu Asp His
            20                  25                  30

Leu Leu Ala Tyr Leu Asn Glu His Val Cys Val Asn Ala Lys Asp His
        35                  40                  45

Glu Lys Gly Leu Leu Ala Arg Cys Asn Val Ser Gly Asp Ser Ile Ser
    50                  55                  60

Ser Ile Leu Gly Gln Arg Met Lys Asn Arg Glu Arg Phe Glu Thr Arg
65                  70                  75                  80

Leu Arg His Glu Ala Ser Ala Glu Trp Glu Pro Arg Val Glu Ala Leu
                85                  90                  95

Asn Gln Glu Leu Ala Lys Ala Arg Val Glu Gln Gln Asp Met Met Thr
            100                 105                 110
```

```
Gln Ser Leu Gln Tyr Leu Asn Glu Arg Asp Glu Leu Leu Gln Glu Val
            115                 120                 125

Asp Glu Leu Lys Arg Glu Leu Thr Thr Leu Arg Ser Ala Asn Val Arg
130                 135                 140

Leu Asn Ala Asp Asn His Arg Met Ser Arg Ala Thr Arg Val Gly Asp
145                 150                 155                 160

Ala Phe Val Ser Asp Val Glu Pro Leu Pro Ser Gly Ile Pro Gly Glu
                165                 170                 175

Ser Lys Pro Ser Met Glu Glu Leu Val Asp Asp Leu
            180                 185

<210> SEQ ID NO 2
<211> LENGTH: 68
<212> TYPE: PRT
<213> ORGANISM: Avian reovirus

<400> SEQUENCE: 2

Met Pro Ser Phe Leu Leu Gly Ala Leu Lys Gln Ser Gly Gly Gln Leu
1               5                   10                  15

Leu Glu His Tyr Arg Cys Asp Ala Ala Asn Arg Tyr Gly Ser Pro Thr
            20                  25                  30

Val Pro Ile Ser His Pro Pro Cys Ser Lys Cys Pro Glu Leu Lys
        35                  40                  45

Glu Gln Ile Ala Lys Leu Ser Ser Ser Pro Ile Pro Lys Val Asp Ser
50                  55                  60

Ser Val Gly Pro
65

<210> SEQ ID NO 3
<211> LENGTH: 30
<212> TYPE: PRT
<213> ORGANISM: Avian reovirus

<400> SEQUENCE: 3

Pro Ala Ala Leu Leu Ser Lys Ile Ala Asp Leu Gln Arg Ala Asn Arg
1               5                   10                  15

Glu Leu Ser Leu Lys Leu Val Asp Val Gln Pro Ala Arg Glu
            20                  25                  30

<210> SEQ ID NO 4
<211> LENGTH: 66
<212> TYPE: PRT
<213> ORGANISM: Avian reovirus

<400> SEQUENCE: 4

Glu Asp His Leu Leu Ala Tyr Leu Asn Glu His Val Cys Val Asn Ala
1               5                   10                  15

Lys Asp His Glu Lys Gly Leu Leu Ala Arg Cys Asn Val Ser Gly Asp
            20                  25                  30

Ser Ile Ser Ser Ile Leu Gly Gln Arg Met Lys Asn Arg Glu Arg Phe
        35                  40                  45

Glu Thr Arg Leu Arg His Glu Ala Ser Ala Glu Trp Glu Pro Arg Val
50                  55                  60

Glu Ala
65

<210> SEQ ID NO 5
<211> LENGTH: 67
<212> TYPE: PRT
```

-continued

```
<213> ORGANISM: Avian reovirus

<400> SEQUENCE: 5

Arg Val Glu Ala Leu Asn Gln Glu Leu Ala Lys Ala Arg Val Glu Gln
1               5                   10                  15

Gln Asp Met Met Thr Gln Ser Leu Gln Tyr Leu Asn Glu Arg Asp Glu
            20                  25                  30

Leu Leu Gln Glu Val Asp Glu Leu Lys Arg Glu Leu Thr Thr Leu Arg
        35                  40                  45

Ser Ala Asn Val Arg Leu Asn Ala Asp Asn His Arg Met Ser Arg Ala
    50                  55                  60

Thr Arg Val
65

<210> SEQ ID NO 6
<211> LENGTH: 31
<212> TYPE: PRT
<213> ORGANISM: Avian reovirus

<400> SEQUENCE: 6

Val Gly Asp Ala Phe Val Ser Asp Val Glu Pro Leu Pro Ser Gly Ile
1               5                   10                  15

Pro Gly Glu Ser Lys Pro Ser Met Glu Glu Leu Val Asp Asp Leu
            20                  25                  30

<210> SEQ ID NO 7
<211> LENGTH: 34
<212> TYPE: DNA
<213> ORGANISM: Artificial
<220> FEATURE:
<223> OTHER INFORMATION: Forward primer for amplifying muNS (448-635)

<400> SEQUENCE: 7
gcggaattca tcatgccagc cgtactgctg tcta                              34

<210> SEQ ID NO 8
<211> LENGTH: 33
<212> TYPE: DNA
<213> ORGANISM: Artificial
<220> FEATURE:
<223> OTHER INFORMATION: Reverse primer for amplifying muNS (448-635)

<400> SEQUENCE: 8
gcgtctagat cacagatcat ccaccaattc ttc                               33

<210> SEQ ID NO 9
<211> LENGTH: 30
<212> TYPE: DNA
<213> ORGANISM: Artificial
<220> FEATURE:
<223> OTHER INFORMATION: Forward primer for amplifying pVP16-muNS

<400> SEQUENCE: 9
gcggaattca tcatggcgtc aaccaagtgg                                   30

<210> SEQ ID NO 10
<211> LENGTH: 33
<212> TYPE: DNA
<213> ORGANISM: Artificial
<220> FEATURE:
<223> OTHER INFORMATION: Reverse primer for amplifying pVP16-muNS

<400> SEQUENCE: 10
```
gcgtctagat cacagatcat ccaccaattc ttc                                33

<210> SEQ ID NO 11
<211> LENGTH: 32
<212> TYPE: DNA
<213> ORGANISM: Artificial
<220> FEATURE:
<223> OTHER INFORMATION: Forward primer for amplifying GFP-muNS-NLS AgT

<400> SEQUENCE: 11
gcgggatccg taccatggtg agcaagggcg ag                                 32

<210> SEQ ID NO 12
<211> LENGTH: 33
<212> TYPE: DNA
<213> ORGANISM: Artificial
<220> FEATURE:
<223> OTHER INFORMATION: Reverse primer for amplifying GFP-muNS-NLS AgT

<400> SEQUENCE: 12
gcgtctagat cacagatcat ccaccaattc ttc                                33

<210> SEQ ID NO 13
<211> LENGTH: 60
<212> TYPE: DNA
<213> ORGANISM: Artificial
<220> FEATURE:
<223> OTHER INFORMATION: Forward primer for amplifying NLS-AgT-muNS

<400> SEQUENCE: 13
gcggaattca tcatgggacc aaagaagaag cgtaaagtta tcatggcgtc aaccaagtgg   60

<210> SEQ ID NO 14
<211> LENGTH: 60
<212> TYPE: DNA
<213> ORGANISM: Artificial
<220> FEATURE:
<223> OTHER INFORMATION: Forward primer for amplifying NLS-AgT-GFP-muNS

<400> SEQUENCE: 14
gcgggatcca tcatgggacc aaagaagaag cgtaaagtta ccatggtgag caagggcgag   60

<210> SEQ ID NO 15
<211> LENGTH: 31
<212> TYPE: DNA
<213> ORGANISM: Artificial
<220> FEATURE:
<223> OTHER INFORMATION: Forward primer for amplifying GFP-muNS(1-477)

<400> SEQUENCE: 15
gcggaattct atcatggcgt caaccaagtg g                                  31

<210> SEQ ID NO 16
<211> LENGTH: 33
<212> TYPE: DNA
<213> ORGANISM: Artificial
<220> FEATURE:
<223> OTHER INFORMATION: Reverse primer for amplifying GFP-muNS(1-477)

<400> SEQUENCE: 16
gcgggatcct tattcccgag caggttgaac atc                                33

<210> SEQ ID NO 17
<211> LENGTH: 31
<212> TYPE: DNA
<213> ORGANISM: Artificial

```
<220> FEATURE:
<223> OTHER INFORMATION: Reverse primer for amplifying GFP-muNS (1-448)

<400> SEQUENCE: 17
gcgggatcct tatggaccaa cggacgaatc g                                    31

<210> SEQ ID NO 18
<211> LENGTH: 33
<212> TYPE: DNA
<213> ORGANISM: Artificial
<220> FEATURE:
<223> OTHER INFORMATION: Reverse primer for amplifying GFP-muNS (1-380)

<400> SEQUENCE: 18
gcgggatcct tatggagacc gtctagcgag aag                                  33

<210> SEQ ID NO 19
<211> LENGTH: 32
<212> TYPE: DNA
<213> ORGANISM: Artificial
<220> FEATURE:
<223> OTHER INFORMATION: Reverse primer for amplifying GFP-muNS (1-154)

<400> SEQUENCE: 19
gcgggatcct taatcggggg aatcagcggt gg                                   32

<210> SEQ ID NO 20
<211> LENGTH: 27
<212> TYPE: DNA
<213> ORGANISM: Artificial
<220> FEATURE:
<223> OTHER INFORMATION: Forward primer for amplifying GFP-muNS (448-
      635)

<400> SEQUENCE: 20
gcggaattct ccagccgtac tgctgtc                                         27

<210> SEQ ID NO 21
<211> LENGTH: 33
<212> TYPE: DNA
<213> ORGANISM: Artificial
<220> FEATURE:
<223> OTHER INFORMATION: Reverse primer for amplifying GFP-muNS (448-
      635)

<400> SEQUENCE: 21
gcgggatcct cacagatcat ccaccaattc ttc                                  33

<210> SEQ ID NO 22
<211> LENGTH: 32
<212> TYPE: DNA
<213> ORGANISM: Artificial
<220> FEATURE:
<223> OTHER INFORMATION: Forward primer for amplifying GFP-muNS (605-
      635)

<400> SEQUENCE: 22
gcggaattct gtcggagacg ccttcgtcag tg                                   32

<210> SEQ ID NO 23
<211> LENGTH: 32
<212> TYPE: DNA
<213> ORGANISM: Artificial
<220> FEATURE:
<223> OTHER INFORMATION: Forward primer for amplifying GFP-muNS (477-
      542)
```

<400> SEQUENCE: 23
gcggaattct gaagatcact tgttggctta tc        32

<210> SEQ ID NO 24
<211> LENGTH: 34
<212> TYPE: DNA
<213> ORGANISM: Artificial
<220> FEATURE:
<223> OTHER INFORMATION: Reverse primer for amplifying GFP-muNS (477-
      542)

<400> SEQUENCE: 24
gcgggatcct tacgcttcca cacggggttc ccac        34

<210> SEQ ID NO 25
<211> LENGTH: 32
<212> TYPE: DNA
<213> ORGANISM: Artificial
<220> FEATURE:
<223> OTHER INFORMATION: Forward primer for amplifying GFP-muNS (539-
      605)

<400> SEQUENCE: 25
gcggaattct cgtgtggaag cgttaaacca ag        32

<210> SEQ ID NO 26
<211> LENGTH: 34
<212> TYPE: DNA
<213> ORGANISM: Artificial
<220> FEATURE:
<223> OTHER INFORMATION: Reverse primer for amplifying GFP-muNS (539-
      605)

<400> SEQUENCE: 26
gcgggatcct tagacacgtg tcgcacgact catc        34

<210> SEQ ID NO 27
<211> LENGTH: 32
<212> TYPE: DNA
<213> ORGANISM: Artificial
<220> FEATURE:
<223> OTHER INFORMATION: Forward primer for amplifying GFP-muNS (381-
      448

<400> SEQUENCE: 27
gcggaattct atgccatcct tcttactcgg tg        32

<210> SEQ ID NO 28
<211> LENGTH: 44
<212> TYPE: DNA
<213> ORGANISM: Artificial
<220> FEATURE:
<223> OTHER INFORMATION: Forward primer for amplifying GFP-muNS (477-
      542)

<400> SEQUENCE: 28
gcggaattct atcgagggaa gggaagatca cttgttggct tatc        44

<210> SEQ ID NO 29
<211> LENGTH: 30
<212> TYPE: DNA
<213> ORGANISM: Artificial
<220> FEATURE:
<223> OTHER INFORMATION: Forward primer for amplifying muNS (1-154)-HA

<400> SEQUENCE: 29

-continued gcggaattca tcatggcgtc aaccaagtgg                30

<210> SEQ ID NO 30
<211> LENGTH: 59
<212> TYPE: DNA
<213> ORGANISM: Artificial
<220> FEATURE:
<223> OTHER INFORMATION: Reverse primer for amplifying muNS (1-154)-HA

<400> SEQUENCE: 30
gcgtctagat tacgcataat ccggcacatc atacggataa tcgggggaat cagcggtgg    59

<210> SEQ ID NO 31
<211> LENGTH: 30
<212> TYPE: DNA
<213> ORGANISM: Artificial
<220> FEATURE:
<223> OTHER INFORMATION: Forward primer for amplifying muNS (1-380)-HA

<400> SEQUENCE: 31
gcggaattca tcatggcgtc aaccaagtgg                30

<210> SEQ ID NO 32
<211> LENGTH: 60
<212> TYPE: DNA
<213> ORGANISM: Artificial
<220> FEATURE:
<223> OTHER INFORMATION: Reverse primer for amplifying muNS (1-380)-HA

<400> SEQUENCE: 32
gcgtctagat tacgcataat ccggcacatc atacggatat ggagaccgtc tagcgagaag    60

<210> SEQ ID NO 33
<211> LENGTH: 30
<212> TYPE: DNA
<213> ORGANISM: Artificial
<220> FEATURE:
<223> OTHER INFORMATION: Forward primer for amplifying muNS (1-448)-HA

<400> SEQUENCE: 33
gcggaattca tcatggcgtc aaccaagtgg                30

<210> SEQ ID NO 34
<211> LENGTH: 58
<212> TYPE: DNA
<213> ORGANISM: Artificial
<220> FEATURE:
<223> OTHER INFORMATION: Reverse primer for amplifying muNS (1-448)-HA

<400> SEQUENCE: 34
gcgtctagat tacgcataat ccggcacatc atacggatat ggaccaacgg acgaatcg      58

<210> SEQ ID NO 35
<211> LENGTH: 30
<212> TYPE: DNA
<213> ORGANISM: Artificial
<220> FEATURE:
<223> OTHER INFORMATION: Forward primer for amplifying muNS (1-477)-HA

<400> SEQUENCE: 35
gcggaattca tcatggcgtc aaccaagtgg                30

<210> SEQ ID NO 36
<211> LENGTH: 60
<212> TYPE: DNA
<213> ORGANISM: Artificial

<220> FEATURE:
<223> OTHER INFORMATION: Reverse primer for amplifying muNS (1-477)-HA

<400> SEQUENCE: 36
gcgtctagat tacgcataat ccggcacatc atacggatat tcccgagcag gttgaacatc        60

<210> SEQ ID NO 37
<211> LENGTH: 40
<212> TYPE: DNA
<213> ORGANISM: Artificial
<220> FEATURE:
<223> OTHER INFORMATION: Forward primer for amplifying muNS (539-635)-HA

<400> SEQUENCE: 37
gcggaattca tcatggcgcg tgtggaagcg ttaaaccaag        40

<210> SEQ ID NO 38
<211> LENGTH: 60
<212> TYPE: DNA
<213> ORGANISM: Artificial
<220> FEATURE:
<223> OTHER INFORMATION: Reverse primer for amplifying muNS (539-635)-HA

<400> SEQUENCE: 38
gcgtctagat cacgcataat ccggcacatc atacggatac agatcatcca ccaattcttc        60

<210> SEQ ID NO 39
<211> LENGTH: 40
<212> TYPE: DNA
<213> ORGANISM: Artificial
<220> FEATURE:
<223> OTHER INFORMATION: Forward primer for amplifying muNS (539-605)-HA

<400> SEQUENCE: 39
gcggaattca tcatggcgcg tgtggaagcg ttaaaccaag        40

<210> SEQ ID NO 40
<211> LENGTH: 61
<212> TYPE: DNA
<213> ORGANISM: Artificial
<220> FEATURE:
<223> OTHER INFORMATION: Reverse primer for amplifying muNS (539-605)-HA

<400> SEQUENCE: 40
gcgtctagat cacgcataat ccggcacatc atacggatag acacgtgtcg cacgactcat        60
c        61

<210> SEQ ID NO 41
<211> LENGTH: 37
<212> TYPE: DNA
<213> ORGANISM: Artificial
<220> FEATURE:
<223> OTHER INFORMATION: Forward primer for amplifying muNS (477-542)-HA

<400> SEQUENCE: 41
gcggaattca tcatggaaga tcacttgttg gcttatc        37

<210> SEQ ID NO 42
<211> LENGTH: 61
<212> TYPE: DNA
<213> ORGANISM: Artificial
<220> FEATURE:
<223> OTHER INFORMATION: Reverse primer for amplifying muNS (477-542)-HA

<400> SEQUENCE: 42

```
gcgtctagat cacgcataat ccggcacatc atacggatac gcttccacac ggggttccca      60
c                                                                      61

<210> SEQ ID NO 43
<211> LENGTH: 34
<212> TYPE: DNA
<213> ORGANISM: Artificial
<220> FEATURE:
<223> OTHER INFORMATION: Forward primer for amplifying muNS (381-448)-HA

<400> SEQUENCE: 43
gcggaattca tcatgccatc cttcttactc ggtg                                  34

<210> SEQ ID NO 44
<211> LENGTH: 58
<212> TYPE: DNA
<213> ORGANISM: Artificial
<220> FEATURE:
<223> OTHER INFORMATION: Reverse primer for amplifying muNS (381-448)-HA

<400> SEQUENCE: 44
gcgtctagat cacgcataat ccggcacatc atacggatat ggaccaacgg acgaatcg        58

<210> SEQ ID NO 45
<211> LENGTH: 40
<212> TYPE: DNA
<213> ORGANISM: Artificial
<220> FEATURE:
<223> OTHER INFORMATION: Forward primer for amplifying muNS (477-542)

<400> SEQUENCE: 45
gcgtctagaa tcatggcgga agatcacttg ttggcttatc                            40

<210> SEQ ID NO 46
<211> LENGTH: 34
<212> TYPE: DNA
<213> ORGANISM: Artificial
<220> FEATURE:
<223> OTHER INFORMATION: Reverse primer for amplifying muNS (477-542)

<400> SEQUENCE: 46
gcggggccct tacgcttcca cacggggttc ccac                                  34

<210> SEQ ID NO 47
<211> LENGTH: 35
<212> TYPE: DNA
<213> ORGANISM: Artificial
<220> FEATURE:
<223> OTHER INFORMATION: Forward primer for amplifying p53

<400> SEQUENCE: 47
gcgggatcca tcatggagga gccgcagtca gatcc                                 35

<210> SEQ ID NO 48
<211> LENGTH: 34
<212> TYPE: DNA
<213> ORGANISM: Artificial
<220> FEATURE:
<223> OTHER INFORMATION: Reverse primer for amplifying p53

<400> SEQUENCE: 48
gcggaattcg tctgagtcag gcccttctgt cttg                                  34

<210> SEQ ID NO 49
<211> LENGTH: 30
```

```
<212> TYPE: DNA
<213> ORGANISM: Artificial
<220> FEATURE:
<223> OTHER INFORMATION: Forward primer for amplifying GFP-Xa-muNS(477-
      542)

<400> SEQUENCE: 49
gcgggatcca ccatggtgag caagggcgag                                    30

<210> SEQ ID NO 50
<211> LENGTH: 34
<212> TYPE: DNA
<213> ORGANISM: Artificial
<220> FEATURE:
<223> OTHER INFORMATION: Reverse primer for amplifying GFP-Xa-muNS(477-
      542)

<400> SEQUENCE: 50
gcgtctagat tacgcttcca cacggggttc ccac                               34

<210> SEQ ID NO 51
<211> LENGTH: 30
<212> TYPE: DNA
<213> ORGANISM: Artificial
<220> FEATURE:
<223> OTHER INFORMATION: Forward primer for amplifying GFP

<400> SEQUENCE: 51
gcggaattca ccatggtgag caagggcgag                                    30

<210> SEQ ID NO 52
<211> LENGTH: 33
<212> TYPE: DNA
<213> ORGANISM: Artificial
<220> FEATURE:
<223> OTHER INFORMATION: Reverse primer for amplifying GFP

<400> SEQUENCE: 52
gcgtctagat tacttgtaca gctcgtccat gcc                                33

<210> SEQ ID NO 53
<211> LENGTH: 36
<212> TYPE: DNA
<213> ORGANISM: Artificial
<220> FEATURE:
<223> OTHER INFORMATION: Forward primer for amplifying HaloTag

<400> SEQUENCE: 53
gcgggatcca ccatgggctc cgaaatcggt acaggc                             36

<210> SEQ ID NO 54
<211> LENGTH: 38
<212> TYPE: DNA
<213> ORGANISM: Artificial
<220> FEATURE:
<223> OTHER INFORMATION: Reverse primer for amplifying HaloTag

<400> SEQUENCE: 54
gcataagaat gcggccgcca gccggccagc ccggggag                           38

<210> SEQ ID NO 55
<211> LENGTH: 721
<212> TYPE: PRT
<213> ORGANISM: Mammalian reovirus

<400> SEQUENCE: 55
```

-continued

```
Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
            20                  25                  30

Gln Ser Phe Thr Pro Ser Val Asp Met Ser Gln Ser Arg Glu Phe Leu
                35                  40                  45

Thr Lys Ala Ile Glu Gln Gly Ser Met Ser Ile Pro Tyr Gln His Val
    50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95

Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
            115                 120                 125

Ala Ile Lys Pro Gly Met Ser Leu Gln Asp Ala Ile Thr Ala Phe Ile
    130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Lys Glu Ala Lys Val Ala Asp Glu Leu Met Leu Phe
            180                 185                 190

Gly Leu Asp His Arg Gly Pro Gln Gln Leu Asp Val Ser Asp Ala Lys
            195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Thr Tyr Asp Glu
            260                 265                 270

His Asp Gly Arg Met Ala Asp Gln Lys Gln Ser Gly Leu Ile Leu Cys
            275                 280                 285

Thr Lys Asp Glu Val Leu Ala Glu Gln Thr Ile Phe Lys Leu Asp Ala
    290                 295                 300

Pro Asp Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335

His Ala Ala Gln Arg Ser Gly Gln Arg Ser Val Leu Asp Asp Leu Tyr
            340                 345                 350

Ala Asn Thr Gln Val Ile Ser Ile Thr Ser Ala Ala Leu Lys Trp Val
    355                 360                 365

Val Lys His Gly Val Ser Asp Gly Ile Val Asn Arg Lys Asn Val Lys
    370                 375                 380

Val Cys Val Gly Phe Asp Pro Leu Tyr Thr Leu Ser Thr His Asn Gly
385                 390                 395                 400

Val Ser Leu Cys Ala Leu Leu Met Asp Glu Lys Leu Ser Val Leu Asn
                405                 410                 415

Ser Ala Cys Arg Met Thr Leu Arg Ser Leu Met Lys Thr Gly Arg Asp
```

```
            420                 425                 430
Val Asp Ala His Arg Ala Phe Gln Arg Val Leu Ser Gln Gly Tyr Thr
            435                 440                 445

Ser Leu Met Cys Tyr Tyr His Pro Ser Arg Lys Leu Ala Tyr Gly Glu
    450                 455                 460

Val Leu Phe Leu Glu Arg Ser Asn Asp Val Thr Asp Gly Ile Lys Leu
465                 470                 475                 480

Gln Leu Asp Ala Ser Arg Gln Cys His Glu Cys Pro Val Leu Gln Gln
                485                 490                 495

Lys Val Val Glu Leu Glu Lys Gln Ile Ile Met Gln Lys Ser Ile Gln
            500                 505                 510

Ser Asp Pro Thr Pro Val Ala Leu Gln Pro Leu Leu Ser Gln Leu Arg
        515                 520                 525

Glu Leu Ser Ser Glu Val Thr Arg Leu Gln Met Glu Leu Ser Arg Ala
    530                 535                 540

Gln Ser Leu Asn Ala Gln Leu Glu Ala Asp Val Lys Ser Ala Gln Ser
545                 550                 555                 560

Cys Ser Leu Asp Met Tyr Leu Arg His His Thr Cys Ile Asn Gly His
                565                 570                 575

Ala Lys Glu Asp Glu Leu Leu Asp Ala Val Arg Val Ala Pro Asp Val
            580                 585                 590

Arg Arg Glu Ile Met Lys Arg Ser Glu Val Arg Gln Gly Trp Cys
        595                 600                 605

Glu Arg Ile Ser Lys Glu Ala Ala Lys Cys Gln Thr Val Ile Asp
    610                 615                 620

Asp Leu Thr Leu Met Asn Gly Lys Gln Ala Gln Glu Ile Thr Glu Leu
625                 630                 635                 640

Arg Asp Ser Ala Glu Lys Tyr Glu Lys Gln Ile Ala Glu Leu Val Ser
                645                 650                 655

Thr Ile Thr Gln Asn Gln Ile Thr Tyr Gln Gln Glu Leu Gln Ala Leu
                660                 665                 670

Val Ala Lys Asn Val Glu Leu Asp Ala Leu Asn Gln Arg Gln Ala Lys
            675                 680                 685

Ser Leu Arg Ile Thr Pro Ser Leu Leu Ser Ala Thr Pro Ile Asp Ser
        690                 695                 700

Ala Asp Gly Val Ala Asp Leu Ile Asp Phe Ser Val Pro Thr Asp Glu
705                 710                 715                 720

Leu

<210> SEQ ID NO 56
<211> LENGTH: 635
<212> TYPE: PRT
<213> ORGANISM: Avian reovirus

<400> SEQUENCE: 56

Met Ala Ser Thr Lys Trp Gly Asp Lys Pro Met Ser Val Ser Met Ser
1               5                   10                  15

His Asp Gly Ser Ser Ile Arg Ser Ala Ala Ser Gln Phe Leu Ser Gly
            20                  25                  30

Pro Leu Phe His Ser Thr Pro Ile Pro Pro Gln Arg Lys Thr Val Leu
        35                  40                  45

Leu Lys Phe Met Ile Gly Asp Glu Leu Val Thr Val Gln Gly Ala Leu
    50                  55                  60

Ala Pro Phe Asp Glu Tyr Trp Tyr Asp Asn Gln Pro Leu Leu Ala Gln
```

-continued

```
              65                  70                  75                  80
Ala Val Glu Met Leu Ala Ser Ala Asp Arg Leu Arg Gln Phe Glu His
                     85                  90                  95
Tyr Glu Lys Phe Leu Leu Lys Lys Gly His Gln Ile Thr Glu Ile Met
                    100                 105                 110
Asn Arg Leu Arg Leu Phe Phe Thr Asp Val Leu Lys Val Lys Met Glu
                    115                 120                 125
Ala Asp Ala Leu Pro Ala Leu Ala Gln Tyr Leu Met Val Gly Thr Leu
            130                 135                 140
Glu Ala Val Ser Thr Ala Asp Ser Pro Asp Ala Cys Val Pro Val Thr
145                 150                 155                 160
Ser Lys Ile Leu Ala Lys Gln Gln Thr Ile Ala Lys Ser Pro Gly Arg
                    165                 170                 175
Leu Asp Glu Glu Glu Tyr Asn Val Ile Arg Ser Arg Phe Leu Thr His
                    180                 185                 190
Glu Val Phe Asp Leu Thr Ser Asp Leu Pro Gly Val Gln Pro Phe Met
            195                 200                 205
Asp Met Tyr Tyr Ala Thr Val Pro Arg Ala Asp Ser Thr Gly Trp Cys
            210                 215                 220
Val Tyr Arg Arg Lys Gly Leu Leu Ile His Ala Pro Asp Glu Gln Phe
225                 230                 235                 240
Ser Asp Leu Thr Ile Phe Ser Thr Arg Leu Thr Ala Ser Arg Glu Leu
                    245                 250                 255
Gln Leu Val Ala Gly Asp Val Ala Val Ala Cys Phe Asp Leu Met Asp
            260                 265                 270
Val Ser Asp Ile Ala Pro Ser His His Ala Ser Val Gln Glu Glu Arg
            275                 280                 285
Thr Leu Gly Thr Ser Arg Tyr Ser Asn Val Thr Ala Asn Asp His Pro
            290                 295                 300
Leu Val Phe Phe Ser Pro Ser Ala Leu Arg Trp Ala Ile Asp His Ala
305                 310                 315                 320
Cys Thr Asp Ser Leu Val Ser Thr Arg Asn Ile Arg Val Cys Val Gly
                    325                 330                 335
Ile Asp Pro Leu Val Thr Arg Trp Thr Arg Asp Gly Val Gln Glu Ala
                    340                 345                 350
Ala Ile Leu Met Asp Asp Lys Leu Pro Ser Ala Gly Arg Ala Arg Met
            355                 360                 365
Ala Leu Arg Thr Leu Leu Leu Ala Arg Arg Ser Pro Met Thr Ser Phe
            370                 375                 380
Leu Leu Gly Ala Leu Lys Gln Ser Gly Gly Gln Leu Met Glu His Tyr
385                 390                 395                 400
Arg Cys Asp Ala Ala Asn Arg Tyr Gly Ser Pro Thr Val Pro Val Ser
                    405                 410                 415
His Ser Pro Pro Cys Ser Lys Cys Pro Glu Leu Lys Glu Gln Ile Thr
                    420                 425                 430
Lys Leu Ser Ser Ser Pro Leu Pro Lys Ile Asp Ser Asn Val Gly Pro
            435                 440                 445
Ala Ala Leu Leu Ser Lys Ile Ala Asp Leu Gln Arg Ala Asn Arg Glu
            450                 455                 460
Leu Ser Leu Lys Leu Val Asp Val Gln Pro Ala Arg Glu Asp His Leu
465                 470                 475                 480
Leu Ala Tyr Leu Asn Glu His Val Cys Val Asn Ala Lys Asp His Glu
                    485                 490                 495
```

```
Lys Gly Leu Leu Ser Arg Cys Asn Val Ser Gly Asp Ser Ile Ser Ser
            500                 505                 510

Ile Leu Gly Gln Arg Val Lys Asn Arg Glu Arg Phe Glu Thr Arg Leu
            515                 520                 525

Arg His Glu Ala Ser Ala Glu Trp Glu Pro Arg Val Glu Ala Leu Asn
            530                 535                 540

Gln Glu Leu Ala Lys Ala Arg Val Glu Gln Asp Met Met Thr Gln
545                 550                 555                 560

Ser Leu Gln Tyr Leu Asn Glu Arg Asp Glu Leu His Glu Val Asp
                565                 570                 575

Glu Leu Lys Arg Glu Leu Thr Thr Leu Arg Ser Ala Asn Val Arg Leu
            580                 585                 590

Asn Ala Asp Asn His Arg Met Ser Arg Ala Thr Arg Val Gly Asp Ala
            595                 600                 605

Phe Val Ser Asp Val Glu Pro Leu Pro Ser Gly Ile Pro Gly Glu Ser
            610                 615                 620

Lys Pro Ser Met Glu Glu Leu Val Asp Asp Leu
625                 630                 635

<210> SEQ ID NO 57
<211> LENGTH: 7
<212> TYPE: PRT
<213> ORGANISM: Artificial
<220> FEATURE:
<223> OTHER INFORMATION: SV40 T-antigen NLS

<400> SEQUENCE: 57

Pro Lys Lys Lys Arg Lys Val
1               5

<210> SEQ ID NO 58
<211> LENGTH: 16
<212> TYPE: PRT
<213> ORGANISM: Artificial
<220> FEATURE:
<223> OTHER INFORMATION: Nucleoplasmin NLS

<400> SEQUENCE: 58

Lys Arg Pro Ala Ala Thr Lys Lys Ala Gly Gln Ala Lys Lys Lys Lys
1               5                   10                  15

<210> SEQ ID NO 59
<211> LENGTH: 9
<212> TYPE: PRT
<213> ORGANISM: Artificial
<220> FEATURE:
<223> OTHER INFORMATION: NLS similar to the homeodomain of S.cerevisiae
      MATa2 protein

<400> SEQUENCE: 59

Pro Ala Ala Lys Arg Val Lys Leu Asp
1               5

<210> SEQ ID NO 60
<211> LENGTH: 11
<212> TYPE: PRT
<213> ORGANISM: Artificial
<220> FEATURE:
<223> OTHER INFORMATION: NLS similar to the homeodomain of c-myc protein

<400> SEQUENCE: 60

Arg Gln Arg Arg Asn Glu Leu Lys Arg Ser Phe
```

```
1               5                   10
```

<210> SEQ ID NO 61
<211> LENGTH: 38
<212> TYPE: PRT
<213> ORGANISM: Artificial
<220> FEATURE:
<223> OTHER INFORMATION: hRNPA1 M9 protein NLS

<400> SEQUENCE: 61

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35
```

<210> SEQ ID NO 62
<211> LENGTH: 41
<212> TYPE: PRT
<213> ORGANISM: Artificial
<220> FEATURE:
<223> OTHER INFORMATION: NLS of IBB domain of importin alpha

<400> SEQUENCE: 62

```
Arg Met Arg Lys Phe Lys Asn Lys Gly Lys Asp Thr Ala Glu Leu Arg
1               5                   10                  15

Arg Arg Arg Val Glu Val Ser Val Glu Leu Arg Lys Ala Lys Lys Asp
            20                  25                  30

Glu Gln Ile Leu Lys Arg Arg Asn Val
        35                  40
```

<210> SEQ ID NO 63
<211> LENGTH: 8
<212> TYPE: PRT
<213> ORGANISM: Artificial
<220> FEATURE:
<223> OTHER INFORMATION: NLS of myoma T protein

<400> SEQUENCE: 63

```
Val Ser Arg Lys Arg Pro Arg Pro
1               5
```

<210> SEQ ID NO 64
<211> LENGTH: 8
<212> TYPE: PRT
<213> ORGANISM: Artificial
<220> FEATURE:
<223> OTHER INFORMATION: NLS of myoma T protein

<400> SEQUENCE: 64

```
Pro Pro Lys Lys Ala Arg Glu Asp
1               5
```

<210> SEQ ID NO 65
<211> LENGTH: 12
<212> TYPE: PRT
<213> ORGANISM: Artificial
<220> FEATURE:
<223> OTHER INFORMATION: NLS of mouse c-abl IV protein

<400> SEQUENCE: 65

```
Ser Ala Leu Ile Lys Lys Lys Lys Lys Met Ala Pro
1               5                   10
```

<210> SEQ ID NO 66
<211> LENGTH: 5
<212> TYPE: PRT
<213> ORGANISM: Artificial
<220> FEATURE:
<223> OTHER INFORMATION: NLS of influenza virus NS1 protein

<400> SEQUENCE: 66

Asp Arg Leu Arg Arg
1               5

<210> SEQ ID NO 67
<211> LENGTH: 7
<212> TYPE: PRT
<213> ORGANISM: Artificial
<220> FEATURE:
<223> OTHER INFORMATION: NLS of influenza virus NS1 protein

<400> SEQUENCE: 67

Pro Lys Gln Lys Lys Arg Lys
1               5

<210> SEQ ID NO 68
<211> LENGTH: 10
<212> TYPE: PRT
<213> ORGANISM: Artificial
<220> FEATURE:
<223> OTHER INFORMATION: NLS of hepatitis virus delta antigen

<400> SEQUENCE: 68

Arg Lys Leu Lys Lys Lys Ile Lys Lys Leu
1               5                   10

<210> SEQ ID NO 69
<211> LENGTH: 10
<212> TYPE: PRT
<213> ORGANISM: Artificial
<220> FEATURE:
<223> OTHER INFORMATION: NLS of mouse Mx1 protein

<400> SEQUENCE: 69

Arg Glu Lys Lys Lys Phe Leu Lys Arg Arg
1               5                   10

<210> SEQ ID NO 70
<211> LENGTH: 20
<212> TYPE: PRT
<213> ORGANISM: Artificial
<220> FEATURE:
<223> OTHER INFORMATION: NLS of poly (ADP-ribose) polymerase

<400> SEQUENCE: 70

Lys Arg Lys Gly Asp Glu Val Asp Gly Val Asp Glu Val Ala Lys Lys
1               5                   10                  15

Lys Ser Lys Lys
            20

<210> SEQ ID NO 71
<211> LENGTH: 17
<212> TYPE: PRT
<213> ORGANISM: Artificial
<220> FEATURE:
<223> OTHER INFORMATION: NLS of human steroid hormone receptors

<400> SEQUENCE: 71

Arg Lys Cys Leu Gln Ala Gly Met Asn Leu Glu Ala Arg Lys Thr Lys

Lys

<210> SEQ ID NO 72
<211> LENGTH: 10
<212> TYPE: PRT
<213> ORGANISM: Artificial
<220> FEATURE:
<223> OTHER INFORMATION: NLS of avian reovirus p17 protein

<400> SEQUENCE: 72

Ile Ala Ala Lys Arg Gly Arg Gln Leu Asp
1               5                   10

<210> SEQ ID NO 73
<211> LENGTH: 5
<212> TYPE: PRT
<213> ORGANISM: Artificial
<220> FEATURE:
<223> OTHER INFORMATION: Enterokinase cleavage site

<400> SEQUENCE: 73

Asp Asp Asp Asp Lys
1               5

<210> SEQ ID NO 74
<211> LENGTH: 5
<212> TYPE: PRT
<213> ORGANISM: Artificial
<220> FEATURE:
<223> OTHER INFORMATION: Xa factor cleavage site

<400> SEQUENCE: 74

Ile Glu Asp Gly Arg
1               5

<210> SEQ ID NO 75
<211> LENGTH: 6
<212> TYPE: PRT
<213> ORGANISM: Artificial
<220> FEATURE:
<223> OTHER INFORMATION: Thrombin Cleavage site

<400> SEQUENCE: 75

Leu Val Pro Arg Gly Ser
1               5

<210> SEQ ID NO 76
<211> LENGTH: 7
<212> TYPE: PRT
<213> ORGANISM: Artificial
<220> FEATURE:
<223> OTHER INFORMATION: TEV protease cleavage site

<400> SEQUENCE: 76

Glu Asn Leu Tyr Phe Gln Gly
1               5

<210> SEQ ID NO 77
<211> LENGTH: 8
<212> TYPE: PRT
<213> ORGANISM: Artificial
<220> FEATURE:
<223> OTHER INFORMATION: PreScission protease Cleavage site

<400> SEQUENCE: 77

```
Leu Glu Val Leu Phe Gln Gly Pro
1               5
```

<210> SEQ ID NO 78
<211> LENGTH: 30
<212> TYPE: PRT
<213> ORGANISM: Avian reovirus

<400> SEQUENCE: 78

```
Gly Asp Ala Phe Val Ser Asp Val Glu Pro Leu Pro Ser Gly Ile Pro
1               5                   10                  15

Gly Glu Ser Lys Pro Ser Met Glu Glu Leu Val Asp Asp Leu
            20                  25                  30
```

UNITED STATES PATENT AND TRADEMARK OFFICE
CERTIFICATE OF CORRECTION

| | |
|---|---|
| PATENT NO. | : 10,059,745 B2 |
| APPLICATION NO. | : 13/578556 |
| DATED | : August 28, 2018 |
| INVENTOR(S) | : Brandariz Nunez et al. |

Page 1 of 1

It is certified that error appears in the above-identified patent and that said Letters Patent is hereby corrected as shown below:

In the Specification

Column 13, Line 48: "COST" should be -- COS7 --.

Column 20, Line 20: "COST" should be -- COS7 --.

Column 49, Line 8: "51133" should be -- S1133 --.

Signed and Sealed this
Second Day of October, 2018

Andrei Iancu
*Director of the United States Patent and Trademark Office*